(12) United States Patent
Black

(10) Patent No.: US 7,888,091 B2
(45) Date of Patent: Feb. 15, 2011

(54) FUSION PROTEINS HAVING THYMIDINE KINASE AND GUANYLATE KINASE ACTIVITIES

(75) Inventor: Margaret E. Black, Pullman, WA (US)

(73) Assignee: Darwin Molecular Corporation, Bothell, WA (US)

( * ) Notice: Subject to any disclaimer, the term of this patent is extended or adjusted under 35 U.S.C. 154(b) by 0 days.

(21) Appl. No.: 12/463,261

(22) Filed: May 8, 2009

(65) Prior Publication Data

US 2009/0298156 A1 Dec. 3, 2009

Related U.S. Application Data

(62) Division of application No. 09/173,463, filed on Oct. 14, 1998, now abandoned.

(60) Provisional application No. 60/061,812, filed on Oct. 14, 1997.

(51) Int. Cl.
C12N 9/00 (2006.01)
C12N 9/12 (2006.01)
C12N 15/00 (2006.01)
C07H 21/04 (2006.01)

(52) U.S. Cl. .................... 435/194; 435/183; 435/320.1; 536/23.2

(58) Field of Classification Search ........................ None
See application file for complete search history.

(56) References Cited

U.S. PATENT DOCUMENTS

| 4,851,341 A | 7/1989 | Hopp | 435/68 |
| 5,877,010 A | 3/1999 | Loeb | 435/320.1 |

FOREIGN PATENT DOCUMENTS

| WO | WO95/14102 | 5/1995 |
| WO | WO95/30007 | 11/1995 |
| WO | WO96/06176 | 2/1996 |
| WO | WO97/29196 | 8/1997 |
| WO | WO97/35024 | 9/1997 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession AAT05183, Jun. 14, 1996.
Accession J03366, Feb. 20, 1989.
Graham, et. al., GenBank Accession No. X03764, (1993).
Kit, et. al., Gen Bank Accession Nos. X01712, J02225, (1993).
Balasubramaniam, et. al., "Herpesviral Deoxythymidine Kinases Contain A Site Analogous To The Phosphoryl-Binding Arginine-Rich Region Of Porcine Adenylate Kinase; Comparison Of Secondary Structure Predictions And Conservation," J. Gen. Virol. 71: 2979-2987, 1990.
Black and Hruby, "Identification Of The ATP-Binding Domain Of Vaccinia Virus Thymidine AR Kinase," J. Biol. Chem. 265(29):17584-17592, 1990.

Black and Loeb, "Identification Of Important Residues-Within The Putative Nucleoside Binding Site Of HSV-1 Thymidine Kinase By Random Sequence Selection: Analysis Of Selected Mutants In Vitro," Biochemistry 32:11618-11626, 1993.
Black, et. al., "Creation Of Drug-Specific Herpes Simplex Virus Type 1 Thymidine Kinase Mutants For Gene Therapy," Proc. Natl. Acad. Sci. USA 93:3525-359, 1996.
Black, et. al., "Effect On Substrate Binding Of An Alteration At The Conserved Aspartic Acid-162 In Herpes Simplex Virus Type 1 Thymidine Kinase," J. Gen. Virol. 77:1521-1527, 1996.
Brown, et. al., "Crystal Structures Of The Thymidine Kinase From Herpes Simplex Virus Type-1 Incomplex With Deoxythymidine And Ganciclovir," Nat. Struct. Biol. 2:876-881, 1995.
Chica, et. al., "Semi-Rational Approaches To Engineering Enzyme Activity: Combining The Benefits Of Directed Evolution And Rational Design," Curr. Opin. Boitechnol. 16(4):378-384, 2005.
Deonarain, et al., "Genetic Delivery Of Enzymes For Cancer Therapy," Gene Ther. 2:235-44, 1995.
Drake, et. al., "Metabolism And Activities Of 3'-Azido-2',3'-Dideoxythymidine And 2',3'-Didehydro-2' ,3'-Dideoxythymidine In Herpesvirus Thymidine Kinase Transduced T-Lymphocytes," Antiviral Res. 35: 177-85, 1997.
Esandi, et. al., "Gene Therapy Of Experimental Malignant Mesothelioma Using Adenovirus Vectorsencoding the HSVtk Gene," Gene Ther. 4:280-7, 1997.
Hardy, et. al., "Atomic Structure Of Thymidylate Synthase: Target For Rational Drug Design," Science 235:448-455, 1987.
Hopp, et. al., "A Short Polypeptide Marker Sequence Useful For Recombinant Protein Identification And Purification," Bio/Technology 6:1204-1210, 1988.
Knoll, et. al., "Mapping Of The Active Site Of T7 RNA Polymerase With 8-azidoATP," Biochimica et Biophysica Acta. 1121:252-260, 1992.
McKnight, "The Nucleotide Sequence And Transcript Map Of The Herpes Simplex Virus Thymidine Kinase Gene," Nucleic Acids Res. 8(24):5949-5964, 1980.
Montfort, et. al., "Structure, Multiple Site Binding, And Segmental Accommodation In Thymidylate Synthase On Binding dUMP And An Anti-Folate," Biochem. 29: 6964-6977, 1990.

(Continued)

Primary Examiner—Christian L Fronda
(74) Attorney, Agent, or Firm—K&L Gates LLP; C. Rachal Winger

(57) ABSTRACT

The present invention provides isolated nucleic acid molecules encoding a Herpesviridae thymidine kinase enzyme comprising one or more mutations, at least one of the mutations encoding an amino acid substitution located toward the N-terminus from a DRH nucleoside binding site which increases a biological activity of the thymidine kinase, as compared to unmutated thymidine kinase. Such mutations include amino acid substitutions within a Q substrate binding domain which increases a biological activity of the thymidine kinase, as compared to unmutated thymidine kinase. Within a further aspect, fusion proteins are provided which have both guanylate kinase and thymidine kinase biological properties. Also provided are vectors suitable for expressing such DNA molecules, as well as methods for utilizing such vectors.

11 Claims, 29 Drawing Sheets

OTHER PUBLICATIONS

Munch-Petersen, et. al., "Diverging Substrate Specificity Of Pure Human Thymidine Kinases 1 And 2 Against Antiviral Dideoxynucleosides," J Biol. Chem. 266:9032-8, 1991.

Munir, et. al., "Permissible Amino Acid Substitutions Within The Putative Nucleoside Binding Site Of Herpes Simplex Virus Type 1 Encoded Thymidine Kinase Established By Random Sequence Mutagenesis," J. Biol. Chem. 267:6584-9, 1992.

Munir, et. al., "Thymidine Kinase Mutants Obtained By Random Sequence Selection," Proc. Natl. Acad. Sci. USA 90: 4012-4016, 1993.

Sanderson, et. al., "Purification And Crystallization Of Thymidine Kinase From Herpes Simplex Virus Type 1," J. Mol. Biol. 202:917-919, 1988.

Sen, et. al., "Developments In Directed Evolution For Improving Enzyme Functions," Appl. Biochem. Biotechnol. 143(3):212-223, 2007.

Waldman et al., "Purification And Characterization Of Herpes Simplex Virus (Type 1) Thymidine Kinase Produced In *Escherichia coli* By A High Efficiency Expression Plasmid Utilizing A Lambda PL Promoter And CI857 Temperature-Sensitive Repressor," J Biol. Chem. 258(19):11571-5, 1983.

\* cited by examiner

FIG. 1
Steps
1. Anneal oligo I with oligo II
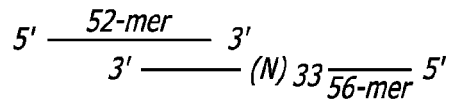
2. Extend with the large fragment of E. coli Pol. I
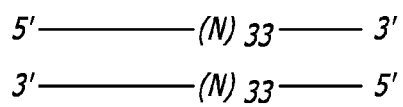
3. PCR amplification
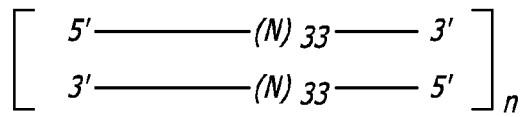
4. Digestion with Kpn I and Sac I
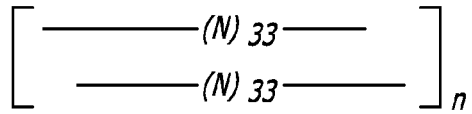
5. Digestion of pMDC with Kpn I and Sac I followed by ligation with random sequence containing fragment
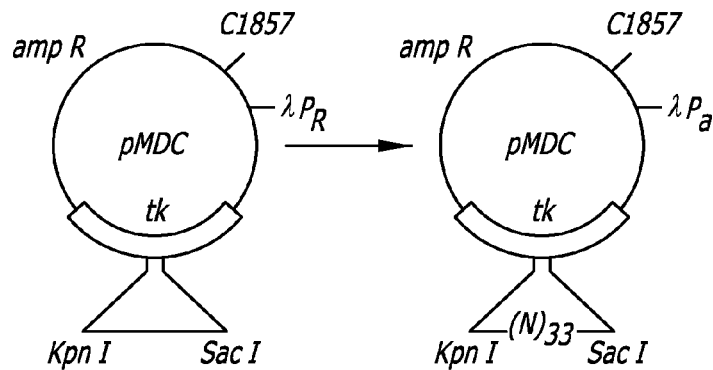
6. Transform KY895 and score on carbenicillin and TK selection media
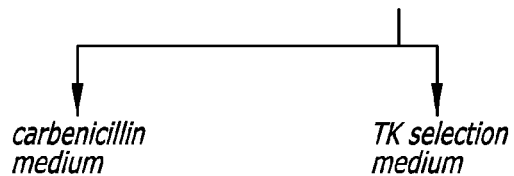

| | | | | | | | | | | | |
|---|---|---|---|---|---|---|---|---|---|---|---|
| 165 | 166 | 167 | 168 | 169 | 170 | 171 | 172 | 173 | 174 | 175 | |
| CCC | ATC | GCC | GCC | CTC | CTG | TGC | TAC | CCG | GCC | GCG | Wild-Type |
| Pro | Ile | Ala | Ala | Leu | Leu | Cys | Tyr | Pro | Ala | Ala | |
| | | | | | | | | | | | |
| CCC | ATC | GCC | GCC | CTC | ATC | TGC | TAC | CCG | GCC | GCG | TKF 105 |
| Pro | Ile | Ala | Ala | Leu | Ile | Cys | Tyr | Pro | Ala | Ala | |
| | | | | | | | | | | | |
| CCC | ATC | GCC | GCC | CTC | GTG | TGC | TAC | CCG | GCC | GCG | TKL 208 |
| Pro | Ile | Ala | Ala | Leu | Val | Cys | Tyr | Pro | Ala | Ala | |
| | | | | | | | | | | | |
| CAC | ATC | TCG | GCC | CTC | CTG | TGC | TAC | CCG | GTC | GCG | TKF 2 |
| His | Ile | Ser | Ala | Leu | Leu | Cys | Tyr | Pro | Val | Ala | |

*FIG. 3*

LIF-ALL Library

HSV-1 TK  A  L  T  L  I  F  | D  R  H |  P  I  A  A  L  L  | C  Y  P | I
residue    150   160 161     Site 3      168 169 170    Site 4
number Transformants screened   100% random
Active Clones            1.1 x 10⁶
Selection Plates         428
Selection Medium         426
                         18 nucleotides

Mutants Sensitive to GCV or ACV

| GCV | | ACV | |
|---|---|---|---|
| Selection | No. mutants | Selection | No. mutants |
| dT (2 μg/ml) | 426 | dT (2 μg/ml) | 426 |
| GCV* (2 μg/ml) | 197 | | |
| GCV* (1 μg/ml) | 51 | ACV* (1 μg/ml) | 116 |
| GCV* (0.5 μg/ml) | 47 | | |
| GCV* (0 μg/ml) | [26] | ACV* (0 μg/ml) | [54] |

*with thymidine (1 μg/ml)

FIG. 17

Nucleotide Changes in Selected TK Mutants

| | 150 S TCA | H CAT | A GCC | P CCG | 155 P CCC | A GCC | L CTC | T ACC | 160 I ATC | F TTC | D GAC | R CGC | H CAT | 165 P CCC | I ATC | A GCC | L CTC | L CTG | 170 C TGC | Y TAC | P CCG |
|---|---|---|---|---|---|---|---|---|---|---|---|---|---|---|---|---|---|---|---|---|---|
| WT | TCA | CAT | GCC | CCG | CCC | GCC | CTC | ACC | ATC | TTC | GAC | CGC | CAT | CCC | ATC | GCC | CTC | CTG | TGC | TAC | CCG |
| 30 | | | GTC | | | | | | ATT | TTG | GCT | | | | | | | | | | |
| 51 | | | | | CCT | | | | GTA | ATA | ACA | | | | | | | | | | |
| 75 | | | | | | TCC | | | CTA | CTA | CTG | | | | | | | | | | |
| 84 | | | | -3 (CCC) | | | | | TTG | | CTG | | | | | | | | | | |
| 132 | | | | | | | | | ATG | TTC | ATG | | | | | | | | | | |
| 197 | | | | | -6 (CCG GCC) | | | | ATA | TTG | CTT | | | | | GCA | | | | | |
| 226 | | | | | | -3 (G GC) | | | TTT | TAT | TAT | | | | | | | | | | |
| 302 | | | | | | | -3 (CCC) | | TTG | TTC | CTC | | | | | | | | | | |
| 340 | | | | | | | | | GTA | TTA | | CGT | | | | | | | | | |
| 411 | | | | | | | | | TGT | TTT | CTC | | | | | | | | | | CCT |

Italics denote nucleotides that differ from the wild-type tk sequence.

FIG. 18

Amino Acid Sequence and Phosphorylation Level of Mutant TKs

| Number | Sequence | | | | | | Relative Activities (% HSVTK) | | |
|---|---|---|---|---|---|---|---|---|---|
| | | | | | | | Thymidine | GCV | ACV |
| HSVTK(WT) | L | I | F | A | L | L | 100% | 100% | 100% |
| 30 | I | L | A | Y | F | – | 2% | 64% | 72% |
| 51 | V | – | T | C | – | – | 6.7% | 3.5% | 13% |
| 75 | – | L | L | V | M | – | 65% | 71% | 434% |
| 84 | – | – | L | S | Y | C | 30% | 73% | 199% |
| 132 | M | F | M | H | N | V | <0.5% | 26% | 38% |
| 197 | I | L | L | I | Y | – | <0.5% | <0.5% | 20% |
| 226 | F | Y | Y | P | F | V | 15% | 26% | 38% |
| 302 | – | F | L | L | M | C | 8% | 11% | 77% |
| 340 | – | V | L | Y | Y | – | <0.5% | 13% | 47% |
| 411 | C | F | L | Y | Y | – | <0.5% | 21% | 24% |

The following clones contain additional amino acid changes /deletions outside the randomized region:

| 30 | A152V |
|---|---|
| 84 | A156S |
| 197 | -6 deletion (P155 A156) |
| 226 | -3 deletion (P154) |
| 340 | -3 deletion (A156) |
| 411 | -3 deletion (p155) |

Semi-Randomized Oligonucleotides

DMO2211 5' AGGCTGGGAGCTCACATGCCCCGCCCCCGGCCCTCACC(AC)TCTT(GC)(GC)(CT)CGACCGCCA 3'

DMO2212 5' ATAAGGTACCGCGCGGCCGGGTAGCACAG(AC)(AT)G(TA)(CA)GGCGATGGGATGGCGG 3'

Anticipated AminoAcid Substitutions

| | | | | | |
|---|---|---|---|---|---|
| HSV-1 TK (wt) residues 159-161 and 168-169 | L | I | F | A | L |
| | I/L | L/F | A/V/P/L | D/Y/V/F | F/Y/L/I/M/N/K/stop |

*FIG. 21*

| | | |
|---|---|---|
| DMO-1860 | CGCCTCGACCAGGGTGAG ATATCGGCCGGGGACGCGGCGGTGGTAATGACAAGCG | 55 MER |
| DMO-1861 | GAACGGCGTCGGTCACGGC ATAAGGCATGCCCATTGTTATCTGGGCGCTTGTCATTAC | 58 MER |
| DMO-1893 | GGCGCCTCCGAGACAATCGCGAACATCTACACCACACAACACCGCCTCGACCAGGGTGAG | 59 MER |
| DMO-1894 | TCGACTGAGCTCCCAGCCTCCCCCCGATATGAGGAGCCAGAACGGCGTCGGTCACGGC | 60 MER |
| DMO-1895 | GCAGCTGGCGCCTCCGAGACAATC | 24 MER |
| DMO-1896 | TCGACTGAGCTCCCAGCCT | 19 MER |

*FIG. 22*

```
ATGGCTTCGT ACCCCGGCCA TCAACACGCG TCTGCGTTCG ACCAGGCTGC GCGTTCTCGC    60
GGCCATAGCA ACCGACGTAC GGCGTTGCGC CCTCGCCGGC AGCAAGAAGC CACGGAAGTC   120
CGCCTGGAGC AGAAAATGCC CACGCTACTG CGGGTTTATA TAGACGGTCC TCACGGGATG   180
GGGAAAACCA CCACCACGCA ACTGCTGGTG GCCCTGGGTT CGCGCGACGA TATCGTCTAC   240
GTACCCGAGC CGATGACTTA CTGGCAGGTG CTGGGGGCTT CCGAGACAAT CGCGAACATC   300
TACACCACAC AACACCGCCT CGACCAGGGT GAGATATCGG CCGGGACGC GGCGGTGGTA    360
ATGACAAGCG CCCAGATAAC AATGGGCATG CCTTATGCCG TGACCGACGC CGTTCTGGCT   420
CCTCATATCG GGGGGAGGC TGGGAGCTCA CATGCCCCGC CCCCGGCCCT CACCCTCATC    480
TTCGACCGCC ATCCCATCGC CGCCCTCCTG TGCTACCCGG CCGCGCGGTA CCTTATGGGC   540
AGCATGACCC CCCAGGCCGT GCTGGCGTTC GTGGCCCTCA TCCCGCCGAC CTTGCCCGGC   600
ACCAACATCG TGCTTGGGGC CCTTCCGGAG GACAGACACA TCGACCGCCT GGCCAAACGC   660
CAGCGCCCCG GCGAGCGGCT GGACCTGGCT ATGCTGGCTG CGATTCGCCG CGTTTACGGG   720
CTACTTGCCA ATACGGTGCG GTATCTGCAG TGCGGCGGGT CGTGGCGGGA GGACTGGGGA   780
CAGCTTTCGG GGACGGCCGT GCCGCCCCAG GGTGCCGAGC CCCAGAGCAA CGCGGGCCCA   840
CGACCCCATA TCGGGGACAC GTTATTTACC CTGTTTCGGG CCCCCGAGTT GCTGGCCCCC   900
AACGGCGACC TGTATAACGT GTTTGCCTGG GCCTTGGACG TCTTGGCCAA ACGCCTCCGT   960
TCCATGCACG TCTTTATCCT GGATTACGAC CAATCGCCCG CCGGCTGCCG GGACGCCCTG  1020
CTGCAACTTA CCTCCGGGAT GGTCCAGACC CACGTCACCA CCCCCGGCTC CATACCGACG  1080
ATATGCGACC TGGCGCGCAC GTTTGCCCGG GAGATGGGGG AGGCTAACTG A           1131
```

FIG. 23

Human Guanylate Kinase

```
1                                               31
GGA TCC ATG GCG GGC CCC AGG CCT GTG GTG CTG AGC GGG CCT TCG GGA GCT GGG AAG AGC
        Met ala gly pro arg pro val val leu ser gly pro ser gly ala gly lys ser 61                                              91
ACC CTG CTG AAG AGG CTG CTC CAG GAG CAC AGC GGC ATC TTT GGC TTC AGC GTG TCC CAT
thr leu leu lys arg leu leu gln glu his ser gly ile phe gly phe ser val ser his 121                                             151
ACC ACG AGG AAC CCG AGG CCC GGC GAG GAG AAC GGC AAA GAT TAC TAC TTT GTA ACC AGG
thr thr arg asn pro arg pro gly glu glu asn gly lys asp tyr tyr phe val thr arg 181                                             211
GAG GTG ATG CAG CGT GAC ATA GCA GCC GGC GAC TTC ATC GAG CAT GCC GAG TTC TCG GGG
glu val met gln arg asp ile ala ala gly asp phe ile glu his ala glu phe ser gly 241                                             271
AAC CTG TAT GGC ACG AGC AAG GTG GCG GTG GAC GCC GTG CAG GCC ATG AAC CGC ATC TGT
asn leu tyr gly thr ser lys val ala val asp ala val gln ala met asn arg ile cys 301                                             331
GTG CTG GAC GTG GAC CTG CAG GGT GTG CGG AAC ATC AAG GCC ACC GAT CTG CGG CCC ATC
val leu asp val asp leu gln gly val arg asn ile lys ala thr asp leu arg pro ile 361                                             391
TAC ATC TCT GTG CAG CCG CCT TCA CTG CAC GTG CTG GAG CAG CGG CTG CGG CAC CGC AAC
tyr ile ser val gln pro pro ser leu his val leu glu gln arg leu arg his arg asn 421                                             451
ACT GAA ACC GAG GAG AGC CTG GTG AAG CGG CTG GCT GCT GCC CAC CCC GAC ATG GAG AGC
thr glu thr glu glu ser leu val lys arg leu ala ala ala gln ala asp met glu ser 481                                             511
AGC AAG GAG CCC GGC CTG TTT GAT GTG GTC ATC ATT AAC GAC AGC CTG GAC CAC GCC TAC
ser lys glu pro gly leu phe asp val val ile ile asn asp ser leu asp gln ala tyr 541                                             571
GCA GAG CTG AAG GAG GCG CTC TCT GAG GAA ATC AAG AAA GCT CAA AGG ACC GGC GCC TGA
ala glu leu lys glu ala leu ser glu glu ile lys lyr ala gln arg thr gly ala OPA

601
GGA TCC
```

FIG. 24

Murine Guanylate Kinase

```
1                               31
CTG GGT CGG GTC CCC GCG GAC GGC ATG GCA GGA CCT AGG CCA GTA GTG CTG AGC GGG CCG
                                Met ala gly pro arg pro val val leu ser gly pro 61                              91
TCA GGG GCA GGG AAG AGC ACT CTG CTC AAG AAG CTG TTC CAG GAG CAC AGC AGC ATC TTC
ser gly ala gly lys ser thr leu leu lys lys leu phe gln glu his ser ser ile phe 121                             151
GGC TTC AGT GTG TCC CAT ACT ACA AGG AAC CCA CGA CCT GGT GAA GAA GAT GGC AAA GAT
gly phe ser val ser his thr thr arg asn pro arg pro gly glu glu asp gly lys asp 181                             211
TAC TAC TTT GTG ACC AGG GAG ATG ATG CAG CGT GAT ATT GCA GCA GGG GAC TTC ATT GAG
tyr tyr phe val thr arg glu met met gln arg asp ile ala ala gly asp phe ile glu 241                             271
CAT GCT GAG TTC TCA GGG AAC CTG TAC GGG ACA AGC AAG GAA GCT GTT CGG GCT GTG CAG
his ala glu phe ser gly asn leu tyr gly thr ser lys glu ala val arg ala val gln 301                             331
GCC ATG AAC CGC ATC TGC GTG CTA GAT GTC GAC CTA CAA GGT GTG CGC AGC ATC AAG AAG
ala met asn arg ile cys val leu asp val asp leu gln gly val arg ser ile lys lys 361                             391
ACT GAT CTG TGT CCC ATC TAC ATC TTT GTG CAG CCT CCC TCG CTG GAC GTG CTG GAG CAA
thr asp leu cys pro ile tyr ile phe val gln pro pro ser leu asp val leu glu gln 421                             451
CGA CTG CGA CTG CGC AAC ACT GAG ACT GAG GAG AGT CTG GCA AAG CGG CTG GCA GCT GCA
arg leu arg leu arg asn thr glu thr glu glu ser leu ala lys arg leu ala ala ala 481                             511
CGG ACA GAC ATG GAG AGC AGC AAG GAG CCT GGC TTG TTT GAC CTG GTG ATC ATC AAT GAC
arg thr asp met glu ser ser lys glu pro gly leu phe asp leu val ile ile asn asp 541                             571
GAC CTG GAT AAA GCC TAT GCA ACC CTG AAG CAG GCG CTC TCT GAG GAA ATC AAG AAA GCA
asp leu asp lys ala tyr ala thr leu lys gln ala leu ser glu glu ile lys lys ala 601                             631
CAG GGA ACT GGC CAC GCC TGA AGG CCT GCT TCA TTC CAC AGA GTG ATG TCT GTG GTC TAA
gln gly thr gly his ala OPA
```

FIG. 25

SEQUENCE LISTING

<160> NUMBER OF SEQ ID NOS: 172

<210> SEQ ID NO 1
<211> LENGTH: 1131
<212> TYPE: DNA
<213> ORGANISM: Herpesviridae sp.

<400> SEQUENCE: 1

```
atggcttcgt accccggcca tcaacacgcg tctgcgttcg accaggctgc gcgttctcgc      60
ggccatagca accgacgtac ggcgttgcgc cctcgccggc agcaagaagc cacggaagtc     120
cgcctggagc agaaaatgcc cacgctactg cgggtttata tagacggtcc tcacgggatg     180
gggaaaacca ccaccacgca actgctggtg gccctgggtt cgcgcgacga tatcgtctac     240
gtacccgagc cgatgactta ctggcaggtg ctgggggctt ccgagacaat cgcgaacatc     300
tacaccacac aacaccgcct cgaccagggt gagatatcgg ccggggacgc ggcggtggta     360
atgacaagcg cccagataac aatgggcatg ccttatgccg tgaccgacgc cgttctggct     420
cctcatatcg gggggaggc tgggagctca catgccccgc ccccggccct caccctcatc     480
```

| | |
|---|---|
| ttcgaccgcc atccatcgc cgccctcctg tgctacccgg ccgcgcggta ccttatgggc | 540 |
| agcatgaccc cccaggccgt gctggcgttc gtggccctca tcccgccgac cttgcccggc | 600 |
| accaacatcg tgcttggggc ccttccggag gacagacaca tcgaccgcct ggccaaacgc | 660 |
| cagcgccccg gcgagcggct ggacctggct atgctggctg cgattcgccg cgtttacggg | 720 |
| ctacttgcca atacggtgcg gtatctgcag tgcggcgggt cgtggcggga ggactgggga | 780 |
| cagctttcgg ggacggccgt gccgcccag gtgccgagc cccagagcaa cgcgggccca | 840 |
| cgaccccata tcggggacac gttatttacc ctgtttcggg ccccgagtt gctggcccc | 900 |
| aacggcgacc tgtataacgt gtttgcctgg gccttggacc tcttggccaa cgcctccgt | 960 |
| tccatgcacg tctttatcct ggattacgac caatcgcccg ccggctgccg ggacgccctg | 1020 |
| ctgcaactta cctccgggat ggtccagacc cacgtcacca ccccggctc ataccgacg | 1080 |
| atatgcgacc tggcgcgcac gtttgcccgg gagatggggg aggctaactg a | 1131 |

<210> SEQ ID NO 2
<211> LENGTH: 52
<212> TYPE: DNA
<213> ORGANISM: Artificial Sequence
<220> FEATURE:
<223> OTHER INFORMATION: Oligonucleotide for generation of TK mutants

<400> SEQUENCE: 2
tgggagctca catgccccgc ccccggccct caccctcatc ttcgatcgcc at           52

<210> SEQ ID NO 3
<211> LENGTH: 56
<212> TYPE: DNA
<213> ORGANISM: Artificial Sequence
<220> FEATURE:
<223> OTHER INFORMATION: Oligonucleotide for generation of TK mutants
<220> FEATURE:
<221> NAME/KEY: misc_feature
<222> LOCATION: (12)..(44)
<223> OTHER INFORMATION: n is a, c, g, or t

<400> SEQUENCE: 3
atgaggtacc gnnnnnnnnn nnnnnnnnnn nnnnnnnnnn nnnnatggcg atcgaa       56

<210> SEQ ID NO 4
<211> LENGTH: 17
<212> TYPE: DNA
<213> ORGANISM: Artificial Sequence
<220> FEATURE:
<223> OTHER INFORMATION: Primer

<400> SEQUENCE: 4
cccctccagc gcggtac                                                   17

<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5
cgcgctcgag gggagct                                                   17

<210> SEQ ID NO 6
<211> LENGTH: 21
<212> TYPE: DNA
<213> ORGANISM: Artificial Sequence -continued

```
<220> FEATURE:
<223> OTHER INFORMATION: Primer

<400> SEQUENCE: 6
tgggagctca catgccccgc c                                              21

<210> SEQ ID NO 7
<211> LENGTH: 11
<212> TYPE: DNA
<213> ORGANISM: Artificial Sequence
<220> FEATURE:
<223> OTHER INFORMATION: Primer

<400> SEQUENCE: 7
atgaggtacc g                                                         11

<210> SEQ ID NO 8
<211> LENGTH: 52
<212> TYPE: DNA
<213> ORGANISM: Artificial Sequence
<220> FEATURE:
<223> OTHER INFORMATION: Oligonucleotides for generation of TK mutants

<400> SEQUENCE: 8
tgggagctca catgccccgc ccccggccct caccctcatc ttcgatcgcc at            52

<210> SEQ ID NO 9
<211> LENGTH: 70
<212> TYPE: DNA
<213> ORGANISM: Artificial Sequence
<220> FEATURE:
<223> OTHER INFORMATION: Oligonucleotides for generation of TK mutants

<400> SEQUENCE: 9
tgggagctca catgccccgc ccccggccct caccctcatc ttcgaccgcc atcccatcgc    60
cgccctcctg                                                           70

<210> SEQ ID NO 10
<211> LENGTH: 38
<212> TYPE: DNA
<213> ORGANISM: Artificial Sequence
<220> FEATURE:
<223> OTHER INFORMATION: Oligonucleotides for generation of TK mutants

<400> SEQUENCE: 10
atgaggtacc gcgcagctgg gtagcacagg agggcggc                            38

<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11
catgccttat gccgtga                                                   17

<210> SEQ ID NO 12
<211> LENGTH: 33
<212> TYPE: DNA
<213> ORGANISM: Herpesviridae sp.
<220> FEATURE:
<221> NAME/KEY: CDS
<222> LOCATION: (1)..(33)

<400> SEQUENCE: 12
```

```
ccc atc gcc gcc ctc ctg tgc tac ccg gcc gcg                           33
Pro Ile Ala Ala Leu Leu Cys Tyr Pro Ala Ala
1               5                   10
```

<210> SEQ ID NO 13
<211> LENGTH: 11
<212> TYPE: PRT
<213> ORGANISM: Herpesviridae sp.

<400> SEQUENCE: 13

```
Pro Ile Ala Ala Leu Leu Cys Tyr Pro Ala Ala
1               5                   10
```

<210> SEQ ID NO 14
<211> LENGTH: 33
<212> TYPE: DNA
<213> ORGANISM: Artificial Sequence
<220> FEATURE:
<223> OTHER INFORMATION: HSVTK Mutant
<220> FEATURE:
<221> NAME/KEY: CDS
<222> LOCATION: (1)..(33)

<400> SEQUENCE: 14

```
ccc atc gcc tcc ctc ctg tgc tac ccg gcc gcg                           33
Pro Ile Ala Ser Leu Leu Cys Tyr Pro Ala Ala
1               5                   10
```

<210> SEQ ID NO 15
<211> LENGTH: 11
<212> TYPE: PRT
<213> ORGANISM: Artificial Sequence
<220> FEATURE:
<223> OTHER INFORMATION: HSVTK Mutant

<400> SEQUENCE: 15

```
Pro Ile Ala Ser Leu Leu Cys Tyr Pro Ala Ala
1               5                   10
```

<210> SEQ ID NO 16
<211> LENGTH: 33
<212> TYPE: DNA
<213> ORGANISM: Artificial Sequence
<220> FEATURE:
<223> OTHER INFORMATION: HSVTK Mutant
<220> FEATURE:
<221> NAME/KEY: CDS
<222> LOCATION: (1)..(33)

<400> SEQUENCE: 16

```
tcc atc ggc gcc cta cag tgc tac ccg gtc gcg                           33
Ser Ile Gly Ala Leu Gln Cys Tyr Pro Val Ala
1               5                   10
```

<210> SEQ ID NO 17
<211> LENGTH: 11
<212> TYPE: PRT
<213> ORGANISM: Artificial Sequence
<220> FEATURE:
<223> OTHER INFORMATION: HSVTK Mutant

<400> SEQUENCE: 17

```
Ser Ile Gly Ala Leu Gln Cys Tyr Pro Val Ala
1               5                   10
```

<210> SEQ ID NO 18
<211> LENGTH: 33

```
<212> TYPE: DNA
<213> ORGANISM: Artificial Sequence
<220> FEATURE:
<223> OTHER INFORMATION: HSVTK Mutant
<220> FEATURE:
<221> NAME/KEY: CDS
<222> LOCATION: (1)..(33)

<400> SEQUENCE: 18 ccc atc gcc acc ctg ctg tgc tac ccg gcc gcg      33
Pro Ile Ala Thr Leu Leu Cys Tyr Pro Ala Ala
1               5                   10

<210> SEQ ID NO 19
<211> LENGTH: 11
<212> TYPE: PRT
<213> ORGANISM: Artificial Sequence
<220> FEATURE:
<223> OTHER INFORMATION: HSVTK Mutant

<400> SEQUENCE: 19

Pro Ile Ala Thr Leu Leu Cys Tyr Pro Ala Ala
1               5                   10

<210> SEQ ID NO 20
<211> LENGTH: 33
<212> TYPE: DNA
<213> ORGANISM: Artificial Sequence
<220> FEATURE:
<223> OTHER INFORMATION: HSVTK Mutant
<220> FEATURE:
<221> NAME/KEY: CDS
<222> LOCATION: (1)..(33)

<400> SEQUENCE: 20 ccc atc gcc gcc tta ctg tta tac ccg acc gcg      33
Pro Ile Ala Ala Leu Leu Leu Tyr Pro Thr Ala
1               5                   10

<210> SEQ ID NO 21
<211> LENGTH: 11
<212> TYPE: PRT
<213> ORGANISM: Artificial Sequence
<220> FEATURE:
<223> OTHER INFORMATION: HSVTK Mutant

<400> SEQUENCE: 21

Pro Ile Ala Ala Leu Leu Leu Tyr Pro Thr Ala
1               5                   10

<210> SEQ ID NO 22
<211> LENGTH: 33
<212> TYPE: DNA
<213> ORGANISM: Artificial Sequence
<220> FEATURE:
<223> OTHER INFORMATION: HSVTK Mutant
<220> FEATURE:
<221> NAME/KEY: CDS
<222> LOCATION: (1)..(33)

<400> SEQUENCE: 22 ccc atc gcc gcc ctc gtg tgc tac ccg gcc gcg      33
Pro Ile Ala Ala Leu Val Cys Tyr Pro Ala Ala
1               5                   10

<210> SEQ ID NO 23
<211> LENGTH: 11
<212> TYPE: PRT
<213> ORGANISM: Artificial Sequence
```

```
<220> FEATURE:
<223> OTHER INFORMATION: HSVTK Mutant

<400> SEQUENCE: 23

Pro Ile Ala Ala Leu Val Cys Tyr Pro Ala Ala
1               5                   10

<210> SEQ ID NO 24
<211> LENGTH: 58
<212> TYPE: DNA
<213> ORGANISM: Artificial Sequence
<220> FEATURE:
<223> OTHER INFORMATION: Oligonucleotide for generation of TK mutants
<220> FEATURE:
<221> NAME/KEY: misc_feature
<222> LOCATION: (1)..(58)
<223> OTHER INFORMATION: N = A, C, T or G

<400> SEQUENCE: 24
tgggagctca catgccccgc ccccggccct caccnnnnnn nnngaccgcc atcccatc      58

<210> SEQ ID NO 25
<211> LENGTH: 34
<212> TYPE: DNA
<213> ORGANISM: Artificial Sequence
<220> FEATURE:
<223> OTHER INFORMATION: Oligonucleotide for generation of TK mutants
<220> FEATURE:
<221> NAME/KEY: misc_feature
<222> LOCATION: (1)..(51)
<223> OTHER INFORMATION: n = A, T, C, or G

<400> SEQUENCE: 25
dactactgga tccatggcgg gccccaggcc tgtg                                34

<210> SEQ ID NO 26
<211> LENGTH: 33
<212> TYPE: DNA
<213> ORGANISM: Artificial Sequence
<220> FEATURE:
<223> OTHER INFORMATION: Primer

<400> SEQUENCE: 26
actactggat ccatggcggg ccccaggcct gtg                                 33

<210> SEQ ID NO 27
<211> LENGTH: 33
<212> TYPE: DNA
<213> ORGANISM: Artificial Sequence
<220> FEATURE:
<223> OTHER INFORMATION: Primer

<400> SEQUENCE: 27
tactacggat cctcaggcgg cggtcctttg agc                                 33

<210> SEQ ID NO 28
<211> LENGTH: 18
<212> TYPE: DNA
<213> ORGANISM: Artificial Sequence
<220> FEATURE:
<223> OTHER INFORMATION: Primer

<400> SEQUENCE: 28
ctgctgaaga ggctgctc                                                  18

<210> SEQ ID NO 29
<211> LENGTH: 19
```

<212> TYPE: DNA
<213> ORGANISM: Artificial Sequence
<220> FEATURE:
<223> OTHER INFORMATION: Primer

<400> SEQUENCE: 29
acacagatgc ggtttcatg                                                    19

<210> SEQ ID NO 30
<211> LENGTH: 18
<212> TYPE: DNA
<213> ORGANISM: Artificial Sequence
<220> FEATURE:
<223> OTHER INFORMATION: Primer

<400> SEQUENCE: 30
ctggacgtgg acctgcag                                                     18

<210> SEQ ID NO 31
<211> LENGTH: 18
<212> TYPE: DNA
<213> ORGANISM: Artificial Sequence
<220> FEATURE:
<223> OTHER INFORMATION: Primer

<400> SEQUENCE: 31
gttaatgatg accacatc                                                     18

<210> SEQ ID NO 32
<211> LENGTH: 18
<212> TYPE: DNA
<213> ORGANISM: Artificial Sequence
<220> FEATURE:
<223> OTHER INFORMATION: Primer

<400> SEQUENCE: 32
tgtaaaacga cggccagt                                                     18

<210> SEQ ID NO 33
<211> LENGTH: 18
<212> TYPE: DNA
<213> ORGANISM: Artificial Sequence
<220> FEATURE:
<223> OTHER INFORMATION: Primer

<400> SEQUENCE: 33
caggaaacag ctatgacc                                                     18

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
tgtgtcccat actactacaa g                                                 21

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
tgagaactca gcagcatgct c                                              21

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36
gtgctagatg tcgaccta                                                  18

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
acctggataa agcctatg                                                  18

<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38
aagcaggcgc tctctctga                                                 19

<210> SEQ ID NO 39
<211> LENGTH: 18
<212> TYPE: DNA
<213> ORGANISM: Artificial Sequence
<220> FEATURE:
<223> OTHER INFORMATION: Primer

<400> SEQUENCE: 39
ctatttctca tatgatgt                                                  18

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
gttacagtgt ctctagag                                                  18

<210> SEQ ID NO 41
<211> LENGTH: 24
<212> TYPE: DNA
<213> ORGANISM: Artificial Sequence
<220> FEATURE:
<223> OTHER INFORMATION: Primer

<400> SEQUENCE: 41
ctaggtcctg ccatggcgtc cgcg                                           24

<210> SEQ ID NO 42
<211> LENGTH: 27
<212> TYPE: DNA
<213> ORGANISM: Artificial Sequence
<220> FEATURE:
<223> OTHER INFORMATION: Primer

<400> SEQUENCE: 42
actactacta gatctcgatc ccgcgaa                                            27

<210> SEQ ID NO 43
<211> LENGTH: 41
<212> TYPE: DNA
<213> ORGANISM: Artificial Sequence
<220> FEATURE:
<223> OTHER INFORMATION: Primer

<400> SEQUENCE: 43
atgatgatga tgatggctgc tagccatagt atatctcctt c                            41

<210> SEQ ID NO 44
<211> LENGTH: 39
<212> TYPE: DNA
<213> ORGANISM: Artificial Sequence
<220> FEATURE:
<223> OTHER INFORMATION: Primer

<400> SEQUENCE: 44
cggcaccagg ccgctgctgt gatgatgatg atgatggct                               39

<210> SEQ ID NO 45
<211> LENGTH: 42
<212> TYPE: DNA
<213> ORGANISM: Artificial Sequence
<220> FEATURE:
<223> OTHER INFORMATION: Primer

<400> SEQUENCE: 45
agtagtatcc atggagctgc cgcgcggcac caggccgctg ct                           42

<210> SEQ ID NO 46
<211> LENGTH: 21
<212> TYPE: PRT
<213> ORGANISM: Artificial Sequence
<220> FEATURE:
<223> OTHER INFORMATION: Vector fusion peptide

<400> SEQUENCE: 46

Met Ala Ser Ser His His His His His His Ser Ser Gly Leu Val Pro
1               5                   10                  15

Arg Gly Ser Ser Met
            20

<210> SEQ ID NO 47
<211> LENGTH: 19
<212> TYPE: PRT
<213> ORGANISM: Herpesviridae sp.

<400> SEQUENCE: 47

Ala Leu Thr Leu Ile Phe Asp Arg His Pro Ile Ala Ala Leu Leu Cys
1               5                   10                  15

Tyr Pro Ile

<210> SEQ ID NO 48
<211> LENGTH: 606
<212> TYPE: DNA
<213> ORGANISM: Homo sapiens
<220> FEATURE:
<221> NAME/KEY: CDS

<222> LOCATION: (7)..(597)

<400> SEQUENCE: 48

```
ggatcc atg gcg ggc ccc agg cct gtg gtg ctg agc ggg cct tcg gga        48
       Met Ala Gly Pro Arg Pro Val Val Leu Ser Gly Pro Ser Gly
       1               5                   10 gct ggg aag agc acc ctg ctg aag agg ctg ctc cag gag cac agc ggc        96
Ala Gly Lys Ser Thr Leu Leu Lys Arg Leu Leu Gln Glu His Ser Gly
15                  20                  25                  30 atc ttt ggc ttc agc gtg tcc cat acc acg agg aac ccg agg ccc ggc        144
Ile Phe Gly Phe Ser Val Ser His Thr Thr Arg Asn Pro Arg Pro Gly
                35                  40                  45 gag gag aac ggc aaa gat tac tac ttt gta acc agg gag gtg atg cag        192
Glu Glu Asn Gly Lys Asp Tyr Tyr Phe Val Thr Arg Glu Val Met Gln
        50                  55                  60 cgt gac ata gca gcc ggc gac ttc atc gag cat gcc gag ttc tcg ggg        240
Arg Asp Ile Ala Ala Gly Asp Phe Ile Glu His Ala Glu Phe Ser Gly
65                  70                  75 aac ctg tat ggc acg agc aag gtg gcg gtg cag gcc gtg cag gcc atg        288
Asn Leu Tyr Gly Thr Ser Lys Val Ala Val Gln Ala Val Gln Ala Met
            80                  85                  90 aac cgc atc tgt gtg ctg gac gtg gac ctg cag ggt gtg cgg aac atc        336
Asn Arg Ile Cys Val Leu Asp Val Asp Leu Gln Gly Val Arg Asn Ile
95                  100                 105                 110 aag gcc acc gat ctg cgg ccc atc tac atc tct gtg cag ccg cct tca        384
Lys Ala Thr Asp Leu Arg Pro Ile Tyr Ile Ser Val Gln Pro Pro Ser
                115                 120                 125 ctg cac gtg ctg gag cag cgg ctg cgg cag cgc aac act gaa acc gag        432
Leu His Val Leu Glu Gln Arg Leu Arg Gln Arg Asn Thr Glu Thr Glu
        130                 135                 140 gag agc ctg gtg aag cgg ctg gct gct gcc cag gcc gac atg gag agc        480
Glu Ser Leu Val Lys Arg Leu Ala Ala Ala Gln Ala Asp Met Glu Ser
145                 150                 155 agc aag gag ccc ggc ctg ttt gat gtg gtc atc att aac gac agc ctg        528
Ser Lys Glu Pro Gly Leu Phe Asp Val Val Ile Ile Asn Asp Ser Leu
            160                 165                 170 gac cag gcc tac gca gag ctg aag gag gcg ctc tct gag gaa atc aag        576
Asp Gln Ala Tyr Ala Glu Leu Lys Glu Ala Leu Ser Glu Glu Ile Lys
175                 180                 185                 190 aaa gct caa agg acc ggc gcc tgaggatcc                                  606
Lys Ala Gln Arg Thr Gly Ala
                195
```

<210> SEQ ID NO 49
<211> LENGTH: 197
<212> TYPE: PRT
<213> ORGANISM: Homo sapiens

<400> SEQUENCE: 49

```
Met Ala Gly Pro Arg Pro Val Val Leu Ser Gly Pro Ser Gly Ala Gly
1               5                   10                  15

Lys Ser Thr Leu Leu Lys Arg Leu Leu Gln Glu His Ser Gly Ile Phe
            20                  25                  30

Gly Phe Ser Val Ser His Thr Thr Arg Asn Pro Arg Pro Gly Glu Glu
        35                  40                  45

Asn Gly Lys Asp Tyr Tyr Phe Val Thr Arg Glu Val Met Gln Arg Asp
    50                  55                  60

Ile Ala Ala Gly Asp Phe Ile Glu His Ala Glu Phe Ser Gly Asn Leu
65                  70                  75                  80
```

```
Tyr Gly Thr Ser Lys Val Ala Val Gln Ala Val Gln Ala Met Asn Arg
            85                  90                  95

Ile Cys Val Leu Asp Val Asp Leu Gln Gly Val Arg Asn Ile Lys Ala
                100                 105                 110

Thr Asp Leu Arg Pro Ile Tyr Ile Ser Val Gln Pro Ser Leu His
            115                 120                 125

Val Leu Glu Gln Arg Leu Arg Gln Arg Asn Thr Glu Thr Glu Glu Ser
    130                 135                 140

Leu Val Lys Arg Leu Ala Ala Gln Ala Asp Met Glu Ser Ser Lys
145                 150                 155                 160

Glu Pro Gly Leu Phe Asp Val Val Ile Asn Asp Ser Leu Asp Gln
                165                 170                 175

Ala Tyr Ala Glu Leu Lys Glu Ala Leu Ser Glu Glu Ile Lys Lys Ala
            180                 185                 190

Gln Arg Thr Gly Ala
        195

<210> SEQ ID NO 50
<211> LENGTH: 660
<212> TYPE: DNA
<213> ORGANISM: Mus musculus
<220> FEATURE:
<221> NAME/KEY: CDS
<222> LOCATION: (25)..(618)

<400> SEQUENCE: 50
ctgggtcggg tccccgcgga cggc atg gca gga cct agg cca gta gtg ctg         51
                          Met Ala Gly Pro Arg Pro Val Val Leu
                           1               5 agc ggg ccg tca ggg gca ggg aag agc act ctg ctc aag aag ctg ttc        99
Ser Gly Pro Ser Gly Ala Gly Lys Ser Thr Leu Leu Lys Lys Leu Phe
 10                  15                  20                  25 cag gag cac agc agc atc ttc ggc ttc agt gtg tcc cat act aca agg       147
Gln Glu His Ser Ser Ile Phe Gly Phe Ser Val Ser His Thr Thr Arg
                 30                  35                  40 aac cca cga cct ggt gaa gaa gat ggc aaa gat tac tac ttt gtg acc       195
Asn Pro Arg Pro Gly Glu Glu Asp Gly Lys Asp Tyr Tyr Phe Val Thr
             45                  50                  55 agg gag atg atg cag cgt gat att gca gca ggg gac ttc att gag cat       243
Arg Glu Met Met Gln Arg Asp Ile Ala Ala Gly Asp Phe Ile Glu His
         60                  65                  70 gct gag ttc tca ggg aac ctg tac ggg aca agc aag gaa gct gtt cgg       291
Ala Glu Phe Ser Gly Asn Leu Tyr Gly Thr Ser Lys Glu Ala Val Arg
     75                  80                  85 gct gtg cag gcc atg aac cgc atc tgc gtg cta gat gtc gac cta caa       339
Ala Val Gln Ala Met Asn Arg Ile Cys Val Leu Asp Val Asp Leu Gln
 90                  95                 100                 105 ggt gtg cgc agc atc aag aag act gat ctg tgt ccc atc tac atc ttt       387
Gly Val Arg Ser Ile Lys Lys Thr Asp Leu Cys Pro Ile Tyr Ile Phe
                110                 115                 120 gtg cag cct ccc tcg ctg gac gtg ctg gag caa cga ctg cga ctg cgc       435
Val Gln Pro Pro Ser Leu Asp Val Leu Glu Gln Arg Leu Arg Leu Arg
            125                 130                 135 aac act gag act gag gag agt ctg gca aag cgg ctg gca gct gca cgg       483
Asn Thr Glu Thr Glu Glu Ser Leu Ala Lys Arg Leu Ala Ala Ala Arg
        140                 145                 150 aca gac atg gag agc agc aag gag cct ggc ttg ttt gac ctg gtg atc       531
Thr Asp Met Glu Ser Ser Lys Glu Pro Gly Leu Phe Asp Leu Val Ile
    155                 160                 165
```

```
atc aat gac gac ctg gat aaa gcc tat gca acc ctg aag cag gcg ctc    579
Ile Asn Asp Asp Leu Asp Lys Ala Tyr Ala Thr Leu Lys Gln Ala Leu
170             175                 180                 185 tct gag gaa atc aag aaa gca cag gga act ggc cac gcc tgaaggcctg    628
Ser Glu Glu Ile Lys Lys Ala Gln Gly Thr Gly His Ala
                190                 195 cttcattcca cagagtgatg tctgtggtct as                                660
```

<210> SEQ ID NO 51
<211> LENGTH: 198
<212> TYPE: PRT
<213> ORGANISM: Mus musculus

<400> SEQUENCE: 51

```
Met Ala Gly Pro Arg Pro Val Val Leu Ser Gly Pro Ser Gly Ala Gly
1               5                   10                  15

Lys Ser Thr Leu Leu Lys Lys Leu Phe Gln Glu His Ser Ser Ile Phe
                20                  25                  30

Gly Phe Ser Val Ser His Thr Thr Arg Asn Pro Arg Pro Gly Glu Glu
            35                  40                  45

Asp Gly Lys Asp Tyr Tyr Phe Val Thr Arg Glu Met Met Gln Arg Asp
        50                  55                  60

Ile Ala Ala Gly Asp Phe Ile Glu His Ala Glu Phe Ser Gly Asn Leu
65                  70                  75                  80

Tyr Gly Thr Ser Lys Glu Ala Val Arg Ala Val Gln Ala Met Asn Arg
                85                  90                  95

Ile Cys Val Leu Asp Val Asp Leu Gln Gly Val Arg Ser Ile Lys Lys
                100                 105                 110

Thr Asp Leu Cys Pro Ile Tyr Ile Phe Val Gln Pro Pro Ser Leu Asp
            115                 120                 125

Val Leu Glu Gln Arg Leu Arg Leu Arg Asn Thr Glu Thr Glu Glu Ser
        130                 135                 140

Leu Ala Lys Arg Leu Ala Ala Ala Arg Thr Asp Met Glu Ser Ser Lys
145                 150                 155                 160

Glu Pro Gly Leu Phe Asp Leu Val Ile Ile Asn Asp Asp Leu Asp Lys
                165                 170                 175

Ala Tyr Ala Thr Leu Lys Gln Ala Leu Ser Glu Glu Ile Lys Lys Ala
                180                 185                 190

Gln Gly Thr Gly His Ala
        195
```

<210> SEQ ID NO 52
<211> LENGTH: 16
<212> TYPE: DNA
<213> ORGANISM: Artificial Sequence
<220> FEATURE:
<223> OTHER INFORMATION: Primer

<400> SEQUENCE: 52

```
tcccccacct ccaggc                                                  16
```

<210> SEQ ID NO 53
<211> LENGTH: 18
<212> TYPE: DNA
<213> ORGANISM: Artificial Sequence
<220> FEATURE:
<223> OTHER INFORMATION: Primer

<400> SEQUENCE: 53

```
ctcagtgttg cccagtcg                                              18

<210> SEQ ID NO 54
<211> LENGTH: 18
<212> TYPE: DNA
<213> ORGANISM: Artificial Sequence
<220> FEATURE:
<223> OTHER INFORMATION: Primer

<400> SEQUENCE: 54
gccgaagatg ctgctgtg                                              18

<210> SEQ ID NO 55
<211> LENGTH: 33
<212> TYPE: DNA
<213> ORGANISM: Artificial Sequence
<220> FEATURE:
<223> OTHER INFORMATION: HSVTK Mutant
<220> FEATURE:
<221> NAME/KEY: CDS
<222> LOCATION: (1)..(33)

<400> SEQUENCE: 55 ccc atc gcc gcc ctc atc tgc tac ccg gcc gcg             33
Pro Ile Ala Ala Leu Ile Cys Tyr Pro Ala Ala
1               5                   10

<210> SEQ ID NO 56
<211> LENGTH: 11
<212> TYPE: PRT
<213> ORGANISM: Artificial Sequence
<220> FEATURE:
<223> OTHER INFORMATION: HSVTK Mutant

<400> SEQUENCE: 56

Pro Ile Ala Ala Leu Ile Cys Tyr Pro Ala Ala
1               5                   10

<210> SEQ ID NO 57
<211> LENGTH: 33
<212> TYPE: DNA
<213> ORGANISM: Artificial Sequence
<220> FEATURE:
<223> OTHER INFORMATION: HSVTK Mutant
<220> FEATURE:
<221> NAME/KEY: CDS
<222> LOCATION: (1)..(33)

<400> SEQUENCE: 57 cac atc tcg gcc ctc ctg tgc tac ccg gtc gcg             33
His Ile Ser Ala Leu Leu Cys Tyr Pro Val Ala
1               5                   10

<210> SEQ ID NO 58
<211> LENGTH: 11
<212> TYPE: PRT
<213> ORGANISM: Artificial Sequence
<220> FEATURE:
<223> OTHER INFORMATION: HSVTK Mutant

<400> SEQUENCE: 58

His Ile Ser Ala Leu Leu Cys Tyr Pro Val Ala
1               5                   10

<210> SEQ ID NO 59
<211> LENGTH: 72
<212> TYPE: DNA
<213> ORGANISM: Herpesviridae sp.
```

```
<220> FEATURE:
<221> NAME/KEY: CDS
<222> LOCATION: (1)..(72)

<400> SEQUENCE: 59 tca cat gcc ccg ccc ccg gcc ctc acc ctc atc ttc gac cgc cat ccc      48
Ser His Ala Pro Pro Pro Ala Leu Thr Leu Ile Phe Asp Arg His Pro
1               5                   10                  15 atc gcc gcc ctc ctg tgc tac ccg                                      72
Ile Ala Ala Leu Leu Cys Tyr Pro
            20

<210> SEQ ID NO 60
<211> LENGTH: 24
<212> TYPE: PRT
<213> ORGANISM: Herpesviridae sp.

<400> SEQUENCE: 60

Ser His Ala Pro Pro Pro Ala Leu Thr Leu Ile Phe Asp Arg His Pro
1               5                   10                  15

Ile Ala Ala Leu Leu Cys Tyr Pro
            20

<210> SEQ ID NO 61
<211> LENGTH: 72
<212> TYPE: DNA
<213> ORGANISM: Artificial Sequence
<220> FEATURE:
<223> OTHER INFORMATION: HSVTK Mutant

<400> SEQUENCE: 61
tcacatgtcc cgccccggc cctcaccatt ttggctgacc gccatcccat cgccgcatat      60
ttatgctacc cg                                                        72

<210> SEQ ID NO 62
<211> LENGTH: 72
<212> TYPE: DNA
<213> ORGANISM: Artificial Sequence
<220> FEATURE:
<223> OTHER INFORMATION: HSVTK Mutant

<400> SEQUENCE: 62
tcacatgccc cgccccctgc cctcaccgta ataacagacc gccatcccat cgcctgcctg      60
ctttgctacc cg                                                        72

<210> SEQ ID NO 63
<211> LENGTH: 72
<212> TYPE: DNA
<213> ORGANISM: Artificial Sequence
<220> FEATURE:
<223> OTHER INFORMATION: HSVTK Mutant

<400> SEQUENCE: 63
tcacatgccc cgccccggc cctcaccta ctactggacc gccatcccat cgccgtgatg       60
ctatgctacc cg                                                        72

<210> SEQ ID NO 64
<211> LENGTH: 72
<212> TYPE: DNA
<213> ORGANISM: Artificial Sequence
<220> FEATURE:
<223> OTHER INFORMATION: HSVTK Mutant

<400> SEQUENCE: 64
```

-continued

```
tcacatgccc cgcccccgtc cctcaccttg atcctggacc gccatcccat cgccagctac    60
tgttgctacc cg                                                        72

<210> SEQ ID NO 65
<211> LENGTH: 72
<212> TYPE: DNA
<213> ORGANISM: Artificial Sequence
<220> FEATURE:
<223> OTHER INFORMATION: HSVTK Mutant

<400> SEQUENCE: 65
tcacatgccc cgcccccggc cctcaccatg ttcatggacc gccatcccat cgcccataat    60
gtatgctacc cg                                                        72

<210> SEQ ID NO 66
<211> LENGTH: 66
<212> TYPE: DNA
<213> ORGANISM: Artificial Sequence
<220> FEATURE:
<223> OTHER INFORMATION: HSVTK Mutant

<400> SEQUENCE: 66
tcacatgccc cgccctcac catattgctt gaccgccatc ccatcgcaat ttacttatgc     60
tacccg                                                               66

<210> SEQ ID NO 67
<211> LENGTH: 69
<212> TYPE: DNA
<213> ORGANISM: Artificial Sequence
<220> FEATURE:
<223> OTHER INFORMATION: HSVTK Mutant

<400> SEQUENCE: 67
tcacatgccc cgccggccct caccttttat tatgaccgcc atcccatcgc ccctttttgtt   60 tgctacccg                                                            69

<210> SEQ ID NO 68
<211> LENGTH: 72
<212> TYPE: DNA
<213> ORGANISM: Artificial Sequence
<220> FEATURE:
<223> OTHER INFORMATION: HSVTK Mutant

<400> SEQUENCE: 68
tcacatgccc cgcccccggc cctcaccttg ttcctcgacc gccatcccat cgccctcatg    60
tgttgctacc cg                                                        72

<210> SEQ ID NO 69
<211> LENGTH: 69
<212> TYPE: DNA
<213> ORGANISM: Artificial Sequence
<220> FEATURE:
<223> OTHER INFORMATION: HSVTK Mutant

<400> SEQUENCE: 69
tcacatgccc cgcccccct caccctcgta ttagaccgtc atcccatcgc ctactatcta    60
tgctaccct                                                            69

<210> SEQ ID NO 70
<211> LENGTH: 69
<212> TYPE: DNA
```

-continued

<213> ORGANISM: Artificial Sequence
<220> FEATURE:
<223> OTHER INFORMATION: HSVTK Mutant

<400> SEQUENCE: 70
tcacatgccc cgccggccct cacctgtttt ctcgaccgcc atcccatcgc ctattatctt    60
tgctacccg    69

<210> SEQ ID NO 71
<211> LENGTH: 15
<212> TYPE: PRT
<213> ORGANISM: Herpesviridae sp.

<400> SEQUENCE: 71

Leu Ile Phe Asp Arg His Pro Ile Ala Ala Leu Leu Cys Tyr Pro
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 72

Leu Val Phe Asp Arg His Pro Ile Ala Thr Leu Leu Cys Tyr Pro
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 73

Phe Ile Phe Asp Arg His Pro Ile Ala Tyr Tyr Ile Cys Tyr Pro
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 74

Val Leu Ser Asp Arg His Pro Ile Ala Arg Ile Tyr Cys Tyr Pro
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 75

Leu Ile Leu Asp Arg His Pro Ile Ala Asn Phe Ile Cys Tyr Pro
1               5                   10                  15

<210> SEQ ID NO 76
<211> LENGTH: 15
<212> TYPE: PRT
<213> ORGANISM: Artificial Sequence
<220> FEATURE:

<223> OTHER INFORMATION: HSVTK Mutant

<400> SEQUENCE: 76

Thr Phe Tyr Asp Arg His Pro Ile Ala Trp Met Phe Cys Tyr Pro
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 77

Val Val Cys Asp Arg His Pro Ile Ala Cys Thr Leu Cys Tyr Pro
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 78

Leu Phe Ala Asp Arg His Pro Ile Ala Thr Leu Leu Cys Tyr Pro
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 79

Val Phe Ser Asp Arg His Pro Ile Ala Leu Leu Leu Cys Tyr Pro
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 80

Leu Cys Phe Asp Arg His Pro Ile Ala Tyr Cys Ile Cys Tyr Pro
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 81

Ile Ile Ala Asp Arg His Pro Ile Ala Leu Leu Val Cys Tyr Pro
1 5 10 15

<210> SEQ ID NO 82
<211> LENGTH: 15
<212> TYPE: PRT
<213> ORGANISM: Artificial Sequence
<220> FEATURE:
<223> OTHER INFORMATION: HSVTK Mutant

```
<400> SEQUENCE: 82

Leu Ile Leu Asp Arg His Pro Ile Ala Val Ser Leu Cys Tyr Pro
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 83

Leu Leu His Asp Arg His Pro Ile Ala Val Cys Val Cys Tyr Pro
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 84

Leu Leu Ser Asp Arg His Pro Ile Ala Tyr His Leu Cys Tyr Pro
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 85

Phe Leu Val Asp Arg His Pro Ile Ala Trp Asn Leu Cys Tyr Pro
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 86

Thr Val Phe Asp Arg His Pro Ile Ala Ser Thr Phe Cys Tyr Pro
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 87

Leu Thr Phe Asp Arg His Pro Ile Ala Gly Thr Leu Cys Tyr Pro
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: HSVTK Mutant
```

```
<400> SEQUENCE: 88

Leu Phe Ile Asp Arg His Pro Ile Ala Thr Ile Leu Cys Tyr Pro
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 89

Val Ala Ala Asp Arg His Pro Ile Ala Phe Ser Tyr Cys Tyr Pro
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 90

Pro Thr Gln Asp Arg His Pro Ile Ala Ser Asp Pro Cys Tyr Pro
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 91

Arg Ala Phe Asp Arg His Pro Ile Gly Gln Thr Ser Cys Tyr Pro
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 92

Asp Gly Val Asp Arg His Pro Ile Ala Cys Arg His Cys Tyr Pro
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 93

Asp Asn Asn Asp Arg His Pro Ile Ala Gln Ser Pro Cys Tyr Pro
1               5                   10                  15

<210> SEQ ID NO 94
<211> LENGTH: 11
<212> TYPE: PRT
<213> ORGANISM: Artificial Sequence
<220> FEATURE:
<223> OTHER INFORMATION: HSVTK Mutant

<400> SEQUENCE: 94
```

```
Ile Leu Asn Asp Arg His Pro Ile Ala Arg Thr
1               5                   10
```

<210> SEQ ID NO 95
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 95

```
Phe Leu Asp Asp Arg His Pro Ile Ala Pro Leu Leu Cys Tyr Pro
1               5                   10                  15
```

<210> SEQ ID NO 96
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 96

```
Tyr Tyr Val Asp Arg His Pro Ile Ala Val Ser Leu Cys Tyr Pro
1               5                   10                  15
```

<210> SEQ ID NO 97
<211> LENGTH: 12
<212> TYPE: PRT
<213> ORGANISM: Artificial Sequence
<220> FEATURE:
<223> OTHER INFORMATION: HSVTK Mutant

<400> SEQUENCE: 97

```
Asp Arg His Pro Ile Ala Leu Arg Ser Cys Asn Pro
1               5                   10
```

<210> SEQ ID NO 98
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 98

```
Leu Asn Pro Asp Arg His Pro Ile Ala Cys Asp Cys Cys Tyr Pro
1               5                   10                  15
```

<210> SEQ ID NO 99
<211> LENGTH: 12
<212> TYPE: PRT
<213> ORGANISM: Artificial Sequence
<220> FEATURE:
<223> OTHER INFORMATION: HSVTK Mutant

<400> SEQUENCE: 99

```
Ser Trp Gly Asp Arg His Pro Ile Glu Lys Phe Ile
1               5                   10
```

<210> SEQ ID NO 100
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 100

Tyr Gly Ser Asp Arg His Pro Ile Ala Ile Cys Pro Cys Tyr Pro
1               5                   10                  15

<210> SEQ ID NO 101
<211> LENGTH: 8
<212> TYPE: PRT
<213> ORGANISM: Artificial Sequence
<220> FEATURE:
<223> OTHER INFORMATION: HSVTK Mutant

<400> SEQUENCE: 101

Asp Arg His Pro Ile Ala Ile Ile
1               5

<210> SEQ ID NO 102
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 102

Tyr Tyr Asn Asp Arg His Pro Ile Ala Gly Ser Pro Cys Tyr Pro
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 103

Trp Gly Arg Asp Arg His Pro Ile Ala Asn Leu Leu Cys Tyr Pro
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: HSVTK Mutant

<400> SEQUENCE: 104

Arg Leu Pro Asp Arg His Pro Ile Ala Asn Glu Ala Cys Tyr Pro
1               5                   10                  15

<210> SEQ ID NO 105
<211> LENGTH: 12
<212> TYPE: PRT
<213> ORGANISM: Herpesviridae sp.

<400> SEQUENCE: 105

Leu Ile Phe Asp Arg His Pro Ile Ala Ala Leu Leu
1               5                   10

<210> SEQ ID NO 106
<211> LENGTH: 12
<212> TYPE: PRT
<213> ORGANISM: Artificial Sequence
<220> FEATURE:
<223> OTHER INFORMATION: HSVTK Mutant

<400> SEQUENCE: 106

Leu Phe Leu Asp Arg His Pro Ile Ala Phe Asn Leu
1               5                   10

```
<210> SEQ ID NO 107
<211> LENGTH: 12
<212> TYPE: PRT
<213> ORGANISM: Artificial Sequence
<220> FEATURE:
<223> OTHER INFORMATION: HSVTK Mutant

<400> SEQUENCE: 107

Leu Phe Ala Asp Arg His Pro Ile Ala Phe Leu Leu
1               5                   10

<210> SEQ ID NO 108
<211> LENGTH: 12
<212> TYPE: PRT
<213> ORGANISM: Artificial Sequence
<220> FEATURE:
<223> OTHER INFORMATION: HSVTK Mutant

<400> SEQUENCE: 108

Ile Phe Leu Asp Arg His Pro Ile Ala Phe Met Leu
1               5                   10

<210> SEQ ID NO 109
<211> LENGTH: 12
<212> TYPE: PRT
<213> ORGANISM: Artificial Sequence
<220> FEATURE:
<223> OTHER INFORMATION: HSVTK Mutant

<400> SEQUENCE: 109

Ile Leu Leu Asp Arg His Pro Ile Ala Tyr Leu Leu
1               5                   10

<210> SEQ ID NO 110
<211> LENGTH: 12
<212> TYPE: PRT
<213> ORGANISM: Artificial Sequence
<220> FEATURE:
<223> OTHER INFORMATION: HSVTK Mutant

<400> SEQUENCE: 110

Leu Phe Ala Asp Arg His Pro Ile Ala Tyr Tyr Leu
1               5                   10

<210> SEQ ID NO 111
<211> LENGTH: 12
<212> TYPE: PRT
<213> ORGANISM: Artificial Sequence
<220> FEATURE:
<223> OTHER INFORMATION: HSVTK Mutant

<400> SEQUENCE: 111

Leu Phe Val Asp Arg His Pro Ile Ala Val Met Leu
1               5                   10

<210> SEQ ID NO 112
<211> LENGTH: 12
<212> TYPE: PRT
<213> ORGANISM: Artificial Sequence
<220> FEATURE:
<223> OTHER INFORMATION: HSVTK Mutant

<400> SEQUENCE: 112

Ile Phe Val Asp Arg His Pro Ile Ala Phe Tyr Leu
1               5                   10
```

<210> SEQ ID NO 113
<211> LENGTH: 21
<212> TYPE: DNA
<213> ORGANISM: Artificial Sequence
<220> FEATURE:
<223> OTHER INFORMATION: Primer

<400> SEQUENCE: 113
gtctcggagg cgcccagcac c                                      21

<210> SEQ ID NO 114
<211> LENGTH: 59
<212> TYPE: DNA
<213> ORGANISM: Artificial Sequence
<220> FEATURE:
<223> OTHER INFORMATION: Oligonucleotide used to generate TK mutants

<400> SEQUENCE: 114
aggctgggag ctcacatgcc ccgcccccgg ccctcaccac tcttgcgcct cgaccgcca    59

<210> SEQ ID NO 115
<211> LENGTH: 54
<212> TYPE: DNA
<213> ORGANISM: Artificial Sequence
<220> FEATURE:
<223> OTHER INFORMATION: Oligonucleotide used to generate TK mutants

<400> SEQUENCE: 115
ataaggtacc gcgcggccgg gtagcacaga catgtacagg cgatgggatg gcgg         54

<210> SEQ ID NO 116
<211> LENGTH: 55
<212> TYPE: DNA
<213> ORGANISM: Artificial Sequence
<220> FEATURE:
<223> OTHER INFORMATION: Oligonucleotide used to generate TK mutants

<400> SEQUENCE: 116
cgcctcgacc agggtgagat atcggccggg gacgcggcgg tggtaatgac aagcg        55

<210> SEQ ID NO 117
<211> LENGTH: 58
<212> TYPE: DNA
<213> ORGANISM: Artificial Sequence
<220> FEATURE:
<223> OTHER INFORMATION: Oligonucleotide used to generate TK mutants

<400> SEQUENCE: 117
gaacggcgtc ggtcacggca taaggcatgc ccattgttat ctgggcgctt gtcattac     58

<210> SEQ ID NO 118
<211> LENGTH: 60
<212> TYPE: DNA
<213> ORGANISM: Artificial Sequence
<220> FEATURE:
<223> OTHER INFORMATION: Oligonucleotide used to generate TK mutants

<400> SEQUENCE: 118
ggcgcctccg agacaatcgc gaacatctac accacacaac accgcctcga ccagggtgag   60

<210> SEQ ID NO 119
<211> LENGTH: 59
<212> TYPE: DNA
<213> ORGANISM: Artificial Sequence
<220> FEATURE:
<223> OTHER INFORMATION: Oligonucleotide used to generate TK mutants

```
<400> SEQUENCE: 119
tcgactgagc tcccagcctc cccccgata tgaggagcca gaacggcgtc ggtcacggc       59

<210> SEQ ID NO 120
<211> LENGTH: 24
<212> TYPE: DNA
<213> ORGANISM: Artificial Sequence
<220> FEATURE:
<223> OTHER INFORMATION: Oligonucleotide used to generate TK mutants

<400> SEQUENCE: 120
gcagctggcg cctccgagac aatc                                            24

<210> SEQ ID NO 121
<211> LENGTH: 19
<212> TYPE: DNA
<213> ORGANISM: Artificial Sequence
<220> FEATURE:
<223> OTHER INFORMATION: Oligonucleotide used to generate TK mutants

<400> SEQUENCE: 121
tcgactgagc tcccagcct                                                  19

<210> SEQ ID NO 122
<211> LENGTH: 24
<212> TYPE: PRT
<213> ORGANISM: Artificial Sequence
<220> FEATURE:
<223> OTHER INFORMATION: HSVTK Mutant

<400> SEQUENCE: 122

Ser His Ala Pro Pro Pro Ala Leu Thr Ile Leu Ala Asp Arg His Pro
1               5                   10                  15

Ile Ala Tyr Phe Leu Cys Tyr Pro
            20

<210> SEQ ID NO 123
<211> LENGTH: 24
<212> TYPE: PRT
<213> ORGANISM: Artificial Sequence
<220> FEATURE:
<223> OTHER INFORMATION: HSVTK Mutant

<400> SEQUENCE: 123

Ser His Ala Pro Pro Pro Ala Leu Thr Val Ile Thr Asp Arg His Pro
1               5                   10                  15

Ile Ala Cys Leu Leu Cys Tyr Pro
            20

<210> SEQ ID NO 124
<211> LENGTH: 24
<212> TYPE: PRT
<213> ORGANISM: Artificial Sequence
<220> FEATURE:
<223> OTHER INFORMATION: HSVTK Mutant

<400> SEQUENCE: 124

Ser His Ala Pro Pro Pro Ala Leu Thr Leu Leu Leu Asp Arg His Pro
1               5                   10                  15

Ile Ala Val Met Leu Cys Tyr Pro
            20

<210> SEQ ID NO 125
<211> LENGTH: 24
```

```
<212> TYPE: PRT
<213> ORGANISM: Artificial Sequence
<220> FEATURE:
<223> OTHER INFORMATION: HSVTK Mutant

<400> SEQUENCE: 125

Ser His Ala Pro Pro Pro Ala Leu Thr Leu Ile Leu Asp Arg His Pro
1               5                   10                  15

Ile Ala Ser Tyr Cys Cys Tyr Pro
            20

<210> SEQ ID NO 126
<211> LENGTH: 24
<212> TYPE: PRT
<213> ORGANISM: Artificial Sequence
<220> FEATURE:
<223> OTHER INFORMATION: HSVTK Mutant

<400> SEQUENCE: 126

Ser His Ala Pro Pro Pro Ala Leu Thr Met Phe Met Asp Arg His Pro
1               5                   10                  15

Ile Ala His Asn Val Cys Tyr Pro
            20

<210> SEQ ID NO 127
<211> LENGTH: 24
<212> TYPE: PRT
<213> ORGANISM: Artificial Sequence
<220> FEATURE:
<223> OTHER INFORMATION: HSVTK Mutant

<400> SEQUENCE: 127

Ser His Ala Pro Pro Pro Ala Leu Thr Ile Leu Leu Asp Arg His Pro
1               5                   10                  15

Ile Ala Ile Tyr Leu Cys Tyr Pro
            20

<210> SEQ ID NO 128
<211> LENGTH: 24
<212> TYPE: PRT
<213> ORGANISM: Artificial Sequence
<220> FEATURE:
<223> OTHER INFORMATION: HSVTK Mutant

<400> SEQUENCE: 128

Ser His Ala Pro Pro Pro Ala Leu Thr Phe Tyr Tyr Asp Arg His Pro
1               5                   10                  15

Ile Ala Pro Phe Val Cys Tyr Pro
            20

<210> SEQ ID NO 129
<211> LENGTH: 24
<212> TYPE: PRT
<213> ORGANISM: Artificial Sequence
<220> FEATURE:
<223> OTHER INFORMATION: HSVTK Mutant

<400> SEQUENCE: 129

Ser His Ala Pro Pro Pro Ala Leu Thr Leu Phe Leu Asp Arg His Pro
1               5                   10                  15

Ile Ala Leu Met Cys Cys Tyr Pro
            20

<210> SEQ ID NO 130
```

```
<211> LENGTH: 24
<212> TYPE: PRT
<213> ORGANISM: Artificial Sequence
<220> FEATURE:
<223> OTHER INFORMATION: HSVTK Mutant

<400> SEQUENCE: 130

Ser His Ala Pro Pro Pro Ala Leu Thr Leu Val Leu Asp Arg His Pro
1               5                   10                  15

Ile Ala Tyr Tyr Leu Cys Tyr Pro
            20

<210> SEQ ID NO 131
<211> LENGTH: 24
<212> TYPE: PRT
<213> ORGANISM: Artificial Sequence
<220> FEATURE:
<223> OTHER INFORMATION: HSVTK Mutant

<400> SEQUENCE: 131

Ser His Ala Pro Pro Pro Ala Leu Thr Cys Phe Leu Asp Arg His Pro
1               5                   10                  15

Ile Ala Tyr Tyr Leu Cys Tyr Pro
            20

<210> SEQ ID NO 132
<211> LENGTH: 24
<212> TYPE: PRT
<213> ORGANISM: Artificial Sequence
<220> FEATURE:
<223> OTHER INFORMATION: HSVTK Mutant
<220> FEATURE:
<221> NAME/KEY: VARIANT
<222> LOCATION: (10)..(10)
<223> OTHER INFORMATION: xaa = Ile or Leu
<220> FEATURE:
<221> NAME/KEY: VARIANT
<222> LOCATION: (11)..(11)
<223> OTHER INFORMATION: xaa = Ile or Leu or Phe
<220> FEATURE:
<221> NAME/KEY: VARIANT
<222> LOCATION: (12)..(12)
<223> OTHER INFORMATION: xaa = Phe or Ala or Val or Pro or Leu
<220> FEATURE:
<221> NAME/KEY: VARIANT
<222> LOCATION: (19)..(19)
<223> OTHER INFORMATION: xaa = Ala or Asp or Tyr or Val or Phe
<220> FEATURE:
<221> NAME/KEY: VARIANT
<222> LOCATION: (20)..(20)
<223> OTHER INFORMATION: xaa = Leu or Phe or Tyr or Ile or Met or Asn
      or Lys

<400> SEQUENCE: 132

Ser His Ala Pro Pro Pro Ala Leu Thr Xaa Xaa Xaa Asp Arg His Pro
1               5                   10                  15

Ile Ala Xaa Xaa Leu Cys Tyr Pro
            20

<210> SEQ ID NO 133
<211> LENGTH: 11
<212> TYPE: PRT
<213> ORGANISM: Artificial Sequence
<220> FEATURE:
<223> OTHER INFORMATION: HSVTK Mutant
<220> FEATURE:
<221> NAME/KEY: VARIANT
<222> LOCATION: (1)..(1)
<223> OTHER INFORMATION: xaa = Ile or Leu
<220> FEATURE:
```

```
<221> NAME/KEY: VARIANT
<222> LOCATION: (2)..(2)
<223> OTHER INFORMATION: xaa = Ile or Leu or Phe
<220> FEATURE:
<221> NAME/KEY: VARIANT
<222> LOCATION: (3)..(3)
<223> OTHER INFORMATION: xaa = Phe or Ala or Val or Pro or Leu
<220> FEATURE:
<221> NAME/KEY: VARIANT
<222> LOCATION: (10)..(10)
<223> OTHER INFORMATION: xaa = Ala or Asp or Tyr or Val or Phe
<220> FEATURE:
<221> NAME/KEY: VARIANT
<222> LOCATION: (11)..(11)
<223> OTHER INFORMATION: xaa = Leu or Phe or Tyr or Ile or Met or Asn
      or Lys

<400> SEQUENCE: 133

Xaa Xaa Xaa Asp Arg His Pro Ile Ala Xaa Xaa
1               5                   10

<210> SEQ ID NO 134
<211> LENGTH: 376
<212> TYPE: PRT
<213> ORGANISM: Herpesviridae sp.

<400> SEQUENCE: 134

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
```

-continued

```
                260                 265                 270
Glu Pro Gln Ser Asn Ala Gly Pro Arg Pro His Ile Gly Asp Thr Leu
            275                 280                 285
Phe Thr Leu Phe Arg Ala Pro Glu Leu Leu Ala Pro Asn Gly Asp Leu
        290                 295                 300
Tyr Asn Val Phe Ala Trp Ala Leu Asp Val Leu Ala Lys Arg Leu Arg
305                 310                 315                 320
Ser Met His Val Phe Ile Leu Asp Tyr Asp Gln Ser Pro Ala Gly Cys
                325                 330                 335
Arg Asp Ala Leu Leu Gln Leu Thr Ser Gly Met Val Gln Thr His Val
            340                 345                 350
Thr Thr Pro Gly Ser Ile Pro Thr Ile Cys Asp Leu Ala Arg Thr Phe
        355                 360                 365
Ala Arg Glu Met Gly Glu Ala Asn
        370                 375

<210> SEQ ID NO 135
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 135

Met Ala Ser Tyr Pro Gly His Gln His Ala Ser Ala Phe Asp Gln Ala
1               5                   10                  15
Ala Arg Ser Arg Gly His Ser Asn Arg Arg Thr Ala Leu Arg Pro Arg
            20                  25                  30
Arg Gln Gln Glu Ala Thr Glu Val Arg Leu Glu Gln Lys Met Pro Thr
        35                  40                  45
Leu Leu Arg Val Tyr Ile Asp Gly Pro His Gly Met Gly Lys Thr Thr
    50                  55                  60
Thr Thr Gln Leu Leu Val Ala Leu Gly Ser Arg Asp Asp Ile Val Tyr
65                  70                  75                  80
Val Pro Glu Pro Met Thr Tyr Trp Gln Val Leu Gly Ala Ser Glu Thr
                85                  90                  95
Ile Ala Asn Ile Tyr Thr Thr Gln His Arg Leu Asp Gln Gly Glu Ile
            100                 105                 110
Ser Ala Gly Asp Ala Ala Val Val Met Thr Ser Ala Gln Ile Thr Met
        115                 120                 125
Gly Met Pro Tyr Ala Val Thr Asp Ala Val Leu Ala Pro His Ile Gly
    130                 135                 140
Gly Glu Ala Gly Ser Ser His Val Pro Pro Ala Leu Thr Ile Leu
145                 150                 155                 160
Ala Asp Arg His Pro Ile Ala Tyr Phe Leu Cys Tyr Pro Ala Ala Arg
                165                 170                 175
Tyr Leu Met Gly Ser Met Thr Pro Gln Ala Val Leu Ala Phe Val Ala
            180                 185                 190
Leu Ile Pro Pro Thr Leu Pro Gly Thr Asn Ile Val Leu Gly Ala Leu
        195                 200                 205
Pro Glu Asp Arg His Ile Asp Arg Leu Ala Lys Arg Gln Arg Pro Gly
    210                 215                 220
Glu Arg Leu Asp Leu Ala Met Leu Ala Ala Ile Arg Arg Val Tyr Gly
225                 230                 235                 240
Leu Leu Ala Asn Thr Val Arg Tyr Leu Gln Cys Gly Gly Ser Trp Arg
```

-continued

```
                245                 250                 255
Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
            275                 280                 285

Phe Thr Leu Phe Arg Ala Pro Glu Leu Leu Ala Pro Asn Gly Asp Leu
            290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
            355                 360                 365

Ala Arg Glu Met Gly Glu Ala Asn
            370                 375

<210> SEQ ID NO 136
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 136

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ser Leu Thr Leu Ile
145                 150                 155                 160

Leu Asp Arg His Pro Ile Ala Ser Tyr Cys Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Ala Leu Ala Met Leu Ala Ala Ile Arg Arg Val Tyr Gly
```

```
                 225                 230                 235                 240
Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 137
<211> LENGTH: 374
<212> TYPE: PRT
<213> ORGANISM: Artificial Sequence
<220> FEATURE:
<223> OTHER INFORMATION: HSVTK Mutant

<400> SEQUENCE: 137

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Leu Thr Ile Leu Leu Asp
145                 150                 155                 160

Arg His Pro Ile Ala Ile Tyr Leu Cys Tyr Pro Ala Ala Arg Tyr Leu
                165                 170                 175

Met Gly Ser Met Thr Pro Gln Ala Val Leu Ala Phe Val Ala Leu Ile
            180                 185                 190

Pro Pro Thr Leu Pro Gly Thr Asn Ile Val Leu Gly Ala Leu Pro Glu
        195                 200                 205

Asp Arg His Ile Asp Arg Leu Ala Lys Arg Gln Arg Pro Gly Glu Arg
```

-continued

```
            210                 215                 220
Leu Asp Leu Ala Met Leu Ala Ala Ile Arg Arg Val Tyr Gly Leu Leu
225                 230                 235                 240

Ala Asn Thr Val Arg Tyr Leu Gln Cys Gly Gly Ser Trp Arg Glu Asp
                245                 250                 255

Trp Gly Gln Leu Ser Gly Thr Ala Val Pro Pro Gln Gly Ala Glu Pro
            260                 265                 270

Gln Ser Asn Ala Gly Pro Arg Pro His Ile Gly Asp Thr Leu Phe Thr
                275                 280                 285

Leu Phe Arg Ala Pro Glu Leu Leu Ala Pro Asn Gly Asp Leu Tyr Asn
            290                 295                 300

Val Phe Ala Trp Ala Leu Asp Val Leu Ala Lys Arg Leu Arg Ser Met
305                 310                 315                 320

His Val Phe Ile Leu Asp Tyr Asp Gln Ser Pro Ala Gly Cys Arg Asp
                325                 330                 335

Ala Leu Leu Gln Leu Thr Ser Gly Met Val Gln Thr His Val Thr Thr
            340                 345                 350

Pro Gly Ser Ile Pro Thr Ile Cys Asp Leu Ala Arg Thr Phe Ala Arg
                355                 360                 365

Glu Met Gly Glu Ala Asn
        370

<210> SEQ ID NO 138
<211> LENGTH: 375
<212> TYPE: PRT
<213> ORGANISM: Artificial Sequence
<220> FEATURE:
<223> OTHER INFORMATION: HSVTK Mutant

<400> SEQUENCE: 138

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
                20                  25                  30

Arg Gln Gln Glu Ala Thr Glu Val Arg Leu Glu Gln Lys Met Pro Thr
            35                  40                  45

Leu Leu Arg Val Tyr Ile Asp Gly Pro His Gly Met Gly Lys Thr Thr
50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
                100                 105                 110

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Ile Gly
        130                 135                 140

Gly Glu Ala Gly Ser Ser His Ala Pro Pro Ala Leu Thr Phe Tyr Tyr
145                 150                 155                 160

Asp Arg His Pro Ile Ala Pro Phe Val Cys Tyr Pro Ala Ala Arg Tyr
                165                 170                 175

Leu Met Gly Ser Met Thr Pro Gln Ala Val Leu Ala Phe Val Ala Leu
            180                 185                 190

Ile Pro Pro Thr Leu Pro Gly Thr Asn Ile Val Leu Gly Ala Leu Pro
```

-continued

```
                195                 200                 205
Glu Asp Arg His Ile Asp Arg Leu Ala Lys Arg Gln Arg Pro Gly Glu
    210                 215                 220

Arg Leu Asp Leu Ala Met Leu Ala Ala Ile Arg Arg Val Tyr Gly Leu
225                 230                 235                 240

Leu Ala Asn Thr Val Arg Tyr Leu Gln Cys Gly Gly Ser Trp Arg Glu
                245                 250                 255

Asp Trp Gly Gln Leu Ser Gly Thr Ala Val Pro Pro Gln Gly Ala Glu
            260                 265                 270

Pro Gln Ser Asn Ala Gly Pro Arg Pro His Ile Gly Asp Thr Leu Phe
        275                 280                 285

Thr Leu Phe Arg Ala Pro Glu Leu Leu Ala Pro Asn Gly Asp Leu Tyr
    290                 295                 300

Asn Val Phe Ala Trp Ala Leu Asp Val Leu Ala Lys Arg Leu Arg Ser
305                 310                 315                 320

Met His Val Phe Ile Leu Asp Tyr Asp Gln Ser Pro Ala Gly Cys Arg
                325                 330                 335

Asp Ala Leu Leu Gln Leu Thr Ser Gly Met Val Gln Thr His Val Thr
            340                 345                 350

Thr Pro Gly Ser Ile Pro Thr Ile Cys Asp Leu Ala Arg Thr Phe Ala
        355                 360                 365

Arg Glu Met Gly Glu Ala Asn
    370                 375

<210> SEQ ID NO 139
<211> LENGTH: 375
<212> TYPE: PRT
<213> ORGANISM: Artificial Sequence
<220> FEATURE:
<223> OTHER INFORMATION: HSVTK Mutant

<400> SEQUENCE: 139

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
                20                  25                  30

Arg Gln Gln Glu Ala Thr Glu Val Arg Leu Glu Gln Lys Met Pro Thr
            35                  40                  45

Leu Leu Arg Val Tyr Ile Asp Gly Pro His Gly Met Gly Lys Thr Thr
        50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Leu Thr Leu Val Leu Leu
145                 150                 155                 160

Asp Arg His Pro Ile Ala Tyr Tyr Leu Cys Tyr Pro Ala Ala Arg Tyr
                165                 170                 175

Leu Met Gly Ser Met Thr Pro Gln Ala Val Leu Ala Phe Val Ala Leu
```

-continued

```
                 180                 185                 190
Ile Pro Pro Thr Leu Pro Gly Thr Asn Ile Val Leu Gly Ala Leu Pro
            195                 200                 205

Glu Asp Arg His Ile Asp Arg Leu Ala Lys Arg Gln Arg Pro Gly Glu
        210                 215                 220

Arg Leu Asp Leu Ala Met Leu Ala Ala Ile Arg Arg Val Tyr Gly Leu
225                 230                 235                 240

Leu Ala Asn Thr Val Arg Tyr Leu Gln Cys Gly Gly Ser Trp Arg Glu
                245                 250                 255

Asp Trp Gly Gln Leu Ser Gly Thr Ala Val Pro Pro Gln Gly Ala Glu
            260                 265                 270

Pro Gln Ser Asn Ala Gly Pro Arg Pro His Ile Gly Asp Thr Leu Phe
        275                 280                 285

Thr Leu Phe Arg Ala Pro Glu Leu Leu Ala Pro Asn Gly Asp Leu Tyr
290                 295                 300

Asn Val Phe Ala Trp Ala Leu Asp Val Leu Ala Lys Arg Leu Arg Ser
305                 310                 315                 320

Met His Val Phe Ile Leu Asp Tyr Asp Gln Ser Pro Ala Gly Cys Arg
                325                 330                 335

Asp Ala Leu Leu Gln Leu Thr Ser Gly Met Val Gln Thr His Val Thr
            340                 345                 350

Thr Pro Gly Ser Ile Pro Thr Ile Cys Asp Leu Ala Arg Thr Phe Ala
        355                 360                 365

Arg Glu Met Gly Glu Ala Asn
        370                 375

<210> SEQ ID NO 140
<211> LENGTH: 375
<212> TYPE: PRT
<213> ORGANISM: Artificial Sequence
<220> FEATURE:
<223> OTHER INFORMATION: HSVTK Mutant

<400> SEQUENCE: 140

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Cys Phe Leu
145                 150                 155                 160

Asp Arg His Pro Ile Ala Tyr Tyr Leu Cys Tyr Pro Ala Ala Arg Tyr
```

```
                        165                 170                 175
Leu Met Gly Ser Met Thr Pro Gln Ala Val Leu Ala Phe Val Ala Leu
            180                 185                 190

Ile Pro Pro Thr Leu Pro Gly Thr Asn Ile Val Leu Gly Ala Leu Pro
        195                 200                 205

Glu Asp Arg His Ile Asp Arg Leu Ala Lys Arg Gln Arg Pro Gly Glu
    210                 215                 220

Arg Leu Asp Leu Ala Met Leu Ala Ala Ile Arg Arg Val Tyr Gly Leu
225                 230                 235                 240

Leu Ala Asn Thr Val Arg Tyr Leu Gln Cys Gly Gly Ser Trp Arg Glu
                245                 250                 255

Asp Trp Gly Gln Leu Ser Gly Thr Ala Val Pro Pro Gln Gly Ala Glu
            260                 265                 270

Pro Gln Ser Asn Ala Gly Pro Arg Pro His Ile Gly Asp Thr Leu Phe
        275                 280                 285

Thr Leu Phe Arg Ala Pro Glu Leu Leu Ala Pro Asn Gly Asp Leu Tyr
    290                 295                 300

Asn Val Phe Ala Trp Ala Leu Asp Val Leu Ala Lys Arg Leu Arg Ser
305                 310                 315                 320

Met His Val Phe Ile Leu Asp Tyr Asp Gln Ser Pro Ala Gly Cys Arg
                325                 330                 335

Asp Ala Leu Leu Gln Leu Thr Ser Gly Met Val Gln Thr His Val Thr
            340                 345                 350

Thr Pro Gly Ser Ile Pro Thr Ile Cys Asp Leu Ala Arg Thr Phe Ala
        355                 360                 365

Arg Glu Met Gly Glu Ala Asn
    370                 375

<210> SEQ ID NO 141
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 141

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Ala Leu Thr Leu Ile
```

```
                     145                 150                 155                 160
Val Asp Arg His Pro Ile Ala Ala Leu Leu Cys Tyr Pro Ala Ala Arg
                 165                 170                 175

Tyr Leu Met Gly Ser Met Thr Pro Gln Ala Val Leu Ala Phe Val Ala
             180                 185                 190

Leu Ile Pro Pro Thr Leu Pro Gly Thr Asn Ile Val Leu Gly Ala Leu
         195                 200                 205

Pro Glu Asp Arg His Ile Asp Arg Leu Ala Lys Arg Gln Arg Pro Gly
     210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                 245                 250                 255

Glu Asp Trp Gly Gln Leu Ser Gly Thr Ala Val Pro Pro Gln Gly Ala
             260                 265                 270

Glu Pro Gln Ser Asn Ala Gly Pro Arg Pro His Ile Gly Asp Thr Leu
         275                 280                 285

Phe Thr Leu Phe Arg Ala Pro Glu Leu Leu Ala Pro Asn Gly Asp Leu
     290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                 325                 330                 335

Arg Asp Ala Leu Leu Gln Leu Thr Ser Gly Met Val Gln Thr His Val
             340                 345                 350

Thr Thr Pro Gly Ser Ile Pro Thr Ile Cys Asp Leu Ala Arg Thr Phe
         355                 360                 365

Ala Arg Glu Met Gly Glu Ala Asn
     370                 375

<210> SEQ ID NO 142
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 142

Met Ala Ser Tyr Pro Gly His Gln His Ala Ser Ala Phe Asp Gln Ala
1               5                  10                  15

Ala Arg Ser Arg Gly His Ser Asn Arg Arg Thr Ala Leu Arg Pro Arg
             20                  25                  30

Arg Gln Gln Glu Ala Thr Glu Val Arg Leu Glu Gln Lys Met Pro Thr
         35                  40                  45

Leu Leu Arg Val Tyr Ile Asp Gly Pro His Gly Met Gly Lys Thr Thr
     50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                 85                  90                  95

Ile Ala Asn Ile Tyr Thr Thr Gln His Arg Leu Asp Gln Gly Glu Ile
             100                 105                 110

Ser Ala Gly Asp Ala Ala Val Val Met Thr Ser Ala Gln Ile Thr Met
         115                 120                 125

Gly Met Pro Tyr Ala Val Thr Asp Ala Val Leu Ala Pro His Ile Gly
```

-continued

```
                130                 135                 140
Gly Glu Ala Gly Ser Ser His Ala Pro Pro Gln Ala Leu Thr Leu Ile
145                 150                 155                 160

Ile Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
                180                 185                 190

Leu Ile Pro Pro Thr Leu Pro Gly Thr Asn Ile Val Leu Gly Ala Leu
            195                 200                 205

Pro Glu Asp Arg His Ile Asp Arg Leu Ala Lys Arg Gln Arg Pro Gly
210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
                260                 265                 270

Glu Pro Gln Ser Asn Ala Gly Pro Arg Pro His Ile Gly Asp Thr Leu
                275                 280                 285

Phe Thr Leu Phe Arg Ala Pro Glu Leu Leu Ala Pro Asn Gly Asp Leu
            290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
                340                 345                 350

Thr Thr Pro Gly Ser Ile Pro Thr Ile Cys Asp Leu Ala Arg Thr Phe
            355                 360                 365

Ala Arg Glu Met Gly Glu Ala Asn
            370                 375

<210> SEQ ID NO 143
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 143

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
                20                  25                  30

Arg Gln Gln Glu Ala Thr Glu Val Arg Leu Glu Gln Lys Met Pro Thr
            35                  40                  45

Leu Leu Arg Val Tyr Ile Asp Gly Pro His Gly Met Gly Lys Thr Thr
50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
```

-continued

```
            115                 120                 125
Gly Met Pro Tyr Ala Val Thr Asp Ala Val Leu Ala Pro His Ile Gly
        130                 135                 140

Gly Glu Ala Gly Ser Ser His Ala Pro Pro Gln Ala Leu Thr Leu Ile
145                 150                 155                 160

Phe Glu Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
                180                 185                 190

Leu Ile Pro Pro Thr Leu Pro Gly Thr Asn Ile Val Leu Gly Ala Leu
            195                 200                 205

Pro Glu Asp Arg His Ile Asp Arg Leu Ala Lys Arg Gln Arg Pro Gly
        210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
                260                 265                 270

Glu Pro Gln Ser Asn Ala Gly Pro Arg Pro His Ile Gly Asp Thr Leu
            275                 280                 285

Phe Thr Leu Phe Arg Ala Pro Glu Leu Leu Ala Pro Asn Gly Asp Leu
        290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
                340                 345                 350

Thr Thr Pro Gly Ser Ile Pro Thr Ile Cys Asp Leu Ala Arg Thr Phe
            355                 360                 365

Ala Arg Glu Met Gly Glu Ala Asn
        370                 375

<210> SEQ ID NO 144
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 144

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
                20                  25                  30

Arg Gln Gln Glu Ala Thr Glu Val Arg Leu Glu Gln Lys Met Pro Thr
            35                  40                  45

Leu Leu Arg Val Tyr Ile Asp Gly Pro His Gly Met Gly Lys Thr Thr
        50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
```

-continued

```
                100                 105                 110
Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Ile Gly
        130                 135                 140

Gly Glu Ala Gly Ser Ser His Ala Pro Pro Arg Ala Leu Thr Leu Ile
145                 150                 155                 160

Phe Glu Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 145
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 145

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
```

```
                85                  90                  95
Ile Ala Asn Ile Tyr Thr Thr Gln His Arg Leu Asp Gln Gly Glu Ile
            100                 105                 110
Ser Ala Gly Asp Ala Ala Val Val Met Thr Ser Ala Gln Ile Thr Met
            115                 120                 125
Gly Met Pro Tyr Ala Val Thr Asp Ala Val Leu Ala Pro His Ile Gly
    130                 135                 140
Gly Glu Ala Gly Ser Ser His Ala Pro Pro Arg Ala Leu Thr Leu Ile
145                 150                 155                 160
Phe Gly Arg His Pro Ile Ala Ala Leu Leu Cys Tyr Pro Ala Ala Arg
                165                 170                 175
Tyr Leu Met Gly Ser Met Thr Pro Gln Ala Val Leu Ala Phe Val Ala
            180                 185                 190
Leu Ile Pro Pro Thr Leu Pro Gly Thr Asn Ile Val Leu Gly Ala Leu
            195                 200                 205
Pro Glu Asp Arg His Ile Asp Arg Leu Ala Lys Arg Gln Arg Pro Gly
            210                 215                 220
Glu Arg Leu Asp Leu Ala Met Leu Ala Ala Ile Arg Arg Val Tyr Gly
225                 230                 235                 240
Leu Leu Ala Asn Thr Val Arg Tyr Leu Gln Cys Gly Gly Ser Trp Arg
                245                 250                 255
Glu Asp Trp Gly Gln Leu Ser Gly Thr Ala Val Pro Pro Gln Gly Ala
            260                 265                 270
Glu Pro Gln Ser Asn Ala Gly Pro Arg Pro His Ile Gly Asp Thr Leu
            275                 280                 285
Phe Thr Leu Phe Arg Ala Pro Glu Leu Leu Ala Pro Asn Gly Asp Leu
    290                 295                 300
Tyr Asn Val Phe Ala Trp Ala Leu Asp Val Leu Ala Lys Arg Leu Arg
305                 310                 315                 320
Ser Met His Val Phe Ile Leu Asp Tyr Asp Gln Ser Pro Ala Gly Cys
                325                 330                 335
Arg Asp Ala Leu Leu Gln Leu Thr Ser Gly Met Val Gln Thr His Val
            340                 345                 350
Thr Thr Pro Gly Ser Ile Pro Thr Ile Cys Asp Leu Ala Arg Thr Phe
            355                 360                 365
Ala Arg Glu Met Gly Glu Ala Asn
    370                 375

<210> SEQ ID NO 146
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 146

Met Ala Ser Tyr Pro Gly His Gln His Ala Ser Ala Phe Asp Gln Ala
1               5                   10                  15
Ala Arg Ser Arg Gly His Ser Asn Arg Arg Thr Ala Leu Arg Pro Arg
            20                  25                  30
Arg Gln Gln Glu Ala Thr Glu Val Arg Leu Glu Gln Lys Met Pro Thr
        35                  40                  45
Leu Leu Arg Val Tyr Ile Asp Gly Pro His Gly Met Gly Lys Thr Thr
    50                  55                  60
Thr Thr Gln Leu Leu Val Ala Leu Gly Ser Arg Asp Asp Ile Val Tyr
```

-continued

```
            65                  70                  75                  80
Val Pro Glu Pro Met Thr Tyr Trp Gln Val Leu Gly Ala Ser Glu Thr
                    85                  90                  95

Ile Ala Asn Ile Tyr Thr Thr Gln His Arg Leu Asp Gln Gly Glu Ile
                100                 105                 110

Ser Ala Gly Asp Ala Ala Val Val Met Thr Ser Ala Gln Ile Thr Met
                115                 120                 125

Gly Met Pro Tyr Ala Val Thr Asp Ala Val Leu Ala Pro His Ile Gly
        130                 135                 140

Gly Glu Ala Gly Ser Ser His Ala Pro Pro Thr Ala Leu Thr Leu Ile
145                 150                 155                 160

Phe Glu Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
                180                 185                 190

Leu Ile Pro Pro Thr Leu Pro Gly Thr Asn Ile Val Leu Gly Ala Leu
                195                 200                 205

Pro Glu Asp Arg His Ile Asp Arg Leu Ala Lys Arg Gln Arg Pro Gly
        210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
                260                 265                 270

Glu Pro Gln Ser Asn Ala Gly Pro Arg Pro His Ile Gly Asp Thr Leu
                275                 280                 285

Phe Thr Leu Phe Arg Ala Pro Glu Leu Leu Ala Pro Asn Gly Asp Leu
        290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
                340                 345                 350

Thr Thr Pro Gly Ser Ile Pro Thr Ile Cys Asp Leu Ala Arg Thr Phe
                355                 360                 365

Ala Arg Glu Met Gly Glu Ala Asn
        370                 375

<210> SEQ ID NO 147
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 147

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
                20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
```

```
                 50                  55                  60
Thr Thr Gln Leu Leu Val Ala Leu Gly Ser Arg Asp Asp Ile Val Tyr
 65                  70                  75                  80

Val Pro Glu Pro Met Thr Tyr Trp Gln Val Leu Gly Ala Ser Glu Thr
                 85                  90                  95

Ile Ala Asn Ile Tyr Thr Thr Gln His Arg Leu Asp Gln Gly Glu Ile
                100                 105                 110

Ser Ala Gly Asp Ala Ala Val Met Thr Ser Ala Gln Ile Thr Met
                115                 120                 125

Gly Met Pro Tyr Ala Val Thr Asp Ala Val Leu Ala Pro His Ile Gly
130                 135                 140

Gly Glu Ala Gly Ser Ser His Ala Pro Pro Ala Leu Thr Leu Ile
145                 150                 155                 160

Ile Asp His His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
                180                 185                 190

Leu Ile Pro Pro Thr Leu Pro Gly Thr Asn Ile Val Leu Gly Ala Leu
                195                 200                 205

Pro Glu Asp Arg His Ile Asp Arg Leu Ala Lys Arg Gln Arg Pro Gly
210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
                260                 265                 270

Glu Pro Gln Ser Asn Ala Gly Pro Arg Pro His Ile Gly Asp Thr Leu
                275                 280                 285

Phe Thr Leu Phe Arg Ala Pro Glu Leu Leu Ala Pro Asn Gly Asp Leu
                290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
                340                 345                 350

Thr Thr Pro Gly Ser Ile Pro Thr Ile Cys Asp Leu Ala Arg Thr Phe
                355                 360                 365

Ala Arg Glu Met Gly Glu Ala Asn
370                 375

<210> SEQ ID NO 148
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 148

Met Ala Ser Tyr Pro Gly His Gln His Ala Ser Ala Phe Asp Gln Ala
 1               5                  10                  15

Ala Arg Ser Arg Gly His Ser Asn Arg Arg Thr Ala Leu Arg Pro Arg
                20                  25                  30

Arg Gln Gln Glu Ala Thr Glu Val Arg Leu Glu Gln Lys Met Pro Thr
```

```
                35                  40                  45
Leu Leu Arg Val Tyr Ile Asp Gly Pro His Gly Met Gly Lys Thr Thr
 50                  55                  60
Thr Thr Gln Leu Leu Val Ala Leu Gly Ser Arg Asp Asp Ile Val Tyr
 65                  70                  75                  80
Val Pro Glu Pro Met Thr Tyr Trp Gln Val Leu Gly Ala Ser Glu Thr
                 85                  90                  95
Ile Ala Asn Ile Tyr Thr Thr Gln His Arg Leu Asp Gln Gly Glu Ile
                100                 105                 110
Ser Ala Gly Asp Ala Ala Val Val Met Thr Ser Ala Gln Ile Thr Met
                115                 120                 125
Gly Met Pro Tyr Ala Val Thr Asp Ala Val Leu Ala Pro His Ile Gly
130                 135                 140
Gly Glu Ala Gly Ser Ser His Ala Pro Pro Pro Ala Leu Thr Leu Ile
145                 150                 155                 160
Ile Asp Arg His Arg Ile Ala Ala Leu Leu Cys Tyr Pro Ala Ala Arg
                165                 170                 175
Tyr Leu Met Gly Ser Met Thr Pro Gln Ala Val Leu Ala Phe Val Ala
                180                 185                 190
Leu Ile Pro Pro Thr Leu Pro Gly Thr Asn Ile Val Leu Gly Ala Leu
                195                 200                 205
Pro Glu Asp Arg His Ile Asp Arg Leu Ala Lys Arg Gln Arg Pro Gly
                210                 215                 220
Glu Arg Leu Asp Leu Ala Met Leu Ala Ala Ile Arg Arg Val Tyr Gly
225                 230                 235                 240
Leu Leu Ala Asn Thr Val Arg Tyr Leu Gln Cys Gly Gly Ser Trp Arg
                245                 250                 255
Glu Asp Trp Gly Gln Leu Ser Gly Thr Ala Val Pro Pro Gln Gly Ala
                260                 265                 270
Glu Pro Gln Ser Asn Ala Gly Pro Arg Pro His Ile Gly Asp Thr Leu
                275                 280                 285
Phe Thr Leu Phe Arg Ala Pro Glu Leu Leu Ala Pro Asn Gly Asp Leu
290                 295                 300
Tyr Asn Val Phe Ala Trp Ala Leu Asp Val Leu Ala Lys Arg Leu Arg
305                 310                 315                 320
Ser Met His Val Phe Ile Leu Asp Tyr Asp Gln Ser Pro Ala Gly Cys
                325                 330                 335
Arg Asp Ala Leu Leu Gln Leu Thr Ser Gly Met Val Gln Thr His Val
                340                 345                 350
Thr Thr Pro Gly Ser Ile Pro Thr Ile Cys Asp Leu Ala Arg Thr Phe
                355                 360                 365
Ala Arg Glu Met Gly Glu Ala Asn
370                 375

<210> SEQ ID NO 149
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 149

Met Ala Ser Tyr Pro Gly His Gln His Ala Ser Ala Phe Asp Gln Ala
1               5                  10                  15

Ala Arg Ser Arg Gly His Ser Asn Arg Arg Thr Ala Leu Arg Pro Arg
```

-continued

```
                    20                  25                  30
Arg Gln Gln Glu Ala Thr Glu Val Arg Leu Glu Gln Lys Met Pro Thr
             35                  40                  45

Leu Leu Arg Val Tyr Ile Asp Gly Pro His Gly Met Gly Lys Thr Thr
 50                  55                  60

Thr Thr Gln Leu Leu Val Ala Leu Gly Ser Arg Asp Asp Ile Val Tyr
 65                  70                  75                  80

Val Pro Glu Pro Met Thr Tyr Trp Gln Val Leu Gly Ala Ser Glu Thr
                 85                  90                  95

Ile Ala Asn Ile Tyr Thr Thr Gln His Arg Leu Asp Gln Gly Glu Ile
                100                 105                 110

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Ile Gly
        130                 135                 140

Gly Glu Ala Gly Ser Ser His Ala Pro Pro Ala Leu Thr Leu Ile
145                 150                 155                 160

Asn Asp Arg His Ser Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
                180                 185                 190

Leu Ile Pro Pro Thr Leu Pro Gly Thr Asn Ile Val Leu Gly Ala Leu
            195                 200                 205

Pro Glu Asp Arg His Ile Asp Arg Leu Ala Lys Arg Gln Arg Pro Gly
        210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
                260                 265                 270

Glu Pro Gln Ser Asn Ala Gly Pro Arg Pro His Ile Gly Asp Thr Leu
            275                 280                 285

Phe Thr Leu Phe Arg Ala Pro Glu Leu Leu Ala Pro Asn Gly Asp Leu
        290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 150
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 150

Met Ala Ser Tyr Pro Gly His Gln His Ala Ser Ala Phe Asp Gln Ala
```

```
1               5                   10                  15
Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
            35                  40                  45

Leu Leu Arg Val Tyr Ile Asp Gly Pro His Gly Met Gly Lys Thr Thr
        50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
                100                 105                 110

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Ile Gly
        130                 135                 140

Gly Glu Ala Gly Ser Ser His Ala Pro Pro Ala Leu Thr Leu Ile
145                 150                 155                 160

Phe Tyr Cys His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
                180                 185                 190

Leu Ile Pro Pro Thr Leu Pro Gly Thr Asn Ile Val Leu Gly Ala Leu
            195                 200                 205

Pro Glu Asp Arg His Ile Asp Arg Leu Ala Lys Arg Gln Arg Pro Gly
        210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 151
<211> LENGTH: 376
<212> TYPE: PRT
<213> ORGANISM: Artificial Sequence
<220> FEATURE:
<223> OTHER INFORMATION: HSVTK Mutant
```

<400> SEQUENCE: 151

```
Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asn Arg Lys Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375
```

<210> SEQ ID NO 152
<211> LENGTH: 376
<212> TYPE: PRT
<213> ORGANISM: Artificial Sequence

```
<220> FEATURE:
<223> OTHER INFORMATION: HSVTK Mutant

<400> SEQUENCE: 152

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
130                 135                 140

Gly Glu Ala Gly Ser Ser His Ala Pro Pro Pro Ala Leu Thr Leu Ile
145                 150                 155                 160

Phe Glu Arg Asn Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
370                 375

<210> SEQ ID NO 153
```

<211> LENGTH: 376
<212> TYPE: PRT
<213> ORGANISM: Artificial Sequence
<220> FEATURE:
<223> OTHER INFORMATION: HSVTK Mutant

<400> SEQUENCE: 153

```
Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asp Pro Gln Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375
```

<210> SEQ ID NO 154
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 154

```
Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Pro Ala Leu Thr Leu Ile
145                 150                 155                 160

Phe Asp Arg Gln Leu Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365
```

```
Ala Arg Glu Met Gly Glu Ala Asn
    370             375

<210> SEQ ID NO 155
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 155

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Gln Ala Leu Thr Leu Ile
145                 150                 155                 160

Phe Glu Arg His Leu Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350
```

```
Thr Thr Pro Gly Ser Ile Pro Thr Ile Cys Asp Leu Ala Arg Thr Phe
        355                 360                 365
Ala Arg Glu Met Gly Glu Ala Asn
    370                 375

<210> SEQ ID NO 156
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 156

Met Ala Ser Tyr Pro Gly His Gln His Ala Ser Ala Phe Asp Gln Ala
1               5                   10                  15
Ala Arg Ser Arg Gly His Ser Asn Arg Arg Thr Ala Leu Arg Pro Arg
            20                  25                  30
Arg Gln Gln Glu Ala Thr Glu Val Arg Leu Glu Gln Lys Met Pro Thr
        35                  40                  45
Leu Leu Arg Val Tyr Ile Asp Gly Pro His Gly Met Gly Lys Thr Thr
    50                  55                  60
Thr Thr Gln Leu Leu Val Ala Leu Gly Ser Arg Asp Asp Ile Val Tyr
65                  70                  75                  80
Val Pro Glu Pro Met Thr Tyr Trp Gln Val Leu Gly Ala Ser Glu Thr
                85                  90                  95
Ile Ala Asn Ile Tyr Thr Thr Gln His Arg Leu Asp Gln Gly Glu Ile
            100                 105                 110
Ser Ala Gly Asp Ala Ala Val Val Met Thr Ser Ala Gln Ile Thr Met
        115                 120                 125
Gly Met Pro Tyr Ala Val Thr Asp Ala Val Leu Ala Pro His Ile Gly
    130                 135                 140
Gly Glu Ala Gly Ser Ser His Ala Pro Pro Ala Ala Leu Thr Leu Ile
145                 150                 155                 160
Phe Asp Pro His Thr Ile Ala Ala Leu Leu Cys Tyr Pro Ala Ala Arg
                165                 170                 175
Tyr Leu Met Gly Ser Met Thr Pro Gln Ala Val Leu Ala Phe Val Ala
            180                 185                 190
Leu Ile Pro Pro Thr Leu Pro Gly Thr Asn Ile Val Leu Gly Ala Leu
        195                 200                 205
Pro Glu Asp Arg His Ile Asp Arg Leu Ala Lys Arg Gln Arg Pro Gly
    210                 215                 220
Glu Arg Leu Asp Leu Ala Met Leu Ala Ala Ile Arg Arg Val Tyr Gly
225                 230                 235                 240
Leu Leu Ala Asn Thr Val Arg Tyr Leu Gln Cys Gly Gly Ser Trp Arg
                245                 250                 255
Glu Asp Trp Gly Gln Leu Ser Gly Thr Ala Val Pro Pro Gln Gly Ala
            260                 265                 270
Glu Pro Gln Ser Asn Ala Gly Pro Arg Pro His Ile Gly Asp Thr Leu
        275                 280                 285
Phe Thr Leu Phe Arg Ala Pro Glu Leu Leu Ala Pro Asn Gly Asp Leu
    290                 295                 300
Tyr Asn Val Phe Ala Trp Ala Leu Asp Val Leu Ala Lys Arg Leu Arg
305                 310                 315                 320
Ser Met His Val Phe Ile Leu Asp Tyr Asp Gln Ser Pro Ala Gly Cys
                325                 330                 335
```

Arg Asp Ala Leu Leu Gln Leu Thr Ser Gly Met Val Gln Thr His Val
        340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 157
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 157

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Pro Ala Leu Thr Leu Ile
145                 150                 155                 160

Phe Asn Ser Asn Ala Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

```
Ser Met His Val Phe Ile Leu Asp Tyr Asp Gln Ser Pro Ala Gly Cys
            325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
            355                 360                 365

Ala Arg Glu Met Gly Glu Ala Asn
            370                 375

<210> SEQ ID NO 158
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 158

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Ala Leu Thr Leu Ile
145                 150                 155                 160

Cys Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300
```

```
Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 159
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 159

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
130                 135                 140

Gly Glu Ala Gly Ser Ser His Ala Pro Pro Ala Ala Leu Thr Leu Ile
145                 150                 155                 160

Phe Glu Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285
```

```
Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 160
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 160

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Leu
145                 150                 155                 160

Leu Asp Arg His Pro Ile Ala Val Met Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270
```

```
Glu Pro Gln Ser Asn Ala Gly Pro Arg Pro His Ile Gly Asp Thr Leu
            275                 280                 285

Phe Thr Leu Phe Arg Ala Pro Glu Leu Leu Ala Pro Asn Gly Asp Leu
        290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
370                 375

<210> SEQ ID NO 161
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 161

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Leu Asp Arg His Pro Ile Ala Val Tyr Cys Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255
```

```
Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
            275                 280                 285

Phe Thr Leu Phe Arg Ala Pro Glu Leu Leu Ala Pro Asn Gly Asp Leu
            290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
            325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
            355                 360                 365

Ala Arg Glu Met Gly Glu Ala Asn
            370                 375

<210> SEQ ID NO 162
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 162

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
            35                  40                  45

Leu Leu Arg Val Tyr Ile Asp Gly Pro His Gly Met Gly Lys Thr Thr
        50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
            85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Ile Gly
            130                 135                 140

Gly Glu Ala Gly Ser Ser His Ala Pro Pro Ala Leu Thr Leu Ile
145                 150                 155                 160

Ile Asp Arg His Pro Ile Ala Ala Leu Leu Cys Tyr Pro Ala Ala Arg
            165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
            195                 200                 205

Pro Glu Asp Arg His Ile Asp Arg Leu Ala Lys Arg Gln Arg Pro Gly
            210                 215                 220

Glu Arg Leu Asp Leu Ala Met Leu Ala Ala Ile Arg Arg Val Tyr Gly
225                 230                 235                 240
```

```
Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 163
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 163

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
                20                  25                  30

Arg Gln Gln Glu Ala Thr Glu Val Arg Leu Glu Gln Lys Met Pro Thr
            35                  40                  45

Leu Leu Arg Val Tyr Ile Asp Gly Pro His Gly Met Gly Lys Thr Thr
        50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Cys Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220
```

```
Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
            245                 250                 255

Glu Asp Trp Gly Gln Leu Ser Gly Thr Ala Val Pro Pro Gln Gly Ala
        260                 265                 270

Glu Pro Gln Ser Asn Ala Gly Pro Arg Pro His Ile Gly Asp Thr Leu
    275                 280                 285

Phe Thr Leu Phe Arg Ala Pro Glu Leu Leu Ala Pro Asn Gly Asp Leu
290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
            325                 330                 335

Arg Asp Ala Leu Leu Gln Leu Thr Ser Gly Met Val Gln Thr His Val
        340                 345                 350

Thr Thr Pro Gly Ser Ile Pro Thr Ile Cys Asp Leu Ala Arg Thr Phe
    355                 360                 365

Ala Arg Glu Met Gly Glu Ala Asn
370                 375

<210> SEQ ID NO 164
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 164

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Leu Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205
```

```
Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 165
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 165

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asp Arg His Pro Ile Ser Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190
```

Leu Ile Pro Pro Thr Leu Pro Gly Thr Asn Ile Val Leu Gly Ala Leu
            195                 200                 205

Pro Glu Asp Arg His Ile Asp Arg Leu Ala Lys Arg Gln Arg Pro Gly
        210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
        290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
370                 375

<210> SEQ ID NO 166
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 166

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Pro Ala Leu Thr Leu Ile
145                 150                 155                 160

Phe Asp Arg His Pro Ile Ser Ala Leu Leu Cys Tyr Pro Val Ala Arg
                165                 170                 175

-continued

```
Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 167
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 167

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Pro Ala Leu Thr Leu Ile
145                 150                 155                 160
```

```
Phe Asp Arg His Ala Ile Ala Ala Leu Leu Cys Tyr Pro Val Ala Arg
            165                 170                 175
Tyr Leu Met Gly Ser Met Thr Pro Gln Ala Val Leu Ala Phe Val Ala
            180                 185                 190
Leu Ile Pro Pro Thr Leu Pro Gly Thr Asn Ile Val Leu Gly Ala Leu
            195                 200                 205
Pro Glu Asp Arg His Ile Asp Arg Leu Ala Lys Arg Gln Arg Pro Gly
            210                 215                 220
Glu Arg Leu Asp Leu Ala Met Leu Ala Ala Ile Arg Arg Val Tyr Gly
225                 230                 235                 240
Leu Leu Ala Asn Thr Val Arg Tyr Leu Gln Cys Gly Gly Ser Trp Arg
            245                 250                 255
Glu Asp Trp Gly Gln Leu Ser Gly Thr Ala Val Pro Pro Gln Gly Ala
            260                 265                 270
Glu Pro Gln Ser Asn Ala Gly Pro Arg Pro His Ile Gly Asp Thr Leu
            275                 280                 285
Phe Thr Leu Phe Arg Ala Pro Glu Leu Leu Ala Pro Asn Gly Asp Leu
            290                 295                 300
Tyr Asn Val Phe Ala Trp Ala Leu Asp Val Leu Ala Lys Arg Leu Arg
305                 310                 315                 320
Ser Met His Val Phe Ile Leu Asp Tyr Asp Gln Ser Pro Ala Gly Cys
            325                 330                 335
Arg Asp Ala Leu Leu Gln Leu Thr Ser Gly Met Val Gln Thr His Val
            340                 345                 350
Thr Thr Pro Gly Ser Ile Pro Thr Ile Cys Asp Leu Ala Arg Thr Phe
            355                 360                 365
Ala Arg Glu Met Gly Glu Ala Asn
            370                 375

<210> SEQ ID NO 168
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 168

Met Ala Ser Tyr Pro Gly His Gln His Ala Ser Ala Phe Asp Gln Ala
1               5                   10                  15
Ala Arg Ser Arg Gly His Ser Asn Arg Arg Thr Ala Leu Arg Pro Arg
            20                  25                  30
Arg Gln Gln Glu Ala Thr Glu Val Arg Leu Glu Gln Lys Met Pro Thr
        35                  40                  45
Leu Leu Arg Val Tyr Ile Asp Gly Pro His Gly Met Gly Lys Thr Thr
    50                  55                  60
Thr Thr Gln Leu Leu Val Ala Leu Gly Ser Arg Asp Asp Ile Val Tyr
65                  70                  75                  80
Val Pro Glu Pro Met Thr Tyr Trp Gln Val Leu Gly Ala Ser Glu Thr
            85                  90                  95
Ile Ala Asn Ile Tyr Thr Thr Gln His Arg Leu Asp Gln Gly Glu Ile
            100                 105                 110
Ser Ala Gly Asp Ala Ala Val Val Met Thr Ser Ala Gln Ile Thr Met
            115                 120                 125
Gly Met Pro Tyr Ala Val Thr Asp Ala Val Leu Ala Pro His Ile Gly
            130                 135                 140
```

```
Gly Glu Ala Gly Ser Ser His Ala Pro Pro Ala Leu Thr Leu Ile
145                 150                 155                 160

Phe Gly Arg His Ala Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 169
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 169

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125
```

```
Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Glu Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 170
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 170

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
                20                  25                  30

Arg Gln Gln Glu Ala Thr Glu Val Arg Leu Glu Gln Lys Met Pro Thr
            35                  40                  45

Leu Leu Arg Val Tyr Ile Asp Gly Pro His Gly Met Gly Lys Thr Thr
        50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110
```

```
Ser Ala Gly Asp Ala Ala Val Val Met Thr Ser Ala Gln Ile Thr Met
            115                 120                 125
Gly Met Pro Tyr Ala Val Thr Asp Ala Val Leu Ala Pro His Ile Gly
        130                 135                 140
Gly Glu Ala Gly Ser Ser His Ala Pro Pro Ala Leu Thr Leu Ile
145                 150                 155                 160
Phe Asp Pro His Pro Ile Ala Ala Leu Leu Cys Tyr Pro Ala Ala Arg
                165                 170                 175
Tyr Leu Met Gly Ser Met Thr Pro Gln Ala Val Leu Ala Phe Val Ala
            180                 185                 190
Leu Ile Pro Pro Thr Leu Pro Gly Thr Asn Ile Val Leu Gly Ala Leu
        195                 200                 205
Pro Glu Asp Arg His Ile Asp Arg Leu Ala Lys Arg Gln Arg Pro Gly
    210                 215                 220
Glu Arg Leu Asp Leu Ala Met Leu Ala Ala Ile Arg Arg Val Tyr Gly
225                 230                 235                 240
Leu Leu Ala Asn Thr Val Arg Tyr Leu Gln Cys Gly Gly Ser Trp Arg
                245                 250                 255
Glu Asp Trp Gly Gln Leu Ser Gly Thr Ala Val Pro Pro Gln Gly Ala
            260                 265                 270
Glu Pro Gln Ser Asn Ala Gly Pro Arg Pro His Ile Gly Asp Thr Leu
        275                 280                 285
Phe Thr Leu Phe Arg Ala Pro Glu Leu Leu Ala Pro Asn Gly Asp Leu
    290                 295                 300
Tyr Asn Val Phe Ala Trp Ala Leu Asp Val Leu Ala Lys Arg Leu Arg
305                 310                 315                 320
Ser Met His Val Phe Ile Leu Asp Tyr Asp Gln Ser Pro Ala Gly Cys
                325                 330                 335
Arg Asp Ala Leu Leu Gln Leu Thr Ser Gly Met Val Gln Thr His Val
            340                 345                 350
Thr Thr Pro Gly Ser Ile Pro Thr Ile Cys Asp Leu Ala Arg Thr Phe
        355                 360                 365
Ala Arg Glu Met Gly Glu Ala Asn
    370                 375

<210> SEQ ID NO 171
<211> LENGTH: 376
<212> TYPE: PRT
<213> ORGANISM: Artificial Sequence
<220> FEATURE:
<223> OTHER INFORMATION: HSVTK Mutant

<400> SEQUENCE: 171

Met Ala Ser Tyr Pro Gly His Gln His Ala Ser Ala Phe Asp Gln Ala
1               5                   10                  15
Ala Arg Ser Arg Gly His Ser Asn Arg Arg Thr Ala Leu Arg Pro Arg
            20                  25                  30
Arg Gln Gln Glu Ala Thr Glu Val Arg Leu Glu Gln Lys Met Pro Thr
        35                  40                  45
Leu Leu Arg Val Tyr Ile Asp Gly Pro His Gly Met Gly Lys Thr Thr
    50                  55                  60
Thr Thr Gln Leu Leu Val Ala Leu Gly Ser Arg Asp Asp Ile Val Tyr
65                  70                  75                  80
Val Pro Glu Pro Met Thr Tyr Trp Gln Val Leu Gly Ala Ser Glu Thr
                85                  90                  95
```

```
Ile Ala Asn Ile Tyr Thr Thr Gln His Arg Leu Asp Gln Gly Glu Ile
            100                 105                 110
Ser Ala Gly Asp Ala Ala Val Val Met Thr Ser Ala Gln Ile Thr Met
            115                 120                 125
Gly Met Pro Tyr Ala Val Thr Asp Ala Val Leu Ala Pro His Ile Gly
        130                 135                 140
Gly Glu Ala Gly Ser Ser His Ala Pro Pro Pro Ala Leu Thr Leu Ile
145                 150                 155                 160
Phe Asp Arg Gln Pro Ile Ala Ala Leu Leu Cys Tyr Pro Ala Ala Arg
                165                 170                 175
Tyr Leu Met Gly Ser Met Thr Pro Gln Ala Val Leu Ala Phe Val Ala
            180                 185                 190
Leu Ile Pro Pro Thr Leu Pro Gly Thr Asn Ile Val Leu Gly Ala Leu
            195                 200                 205
Pro Glu Asp Arg His Ile Asp Arg Leu Ala Lys Arg Gln Arg Pro Gly
        210                 215                 220
Glu Arg Leu Asp Leu Ala Met Leu Ala Ala Ile Arg Arg Val Tyr Gly
225                 230                 235                 240
Leu Leu Ala Asn Thr Val Arg Tyr Leu Gln Cys Gly Gly Ser Trp Arg
                245                 250                 255
Glu Asp Trp Gly Gln Leu Ser Gly Thr Ala Val Pro Pro Gly Gly Ala
            260                 265                 270
Glu Pro Gln Ser Asn Ala Gly Pro Arg Pro His Ile Gly Asp Thr Leu
            275                 280                 285
Phe Thr Leu Phe Arg Ala Pro Glu Leu Leu Ala Pro Asn Gly Asp Leu
        290                 295                 300
Tyr Asn Val Phe Ala Trp Ala Leu Asp Val Leu Ala Lys Arg Leu Arg
305                 310                 315                 320
Ser Met His Val Phe Ile Leu Asp Tyr Asp Gln Ser Pro Ala Gly Cys
                325                 330                 335
Arg Asp Ala Leu Leu Gln Leu Thr Ser Gly Met Val Gln Thr His Val
            340                 345                 350
Thr Thr Pro Gly Ser Ile Pro Thr Ile Cys Asp Leu Ala Arg Thr Phe
            355                 360                 365
Ala Arg Glu Met Gly Glu Ala Asn
        370                 375

<210> SEQ ID NO 172
<211> LENGTH: 21
<212> TYPE: DNA
<213> ORGANISM: Artificial Sequence
<220> FEATURE:
<223> OTHER INFORMATION: Primer

<400> SEQUENCE: 172
gtctcggagg cgcccagcac c                                              21
```

FUSION PROTEINS HAVING THYMIDINE KINASE AND GUANYLATE KINASE ACTIVITIES

CROSS-REFERENCE TO RELATED APPLICATIONS

This application claims the benefit of U.S. Provisional Application No. 60/061,812, filed Oct. 14, 1997, which application is incorporated by reference in its entirety.

TECHNICAL FIELD

The present invention relates generally to mutant enzymes of the Herpesviridae and, more specifically, to compositions and methods which utilize thymidine kinase mutants. The present invention also relates to fusion proteins having both guanylate kinase and thymidine kinase activities.

BACKGROUND OF THE INVENTION

Although many bacterial diseases are, in general, easily treated with antibiotics, very few effective treatments exist for many viral, parasitic, cancerous, and genetic diseases. Cancer, for example, may be treated by surgical resection of a solid tumor. Nevertheless, a majority of patients with solid tumors also possess micrometastases beyond the primary tumor site. If treated with surgery alone, approximately 70% of these patients will experience recurrence of the cancer. Thus, cancer accounts for one-fifth of the total mortality in the United States, and is the second leading cause of death.

In addition to surgery, many cancers are now also treated with a combination of therapies involving cytotoxic chemotherapeutic drugs (e.g. vincristine, vinblastine, cisplatin, methotrexate, 5-FU, etc.) and/or radiation therapy. One difficulty with this approach, however, is that radiotherapeutic and chemotherapeutic agents are toxic to normal tissues, and often create life-threatening side effects. In addition, these approaches often have extremely high failure/remission rates (up to 90% depending upon the type of cancer).

Numerous other methods have been attempted in order to bolster or augment an individual's own immune system in order to eliminate cancer cells. For example, some scientists have utilized bacterial or viral components as adjuvants, in order to stimulate the immune system to destroy tumor cells. Such agents have generally been useful as adjuvants and as nonspecific stimulants in animal tumor models, but have not yet proved to be generally effective in humans.

Lymphokines have also been utilized in the treatment of cancer (as well as viral and parasitic diseases), in order to stimulate or affect specific immune cells in the generation of an immune response. One group, for example, utilized the lymphokine Interleukin-2 in order to stimulate peripheral blood cells in order to expand and produce large quantities of cells which are cytotoxic to tumor cells (Rosenberg et al., *N. Engl. J. Med.* 313:1485-1492, 1985).

Others have suggested the use of antibody-mediated treatment using specific monoclonal antibodies or "magic bullets" in order to specifically target and kill tumor cells (Dillman, "Antibody Therapy," Principles of Cancer Biotherapy, Oldham (ed.), Raven Press, Ltd., New York, 1987). One difficulty, however, is that most monoclonal antibodies are of murine origin, and thus hypersensitivity against the murine antibody may limit its efficacy, particularly after repeated therapies. Common side effects include fever, sweats and chills, skin rashes, arthritis, and nerve palsies.

One approach which has recently garnered significant interest is the use of gene therapy, which has been utilized to treat not only genetic diseases, but viral and cancerous diseases as well (see PCT Publication Nos. WO 91/02805, EPO 415,731, and WO 90/07936). Briefly, specifically designed vectors which have been derived from viruses are used to deliver particular genetic information into cells. Such genetic information may itself be useful to block expression of damaging proteins or antigens (e.g., antisense therapy), may encode proteins which are toxic to and kill selected cells, may encode therapeutic proteins which bolster a cell's immune response, or encode proteins which replace inactive or nonexistent proteins.

One protein which has recently been suggested for use in such therapies is the type 1 Herpes Simplex Virus thymidine kinase (HSVTK-1). Briefly, thymidine kinase is a salvage pathway enzyme which phosphorylates natural nucleoside substrates as well as nucleoside analogues (see Balasubramaniam et al., *J. of Gen. Vir.* 71:2979-2987, 1990). This protein may be utilized therapeutically by introducing a retroviral vector which expresses the protein into the cell, followed by administration of a nucleoside analogue such as acyclovir or ganciclovir. HSVTK-1 then phosphorylates the nucleoside analogue, creating a toxic product capable of killing the host cell. Thus, use of retroviral vectors which express HSVTK has been suggested for not only the treatment of cancers, but for other diseases as well.

The present invention provides novel thymidine kinase mutants and TK fusion proteins with enhanced biological activities which are suitable for a variety of applications, such as gene therapy, and further provides other, related advantages.

SUMMARY OF THE INVENTION

Briefly stated, the present invention provides compositions and methods which utilize Herpesviridae thymidine kinase mutants. Within one aspect of the present invention, isolated nucleic acid molecules which encode Herpesviridae thymidine kinase enzymes comprising one or more mutations are provided, wherein at least one of the mutations encoding an amino acid substitution is positioned within the Q substrate binding domain, wherein the mutation increases a biological activity of the thymidine kinase, as compared to unmutated thymidine kinase. Within another aspect of the present invention, isolated nucleic acid molecules are provided encoding a Herpesviridae thymidine kinase enzyme comprising at least three mutations, at least two of the mutations being amino acid substitutions located toward the N-terminus from a DRH nucleoside binding site (e.g., 1, 2 or 3 amino acids toward the N-terminus), and at least one mutation located toward the C-terminus from a DRH nucleoside binding site (e.g., 4 or 5 amino acids toward the C-terminus) which increases a biological activity of the thymidine kinase, as compared to unmutated thymidine kinase. Representative examples of suitable Herpesviridae thymidine kinase enzymes include Herpes Simplex Virus Type 1 thymidine kinase, Herpes Simplex Virus Type 2 thymidine kinase, Varicella Zoster Virus thymidine kinase, and marmoset herpesvirus, feline herpesvirus type 1, pseudorabies virus, equine herpesvirus type 1, bovine herpesvirus type 1, turkey herpesvirus, Marek's disease virus, herpesvirus saimiri and Epstein-Barr virus thymidine kinases. Within other embodiments, the thymidine kinase may be a primate herpesvirus thymidine kinase, or a non-primate herpesvirus thymidine kinase, such as an avian herpesvirus thymidine kinase.

A wide variety of mutations are contemplated within the context of the present invention. For example, within one embodiment mutations, such as amino acid substitutions, may occur within a region that includes the Q substrate binding domain and an additional 11 amino acids from this domain, toward the N-terminus.

In other embodiments, at least one mutation occurs within this "expanded" Q substrate binding domain or within the Q substrate binding domain, and at least one mutation is present outside these two regions. For example, one or more additional mutations may be located within a DRH nucleoside binding site which increases a biological activity of said thymidine kinase, as compared to unmutated thymidine kinase. For example, glutamic acid may be substituted for aspartic acid in the DRH nucleoside binding site, or a histidine residue may be substituted for arginine in the DRH nucleoside binding site.

Within yet another aspect, isolated nucleic acid molecules are provided encoding a Herpesviridae thymidine kinase enzyme comprising at least one mutation, such as an amino acid substitution, within a Q substrate binding domain (or within an expanded Q substrate binding domain) and at least one additional mutation being an amino acid substitution located toward the C-terminus from a DRH nucleoside binding site (e.g., 4, 5 or 6 amino acids toward the C-terminus) which increases a biological activity of the thymidine kinase, as compared to unmutated thymidine kinase.

Alternatively, additional mutations may encode one or more amino acid substitutions located from 1 to 7 amino acids toward the N-terminus from the DRH nucleoside binding site. For example, the amino acid which is one position toward the N-terminus from the DRH nucleoside binding site is substituted with an amino acid selected from the group consisting of valine, leucine, cysteine and isoleucine. Within another embodiment, the amino acid alanine is substituted for the amino acid which is present seven amino acids toward the N-terminus from the DRH nucleoside binding site. Within other embodiments, the thymidine kinase enzyme is truncated, and yet retains biological activity.

Within further embodiments of the invention, isolated nucleic acid molecules are provided which encode a thymidine kinase enzyme capable of phosphorylating a nucleoside analogue (e.g., acyclovir or ganciclovir) at least one-fold over the phosphorylation of the nucleoside analogue by a wild-type thymidine kinase enzyme. Within other embodiments, the thymidine kinase enzyme phosphorylates a nucleoside analogue at least x-fold over the phosphorylation of a nucleoside analogue by a wild-type thymidine kinase enzyme, wherein x is selected from the group consisting of 1.5, 2, 2.5, 3, 3.5, 4, 4.5 and 5. Within yet another embodiment, the thymidine kinase enzyme is capable of phosphorylating a nucleoside analogue, wherein $$z < \left[ \frac{(TKmNAp)/TKmTp)}{(TKwtNAp)/(TKwtTp)} \right]$$

and wherein $TK_m\ NA_p$ is the rate of phosphorylation of a nucleoside analogue by a thymidine kinase mutant, $TK_m\ T_p$ is the rate of phosphorylation of thymidine by a thymidine kinase mutant, $TK_{wt}\ NA_p$ is the rate of phosphorylation of a nucleoside analogue by an unmutated thymidine kinase enzyme, $TK_{wt}\ T_p$ is the rate of phosphorylation of a thymidine kinase enzyme by an unmutated thymidine kinase enzyme, and z is selected from the group consisting of 1, 1.5, 2, 2.5, 3, 3.5, 4, 4.5 and 5. Representative examples of suitable nucleoside analogues include ganciclovir, acyclovir, famciclovir, buciclovir, penciclovir, valciclovir, trifluorothymidine, 1-[2-deoxy, 2-fluoro, beta-D-arabino furanosyl]-5-iodouracil, ara-A, araT 1-beta-D-arabinofuranoxyl thymine, 5-ethyl-2'-deoxyuridine, 5-iodo-5'-amino-2,5'-dideoxyuridine, idoxuridine, AZT, AIU, dideoxycytidine and AraC.

Particularly preferred mutant thymidine kinases for the increased phosphorylation of nucleoside analogues include those wherein the enzyme is a type 1 Herpes Simplex Virus thymidine kinase.

Within other aspects of the present invention, mutant thymidine kinase enzymes which are encoded by the above-described nucleic acid molecules are provided, as well as vectors which are capable of expressing such molecules. Within one aspect, expression vectors are provided comprising a promoter operably linked to a nucleic acid molecule of the present invention. Within a preferred aspect, the vector is a viral vector capable of directing the expression of a nucleic acid molecule as described above. Representative examples of such viral vectors include herpes simplex viral vectors, adenoviral vectors, adenovirus-associated viral vectors, pox vectors, parvoviral vectors, baculovirus vectors and retroviral vectors. Within another aspect, viral vectors are provided which are capable of directing the expression of a nucleic acid molecule which encodes a thymidine kinase enzyme comprising one or more mutations, at least one of the mutations encoding an amino acid substitution which increases a biological activity of thymidine kinase, as compared to unmutated thymidine kinase.

A wide variety of promoters may be utilized in the present invention, including, for example, promoters such as the MoMLV LTR, RSV LTR, Friend MuLv LTR, Adenoviral promoter, Neomycin phosphotransferase promoter/enhancer, late parvovirus promoter, Herpes TK promoter, SV40 promoter, Metallothionen IIa gene enhancer/promoter, Cytomegalovirus Immediate Early Promoter, Cytomegalovirus Immediate Late Promoter, as well as tissue-specific promoters such as the tyrosinase related promoters (TRP-1 and TRP-2), DF3 enhancer, SLPI promoter (secretory leucoprotease inhibitor—expressed in many types of carcinomas), TRS (tissue specific regulatory sequences), tyrosine hydroxylase promoter, adipocyte P2 promoter, PEPCK promoter, CEA promoter, α fetoprotein promoter, whey acidic promoter, and casein promoter. Within related aspects, the above-described vectors may be provided as pharmaceutical compositions, along with a pharmaceutically acceptable carrier or diluent.

The present invention further provides nucleic acid molecules encoding fusion proteins that comprise a thymidine kinase moiety and a guanylate kinase moiety. Such fusion proteins possess biological activities of both thymidine kinase and guanylate kinase. The thymidine kinase moiety may derived from a wild-type thymidine kinase or from one of the thymidine kinase mutants described herein.

Within further aspects, sequences which encode thymidine kinase mutants, thymidine kinase fusion proteins, or fusion proteins having guanylate kinase and thymidine kinase activities described herein may be included within a given vector which is utilized for the purposes of gene therapy. Cells which contain these vectors may subsequently be killed by administration of a nucleoside analogue, in order to prevent formation of replication competent virus or aberrant integration of the vector into the host cell. Such compositions or methods are referred to as "suicide vectors" or a "failsafe" approach to gene therapy.

Within other aspects of the present invention, host cells are provided which carry one of the above-described vectors.

Representative examples of such cells include human cells, dog cells, monkey cells, rat cells, and mouse cells.

Within other aspects of the present invention, methods are provided for inhibiting a pathogenic agent in a warm-blooded animal, comprising the step of administering to a warm-blooded animal a vector as described above, such that the pathogenic agent is inhibited. Within various embodiments, the vector may be administered in vivo, or to cells ex vivo, which are then transplanted (or re-transplanted) in the animal. Within other embodiments, the pathogenic agent may be viruses, bacteria, parasites, tumor cells, or autoreactive immune cells.

Within other aspects of the present invention, methods are provided for noninvasive monitoring of the activity of herpes virus thymidine kinase activity, such as for the monitoring of the progress of gene therapy using herpes virus thymidine kinase. According to such methods, a subject, who has received a vector comprising a herpes virus thymidine kinase, is scanned (e.g., using a clinical gamma camera or by single-photon emission tomography) for radiolabeled anti-viral drugs that are substrates for the thymidine kinase.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

BRIEF DESCRIPTION OF THE DRAWINGS

FIG. 1 is a schematic outline which depicts a strategy for construction of a random nucleotide-containing library, and selection of TK mutants.

FIG. 3 depicts the nucleic acid and amino acid sequences of: Wildtype, TKF 105, TK1208, and ATKF2 TK for codons 165 to 175.

FIG. 14 is an illustration which depicts the nucleotides which were randomized in the LIF-ALL library, as well as the results of selection.

FIG. 15 is a table which shows amino acid substitutions of selected and unselected clones.

FIG. 16 is a table which shows the number of mutants selected from the LIF-ALL library which were sensitive to GCV or ACV.

FIG. 17 is a table which shows nucleotide changes in selected TK mutants.

FIG. 18 is a table which shows the amino acid sequence at positions 159-161 and 168-170, and phosphorylation level of several mutant TKs.

FIG. 21 shows semi-randomized olignucleotides used to generate a second generation of TK mutants having amino acid substitutions in residues 159-161 and 168-169.

FIG. 22 illustrates the use of particular oligonucleotides to construct TK mutants having amino acid substitutions in residues 112-132.

FIG. 23 shows nucleotides in the open reading frame of HSVTK-1 (SEQUENCE ID No. 1).

FIG. 24 illustrates a nucleotide sequence and deduced amino acid sequence representative of a human guanylate kinase.

FIG. 25 illustrates a nucleotide sequence and deduced amino acid sequence of a representative murine guanylate kinase.

DETAILED DESCRIPTION OF THE INVENTION

Definitions

Figure 2:
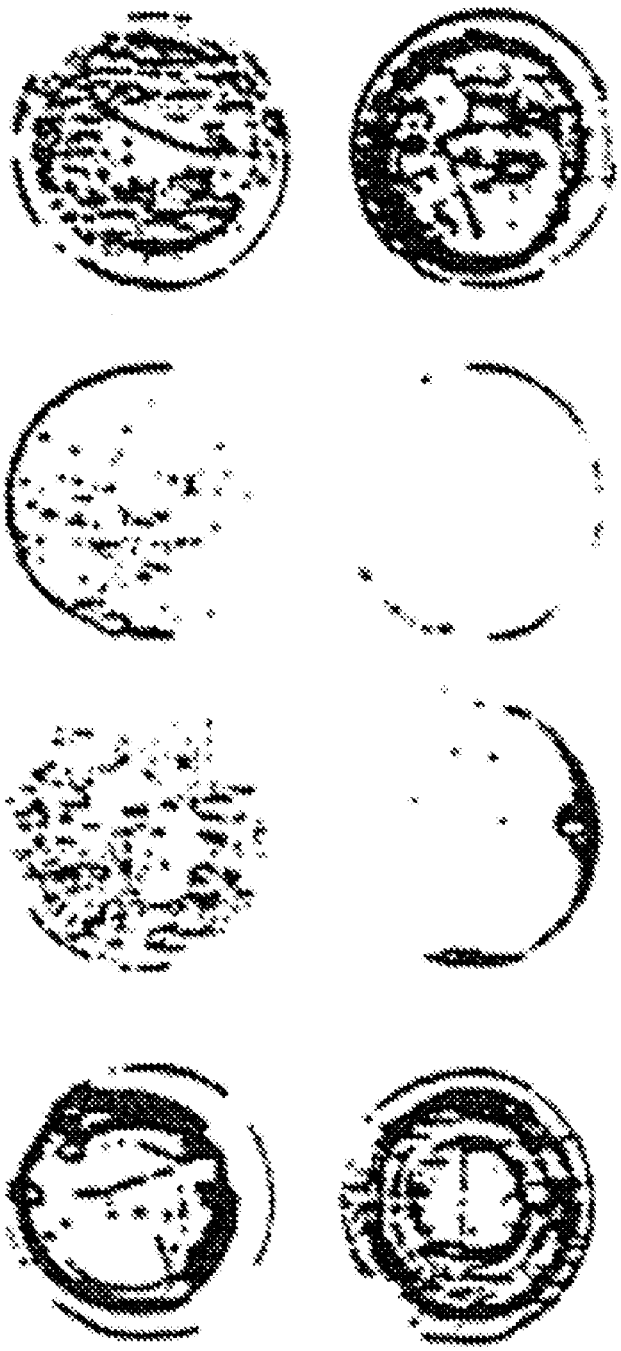
FIG. 2 is a photograph which shows selection of TK and AZT mutants.

Prior to setting forth the invention, it may be helpful to an understanding thereof to first set forth definitions of certain terms that will be used hereinafter.

"Vector" refers to an assembly which is capable of directing the expression of the mutant tk gene, as well as any additional sequence(s) or gene(s) of interest. The vector must include transcriptional promoter/enhancer elements, as well as another sequence which, when transcribed, is operably linked to the tk gene and/or other gene of interest. The vector may be composed of either deoxyribonucleic acids ("DNA"), ribonucleic acids ("RNA"), or a combination of the two (e.g., a DNA-RNA chimeric). Optionally, the vector may include a polyadenylation sequence, one or more restriction sites, as well as one or more selectable markers such as neomycin phosphotransferase or hygromycin phosphotransferase.

Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

"Tissue-specific promoter" refers to transcriptional promoter/enhancer elements which control gene expression in a limited number of tissues, or in a single tissue. Representative examples of tissue-specific promoters include the tyrosine hydroxylase promoter, adipocyte P2 promoter, PEPCK promoter, α fetoprotein promoter, whey acidic promoter, and casein promoter.

"Biological activity of thimidine kinase" refers to the ability of the thymidine kinase enzyme to phosphorylate nucleosides (e.g., dT) and nucleoside analogues such as ganciclovir (9-{[2-hydroxy-1-(hydroxymethyl)ethoxy] methyl}guanosine), famciclovir, buciclovir, penciclovir, valciclovir, acyclovir (9-[2-hydroxy ethoxy)methyl] guanosine), trifluorothymidine, 1-[2-deoxy, 2-fluoro, beta-D-arabino furanosyl]-5-iodouracil, ara-A (adenosine arabinoside, vivarabine), 1-beta-D-arabinofuranoxyl thymine, 5-ethyl-2'-deoxyuridine, 5-iodo-5'-ammo-2,5'-dideoxyuridine, idoxuridine (5-iodo-2'-deoxyuridine), AZT (3' azido-3' thymidine), ddC (dideoxycytidine), AIU (5-iodo-5' amino 2',5'-dideoxyuridine) and AraC (cytidine arabinoside). As utilized herein, a thymidine kinase mutant is considered to have "increased biological activity" if the level or rate of activity increases at least "y" fold over unmutated thymidine kinase, wherein y is selected from the group consisting of 1, 1.5, 2, 2.5, 3, 3.5, 4, 4.5 and 5. Within preferred embodiments, thymidine kinase mutants are considered to have increased biological activity when $$z < \left[ \frac{(TKmNAp)/TKmTp)}{(TKwtNAp)/(TKwtTp)} \right]$$

wherein $TK_m\ NA_p$ is the rate of phosphorylation of a nucleoside analogue by a thymidine kinase mutant, $TK_m\ T_p$ is the rate of phosphorylation of thymidine by a thymidine kinase mutant, $TK_{wt}\ NA_p$ is the rate of phosphorylation of a nucleoside analogue by an unmutated thymidine kinase enzyme, $TK_{wt}\ T_p$ is the rate of phosphorylation of a thymidine kinase enzyme by an unmutated thymidine kinase enzyme, and z is selected from the group consisting of 1, 1.5, 2, 2.5, 3, 3.5, 4, 4.5 and 5.

"Biological activity of guanylate kinase" refers to the ability of the guanylate kinase enzyme to catalyze the reversible transfer of the terminal phosphoryl group of ATP to an acceptor molecule such as GMP or dGMP. Guanylate kinase (gmk) can also phosphorylate nucleosides and nucleoside analogs that have been phosphorylated by thymidine kinase. Examples of thymidine kinase substrates are described above.

In addition to the ability of thymidine kinase and guanylate kinase to phosphorylate nucleosides and nucleoside analogues, the phrase "biological activity" should also be understood to refer to other biological properties of these enzymes, such as protein stability (e.g., as measured by resistance to proteolytic enzyme degradation by enzymes such as trypsin), and thermostability (e.g., maintenance of nucleoside analogue phosphorylation upon increases in temperature).

"Pathogenic agent" refers to either a foreign organism which is responsible for a disease state, or an "altered" cell which is responsible for a disease state. Representative examples of pathogenic agents include foreign organisms such as viruses, bacteria and parasites, as well as altered cells such as tumor cells and autoreactive immune cells. As utilized herein, a pathogenic agent is considered to be "inhibited" if either the growth or spread of the pathogenic agent is slowed, or if the pathogenic agent itself is destroyed.

As noted above, the present invention provides compositions and methods which utilize Herpesviridae thymidine kinase mutants. Briefly, thymidine kinase mutants of the present invention may be prepared from a wide variety of Herpesviridae thymidine kinases, including for example both primate herpesviruses, and nonprimate herpesviruses such as avian herpesviruses. Representative examples of suitable herpesviruses include Herpes Simplex Virus Type 1 (McKnight et al., *Nuc. Acids Res* 8:5949-5964, 1980), Herpes Simplex Virus Type 2 (Swain and Galloway, *J. Virol.* 46:1045-1050, 1983), Varicella Zoster Virus (Davison and Scott, *J. Gen. Virol.* 67:1759-1816, 1986), marmoset herpesvirus (Otsuka and Kit, *Virology* 135:316-330, 1984), feline herpesvirus type 1 (Nunberg et al., *J. Viral.* 63:3240-3249, 1989), pseudorabies virus (Kit and Kit, U.S. Pat. No. 4,514,497, 1985), equine herpesvirus type 1 (Robertson and Whalley, *Nuc. Acids Res.* 16:11303-11317, 1988), bovine herpesvirus type 1 (Mittal and Field, *J. Virol* 70:2901-2918, 1989), turkey herpesvirus (Martin et al., *J. Virol.* 63:2847-2852, 1989), Marek's disease virus (Scott et al., *J. Gen. Virol.* 70:3055-3065, 1989), herpesvirus saimiri (Honess et al., *J. Gen. Virol.* 70:3003-3013, 1989) and Epstein-Barr virus (Baer et al., *Nature* (London) 310:207-311, 1984).

Such herpesviruses may be readily obtained from commercial sources such as the American Type Culture Collection ("ATCC", Rockville, Md.). Deposits of certain of the above-identified herpesviruses may be readily obtained from the ATCC, for example: ATCC No. VR-539 (Herpes simplex type 1); ATCC Nos. VR-734 and VR-540 (Herpes Simplex type 2); ATCC No. VR-586 (Varicella Zoster Virus); ATCC No. VR-783 (Infectious laryngothracheitis); ATCC Nos. VR-624 VR-987, VR-2103, VR-2001, VR-2002, VR-2175, VR-585 (Marek's disease virus); ATCC Nos. VR-584B and VR-584B (turkey herpesvirus); ATCC Nos. VR-631 and VR-842 (bovine herpesvirus type 1); and ATCC Nos. VR-2003, VR-2229 and VR-700 (equine herpesvirus type 1). Herpesviruses may also be readily isolated and identified from naturally occurring sources (e.g., from an infected animal).

Any of the above-cited herpesviruses (as well as other members of the Herpesviridae) may be readily utilized in order to prepare thymidine kinase mutants of the present invention. Briefly, one primary region which is believed to be responsible for nucleoside binding is found in the area surrounding Sites 3 and 4 (see Balasubramaniam et al., *J. Gen. Vir.* 71:2979-2987, 1990). These sites are characterized by highly conserved regions, and consist of the motif -DRH- (for Site 3), and -C(Y/F)P- (for Site 4). Although the numbering of nucleic acids may change substantially from one herpesvirus to another, as utilized herein, reference will be made to positions relative to the DRH nucleoside binding site. For example, for Herpes Simplex Virus type 1 (McKnight et al., *Nucl. Acids Res.* 8:5949-5964, 1980), this site may be found at amino acids 162, 163 and 164. DRH nucleoside binding sites for other representative herpesviruses include: 163, 164 and 165 for Herpes Simplex Virus type 2; 129, 130 and 131 for Varicella Zoster Virus; 130, 131 and 132 for Marmoset herpesvirus; and 148, 149 and 150 for Epstein-Barr virus.

For herpesviruses which have not been previously sequenced, the DRH nucleoside binding site may be readily identified by sequencing the nucleic acid sequence encoding the enzyme, or by amino acid sequencing the enzyme itself, followed by alignment of the sequence to other known herpesvirus sequences (see Balasubramanian, ibid.). To the extent that more than one -DRH- motif is identified, the proper motif may be readily identified by, for example, crystal structure analysis (Sanderson et al., *J. Mol. Biol.* 202:917-919, 1988; Montfort et al., *Biochem* 29(30):6964-6977, 1990; Hardy et al., *Science* 235:448-455, 1987), or crosslinking studies (Knoll et al., *Bioch. Biophys. Acta* 1121:252-260, 1992).

The thymidine kinase gene from the selected herpesvirus may then be readily isolated and mutated as described below, in order to construct nucleic acid molecules encoding a thymidine kinase enzyme comprising one or more mutations which increases a biological activity of the thymidine kinase, as compared to unmutated thymidine kinase. As utilized herein, it should be understood that "unmutated thymidine kinase" refers to native or wild-type thymidine kinase such as that described by McKnight et al. (*Nucl. Acids Res.* 8:5949-5964, 1980). The biological activity of such kinases may be readily determined utilizing any of the assays which are described herein, including for example, determination of the rate of nucleoside analogue uptake, determination of the rate of nucleoside or nucleoside analogue phosphorylation (see Examples 2-4). In addition, thymidine kinase mutants may be readily selected which are characterized by other biological properties, such as thermostability (see Examples 2-4), and protein stability.

A wide variety of thymidine kinase mutations are contemplated within the scope of the present invention. For example, within one embodiment of the invention, isolated nucleic acid molecules are provided which encode a Herpesviridae thymidine kinase enzyme comprising one or more mutations, at least one of the mutations encoding an amino acid substitution located toward the N-terminus from the DRH nucleoside binding site. Briefly, any amino acid position toward the N-terminus of the DRH nucleoside binding site may be substituted for another amino acid given the disclosure provided herein. Representative amino acids which may be substituted (and their one letter symbols) include alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), and valine (V).

For example, within one embodiment of the invention, isolated nucleic acid molecules are provided which encode a Herpesviridae thymidine kinase enzyme comprising at least three mutations, at least two of the mutations being amino acid substitutions located toward the N-terminus from a DRH nucleoside binding site (e.g., 1, 2 or 3 amino acids toward the N-terminus), and at least one mutation located toward the C-terminus from a DRH nucleoside binding site (e.g., 4 or 5 amino acids toward the C-terminus) which increases a biological activity of the thymidine kinase, as compared to unmutated thymidine kinase. Briefly, an amino acid in any of these positions may be substituted for another amino acid given the disclosure provided herein. Representative amino acids which may be substituted (and their one letter symbols) include alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), and valine (V). With reference to TK mutants having at least two mutations toward the N-terminus and at least one mutation toward the C-terminus from a DRH site, preferred amino acids that may be substituted for amino acids of a wild-type sequence include alanine (A), asparagine (N), isoleucine (I), leucine (L), methionine (M), phenylalanine (F), tyrosine (Y), and valine (V).

Within another embodiment of the invention, nucleic acid molecules are provided which encode thymidine kinase mutants either with one or more amino acid substitutions within the Q substrate binding domain, or with one or more amino acid substitutions within an expanded region that includes the Q substrate binding domain and an additional 11 amino acid residues located toward the N-terminus ("the expanded Q substrate binding domain"). Representative amino acids which may be substituted (and their one letter symbols) include alanine (A), arginine (R), asparagine (N), aspartic acid (D), glutamine (Q), glutamic acid (E), glycine (G), histidine (H), lysine (K), methionine (M), phenylalanine (F), proline (P), serine (S), threonine (T), tryptophan (W), and tyrosine (Y).

Within another embodiment, nucleic acid molecules are provided which encode thymidine kinase mutants having with one or more amino acid substitutions within the Q substrate binding domain or within the expanded Q substrate binding domain, and at least one additional amino acid substitution located from two to six positions toward the N-terminus from the DRH nucleoside binding site. Representative amino acids which may be substituted include alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), and valine (V).

Within other embodiments, nucleic acid molecules are provided which encode thymidine kinase mutants having with one or more amino acid substitutions within the Q substrate binding domain or within the expanded Q substrate binding domain, and at least one additional amino acid substitution located seven positions toward the N-terminus from the DRH nucleoside binding site. Representative amino acids which may be substituted include arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), and valine (V).

Within other aspects of the invention, nucleic acid molecules are provided which encode thymidine kinase mutants having with one or more amino acid substitutions within the Q substrate binding domain or within the expanded Q substrate binding domain, and at least one additional mutation, as described by Dedieu et al., international publication No. WO 95/14102, which is hereby incorporated by reference.

Within another aspect of the present invention, nucleic acid molecules are provided which encode thymidine kinase mutants having with one or more amino acid substitutions within the Q substrate binding domain or within the expanded Q substrate binding domain, and at least one additional amino acid substitution within the DRH nucleoside binding site. Within one embodiment of the invention, the asparatic acid in the DRH nucleoside binding site is substituted with other amino acids, including for example, alanine (A), arginine (R), asparagine (N), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), and valine (V). Within another embodiment of the invention, the arginine in the DRH nucleoside binding site is substituted with other amino acids, including for example, alanine (A), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), and valine (V).

Within other aspects of the present invention, nucleic acid molecules are provided which encode thymidine kinase enzymes comprising two or more mutations which increase a biological activity of the thymidine kinase enzyme, wherein the mutants have one or more amino acid substitutions within the Q substrate binding domain or within the expanded Q substrate binding domain, and one or more amino acid substitutions located 1, 2 or 3 amino acids toward the N-terminus from the DRH nucleoside binding site, and/or one or more substitutions located 4, 5 or 6 amino acids toward the C-terminus from the DRH nucleoside binding site, or located 1, 2 or 3 amino acids toward the N-terminus from the CYP nucleoside binding site (see FIG. 14).

Within yet another embodiment of the invention, thymidine kinase mutants are characterized by having one or more amino acid substitutions within the Q substrate binding domain or within the expanded Q substrate binding domain, and by having the histidine in the DRH nucleoside binding site substituted with any other amino acid, including for example, alanine (A), arginine (R), asparagine (N), aspartic acid (D), cysteine (C), glutamine (Q), glutamic acid (E), glycine (G), isoleucine (I), leucine (L), lysine (K), methionine (M), phenylalanine (F), proline (P), serine (S), threonine (T), tryptophan (W), tyrosine (Y), and valine (V).

Within other aspects of the present invention, nucleic acid molecules are provided which encode thymidine kinase enzymes comprising two or more mutations which increase a biological activity of the thymidine kinase enzyme, wherein one or more amino acid substitutions are located within the Q substrate binding domain or within the expanded Q substrate binding domain, and wherein at least one mutation encodes an amino acid substitution located from 1 to 11 positions toward the C-terminus from the DRH nucleoside binding site. These amino acids may be substituted with other amino acids, including for example, alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), and valine (V).

Within another aspect of the present invention, nucleic acid molecules are provided which encode thymidine kinase enzymes comprising one or more mutations which increase a biological activity of the thymidine kinase enzyme, wherein one or more amino acid substitutions are located within the Q substrate binding domain or within the expanded Q substrate binding domain, and wherein at least one mutation encodes an amino acid substitution located from 12 to "v" positions toward the C-terminus from the DRH nucleoside binding site, wherein "v" is any integer greater than 13 (and generally less than 202). These amino acids may be readily substituted with other amino acids, including for example, alanine (A), arginine (R), asparagine (N), aspartic acid 04 cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), and valine (V).

Within various aspects, nucleic acid molecules of the present invention may encode several amino acid mutations. For example, within one preferred embodiment, thymidine kinase mutants are provided which encode mutations with 1, 2, 3, 4, 5 or more amino acid substitutions, as well as in-frame deletions. Example of such mutants include P155A/F161V, P155A/F161C, P155A/D162E, I160L/F161L/A168V/L169M and F161L/A168V/L169Y/L170C.

As described herein, mutagenesis of nucleotides encoding the residues surrounding Sites 3 and 4 of HSV-1 TK has lead to improvements in the kinetic parameters (Km) towards nucleoside prodrugs. A new and distinct region has been recently identified to participate in nucleoside binding that resides within amino acid residues 112-132. The region encoding residues 112-132 of HSV-1 TK was implicated in substrate (or dTMP) binding by photoaffinity labeling using a 32P-azido-dUMP probe (Rechtin et al., *Anal. Biochem.* 237: 135-140, 1996). This initial identification was supported by the observed proximity of these residues to bound substrate (thymidine or ganciclovir), as determined by X-ray crystallography studies (Wild et al., *FEBS Lett.* 368:289-292, 1995; Brown et al., *Nature Struct. Biol.* 2:876-881, 1995). Since the glutamine ("Q") residue shows significant conservation in TK enzymes from a wide variety of sources (see, for example, Balasubramaniam et al., *J. Gen. Virol.* 71:2979-2987, 1990), the region of amino acid residues 112-132 is designated as the "Q substrate binding domain."

Due to its role in substrate binding, this region is an excellent target for mutagenizing and selecting clones with altered substrate specificities. Such mutants would improve the efficacy and specificity of suicide gene therapy in the presence of specific prodrugs. Moreover, these mutant enzymes can be used for cell lineage ablation, restenosis and selection of homologous recombinants.

Accordingly, the present invention includes nucleic acid molecules encoding forms of TK with at least one mutation within the Q substrate binding domain. The present invention also includes nucleic acid molecules encoding truncated TK enzymes having at least one mutation within the Q substrate binding domain. The present invention further includes mutant TK-encoding nucleic acid molecules with at least one modification in a subregion of the Q substrate binding domain, such as within amino acid residues 123-132, or with at least one mutation in an expanded region that includes the Q substrate binding domain and about 11 additional amino acids toward the N-terminus, (e.g., within amino acid residues 101-132). As an illustration, Example 10 describes methods for the mutagenesis of the region encoding amino acids 112-132 of HSV-1 TK. In this example, TK mutants were constructed that contained 1, 2, 3, 4, 5, 6, 7, 8, 9, 10, 11, 12, 13, 14, 15, 16, 17, 18, 19, 20, or 21 mutations within amino acid residues 112-132.

Identification of the Q substrate binding domain, which is distinct from the DRH nucleoside binding site, enables the construction of numerous thymidine kinase mutations. Such TK mutants include those having amino acid substitutions in the Q substrate binding domain with any of the following representative amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. Functionally, TK mutants having an alteration in the Q substrate binding domain are characterized by an increased biological activity of thymidine kinase, as compared with unmutated thymidine kinase.

Although Example 10 illustrates mutagenesis of the HSV-1 TK Q substrate binding domain, the present invention also includes a variety of thymidine kinase mutants having alterations in this domain. Identification of a Q substrate binding domain in various TK enzymes can be achieved by aligning a TK amino acid sequence with the HSV-1 TK sequence. For example, Balasubramaniam et al., *J. Gen. Virol.* 71:2979-2987 (1990), provide such an alignment of the following TK enzymes: HSV-1, HSV-2, marmoset herpesvirus, varicella-zoster virus, feline herpesvirus, pseudorabies virus, equine herpesvirus type 1, bovine herpesvirus type 1, turkey herpesvirus, Marek's disease virus, herpesvirus saimiri, and Epstein-Barr virus.

Alternatively, photoaffinity labeling can be used to identify analogous Q substrate binding domains, using the methods described by Rechtin et al., *Anal. Biochem.* 237:135-140 (1996), which is incorporated by reference. In addition, the identification of a Q substrate binding domain can be verified by crystal structure analysis using standard techniques (see, for example, Wild et al., *FEBS Lett.* 368:289292, 1995; Brown et al., *Nature Struct. Biol.* 2:876-881, 1995; De Winter and Herdewijn, *J. Med. Chem.* 39:4727-4737, 1996). In sum, well-known methods can be used to identify analogous Q substrate binding domains in various thymidine kinases. Preferred sources for mutation of the Q substrate binding domain are Herpesviridae thymidine kinases.

The present invention also provides TK mutants that have mutations in the Q substrate binding domain (or, in the expanded Q substrate binding domain) in addition to at least one mutation associated with the DRH nucleoside binding site, as described above. For example, the present invention contemplates TK mutants having at least one amino acid substitution in the Q substrate binding domain (or, in the expanded Q substrate binding domain) and (1) at least two amino acid substitutions located toward the N-terminus from a DRH nucleoside binding site (e.g., one, two or three amino acids toward the N-terminus) and at least one mutation located toward the C-terminus from a DRH nucleoside binding site (e.g., four or five amino acids toward the C-terminus), (2) one or more amino acid substitutions located from one to seven amino acids toward the N-terminus from a DRH nucleoside binding site, (3) amino acid substitutions that are located two to six positions toward N-terminus from the DRH nucleoside binding site, and (4) one or more amino acid substitutions within the DRH nucleoside binding site. Again, such TK mutants are characterized by an increased biological activity of thymidine kinase, as compared with unmutated thymidine kinase.

Any of the above-described thymidine kinase mutants may be readily screened for increased biological activity, given the assays described herein and below in the Examples.

Construction of Thymidine Kinase Mutants

Thymidine kinase mutants of the present invention may be constructed using a wide variety of techniques. For example, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene having particular codons altered according to the substitution, deletion, or insertion required. Deletion or truncation derivatives of thymidine kinase mutants may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al. (*Molecular cloning: A Laboratory Manual*, 2d Ed., Cold Spring Harbor Laboratory Press, 1989).

Thymidine kinase mutants may also be constructed utilizing techniques of PCR mutagenesis, chemical mutagenesis (Drinkwater and Klinedinst, *PNAS* 83:3402-3406, 1986), by forced nucleotide misincorporation (e.g., Liao and Wise *Gene* 88:107-111, 1990), or by use of randomly mutagenized oligonucleotides (Horwitz et al., *Genome* 3:112-117, 1989). Preferred methods for constructing thymidine kinase mutants are set forth in more detail below in the Examples.

HSVTK Vectors

Within the context of the present invention, the term "thymidine kinase mutant" should be understood to include not only the specific protein described herein (as well as the nucleic acid sequences which encode these proteins), but derivatives thereof which may include various structural forms of the primary protein which retain biological activity. For example, a thymidine kinase mutant may be in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance the increased biological activity of the mutant. Due to code degeneracy, for example, there may be considerable variation in nucleotide sequences encoding the same amino acid sequence.

Other derivatives of the thymidine kinase mutants disclosed herein include conjugates of thymidine kinase mutants along with other proteins or polypeptides. This may be accomplished, for example, by the synthesis of N-terminal or C-terminal fusion proteins which may be added to facilitate purification or identification of thymidine kinase mutants (see U.S. Pat. No. 4,851,341, see also, Hopp et al., *Bio/Technology* 6:1204, 1988.)

Within one embodiment of the present invention, truncated derivatives of thymidine kinase mutants are provided. For example, site-directed mutagenesis may be readily performed in order to delete the N-terminal 45 amino acids of a thymidine kinase mutant, thereby constructing a truncated form of the mutant which retains its biological activity.

Mutations in nucleotide sequences constructed for expression of derivatives of thymidine kinase mutants should preserve the reading frame phase of the coding sequences. Furthermore, the mutations will preferably not create complementary regions that could hybridize to produce secondary mRNA structures, such as loops or hairpins, which would adversely affect translation of the receptor mRNA. Such derivatives may be readily constructed using a wide variety of techniques, including those discussed above.

As noted above, the present invention provides recombinant vectors which include either synthetic, or cDNA-derived nucleic acid molecules encoding thymidine kinase mutants or derivatives thereof, which are operably linked to suitable transcriptional or translational regulatory elements. Suitable regulatory elements may be derived from a variety of sources, including bacterial, fungal, viral, mammalian, insect, or plant genes. Selection of appropriate regulatory elements is dependent on the host cell chosen, and may be readily accomplished by one of ordinary skill in the art. Examples of regulatory elements include: a transcriptional promoter and enhancer or RNA polymerase binding sequence, a ribosomal binding sequence, including a translation initiation signal.

Nucleic acid molecules which encode any of the thymidine kinase mutants described above may be readily expressed by a wide variety of prokaryotic and eukaryotic host cells, including bacterial, mammalian, yeast or other fungi, viral, insect, or plant cells. Methods for transforming or transfecting such cells to express foreign DNA are well known in the art (see, e.g., Itakura et al., U.S. Pat. No. 4,704,362; Hinnen et al., *PNAS USA* 75:1929-1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. *Molecular Cloning: A Laboratory Manual,* 2nd edition, Cold Spring Harbor Laboratory Press, 1989; for plant cells see Czako and Marton, *Plant Physiol.* 104:1067-1071, 1994; and Paszkowski et al., *Biotech.* 24:387392, 1992).

Bacterial host cells suitable for carrying out the present invention include *E. coli, B. subtilis, Salmonella typhimurium,* and various species within the genus' *Pseudomonas, Streptomyces,* and *Staphylococcus,* as well as many other bacterial species well known to one of ordinary skill in the art. Representative examples of bacterial host cells include DH5α (Stratagene, LaJolla, Calif.).

Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., *Nature* 275:615, 1978), the T7 RNA polymerase promoter (Studier et al., *Meth. Enzymol.* 185:60-89, 1990), the lambda promoter (Elvin et al., *Gene* 87:123-126, 1990), the trp promoter (Nichols and Yanofsky, *Meth. in Enzymology* 101:155, 1983) and the tac promoter (Russell et al., *Gene* 20: 231, 1982). Representative selectable markers include various antibiotic resistance markers such as the kanamycin or ampicillin resistance genes. Many plasmids suitable for transforming host cells are well known in the art, including among others, pBR322 (see Bolivar et al., *Gene* 2:95, 1977), the pUC plasmids pUC18, pUC19, pUC118, pUC119 (see Messing, *Meth. in Enzymology* 101:20-77, 1983 and Vieira and Messing, *Gene* 19:259-268, 1982), and pNH8A, pNH16a, pNH18a, and Bluescript M13 (Stratagene, La Jolla, Calif.).

Yeast and fungi host cells suitable for carrying out the present invention include, among others *Saccharomyces pombe, Saccharomyces cerevisiae,* the genera *Pichia* or *Kluyveromyces* and various species of the genus *Aspergillus.* Suitable expression vectors for yeast and fungi include, among others, $YC_p50$ (ATCC No. 37419) for yeast, and the amdS cloning vector pV3 (Turnbull, *Bio/Technology* 7:169, 1989). Protocols for the transformation of yeast are also well known to those of ordinary skill in the art. For example, transformation may be readily accomplished either by preparation of spheroplasts of yeast with DNA (see Hinnen et al., *PNAS USA* 75:1929, 1978) or by treatment with alkaline salts such as LiCl (see Itoh et al., *J. Bacteriology* 153:163, 1983). Transformation of fungi may also be carried out using polyethylene glycol as described by Cullen et al. (*Bio/Technology* 5:369, 1987).

Mammalian cells suitable for carrying out the present invention include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter, as well as other transcriptional and translational control sequences. Common promoters include SV40, MMTV, metallothionein-1, adenovirus E1a, Cytomegalovirus Immediate Early Promoter, and the Cytomegalovirus Immediate Late Promoter.

Protocols for the transfection of mammalian cells are well known to those of ordinary skill in the art. Representative methods include calcium phosphate mediated transfection, electroporation, lipofection, retroviral, adenoviral and protoplast fusion-mediated transfection (see Sambrook et al., supra).

Thymidine kinase mutants may be prepared by culturing the host/vector systems described above, in order to express the recombinant thymidine kinase mutants. Recombinantly produced thymidine kinase mutants may be further purified as described in more detail below.

As noted above, the present invention also provides a variety of both viral and non-viral vectors which are suitable for directing the expression of the nucleic acid molecules described above. Within one aspect of the invention, viral vectors are provided which comprise a promoter that directs the expression of an isolated nucleic acid molecule which encodes a thymidine kinase mutant as described above. A wide variety of promoters may be utilized within the context of the present invention, including for example, promoters such as MoMLV LTR, RSV LTR, Friend MuLV LTR, Adenoviral promoter (Ohno et al., *Science* 265: 781-784, 1994), Neomycin phosphotransferase promoter/enhancer, late parvovirus promoter (Koering et al., *Hum. Gene Therap.* 5:457-463, 1994), Herpes TK promoter, SV40 promoter, Metallothionein IIa gene enhancer/promoter, Cytomegalovirus Immediate Early Promoter, and the Cytomegalovirus Immediate Late Promoter. Within particularly preferred embodiments of the invention, the promoter is a tissue-specific promoter (see e.g., WO 91/02805; EP 0,415,731; and WO 90/07936). Representative examples of suitable tissue specific promoters include the tyrosinase related promoters (TRP-1 and TRP-2, Vile and Hart, *Canc. Res.* 53:962-967, 1993), DF3 enhancer (for breast cells, see Manome et al., *Canc. Res.* 54:5408-5413, 1994), SLPI promoter (secretory leucoprotease inhibitor—expressed in many types of carcinomas, see Garver et al, *Gene Therapy* 1:46-50, 1994), TRS (tissue specific regulatory sequences, see Dynan and Tjian, *Nature* 316: 774-778, 1985), albumin and α fetoprotein promoters (specific for normal hepatocytes and transformed hepatocytes, respectively), the carcino-embryonic antigen promoter (for use in transformed cells of the gastrointestinal tract, lung, breast and other tissues), the tyrosine hydroxylase promoter (for melanocytes), choline acetyl transferase or neuron specific enolase promoters for use in neuroblastomas, the regulatory sequence for glial fibroblastomas, the tyrosine hydroxylase promoter, c-erb B-2 promoter, PGK promoter, PEPCK promoter, whey acidic promoter (breast tissue), and casein promoter (breast tissue) and the adipocyte P2 promoter (Ross et al., *Genes & Dev.* 1318-1324, 1993; and Lowell et al., *Nature* 366:740-742, 1993). In addition to the above-noted promoters, other viral-specific promoters (e.g., retroviral promoters (including those noted above, as well as others such as HIV promoters), hepatitis, herpes (e.g., EBV), and bacterial, fungal or parasitic (e.g., malarial)-specific promoters may be utilized in order to target a specific cell or tissue which is infected with a virus, bacteria, fungus or parasite.

Thymidine kinase mutants of the present invention may be expressed from a variety of viral vectors, including for example, adenoviral vectors (e.g., Kass-Eisler et al., *PNAS* 90(24):11498-502, 1993; Kolls et al., *PNAS* 91(1):215-219, 1994; Li et al., *Hum Gene Ther.* 4(4):403-409, 1993; Vincent et al., *Nat. Genet.* 5(2):130-134, 1993; and Zabner et al., *Cell* 75(2):207-216, 1993; WO 94/26914, WO 93/9191), adenovirus-associated viral vectors (Flotte et al., *PNAS* 90(22): 10613-10617, 1993), alphaviruses such as Semliki Forest Virus and Sindbis Virus (Hertz and Huang, *J. Vir.* 66(2):857-864, 1992; Raju and Huang, *J. Vir.* 65(5):2501-2510, 1991; Xiong et al., *Science* 243:1188, 1989; U.S. Pat. No. 5,091, 309; WO 92/10578; WO 95/07994); baculovirus vectors; herpes viral vectors (e.g. U.S. Pat. Nos. 4,769,331, 4,859,587, 5,288,641 and 5,328,688; and PCT publication Nos. WO 94/14971 and WO 95/04139), parvovirus vectors (Koering et al., *Hum. Gene Therap.* 5:457-463, 1994), pox virus vectors (Ozaki et al., *Biochem. Biophys. Res. Comm.* 193(2):653-660, 1993; and Panicali and Paoletti, *PNAS* 79:4927-4931, 1982), pox viruses, such as canary pox virus or vaccinia virus (Fisher-Hoch et al., *PNAS* 86:317-321, 1989; Flexner et al., *Ann. N.Y. Acad. Sci.* 569:86-103, 1989; U.S. Pat. Nos. 4,603, 112, 4,769,330 and 5,017,487; WO 89/01973); and retroviruses (e.g., Baba et al., *J. Neurosurg* 79:729-735, 1993; Ram et al., *Cancer Res.* 53:83-88, 1993; Takamiya et al., *J. Neurosci. Res* 33:493-503, 1992; Vile and Hart, *Cancer Res.* 53:962-967, 1993; Vile and Hart, *Cancer Res.* 53:3860-3864, 1993; U.S. Pat. No. 5,219,740; EP 0,415,731; WO 90/07936; WO 91/0285, WO 94/03622; WO 93/25698; WO 93/25234; WO 93/11230; WO 93/10218). Within various embodiments, either the viral vector itself, or a viral particle which contains the viral vector may be utilized in the methods and compositions described below.

In addition to viral vectors, non-viral vectors systems, or systems which contain portions of a viral vector (e.g., which control transcription, translation, or viral entry into a cell) may be utilized to deliver nucleic acid sequences of the present invention. Representative example of such systems a variety of nucleic acid based transcription systems (e.g., based on T7 or SP6 promoters, see generally, Li et al., "Tumor regression in Nude Mice by Direct Injection of a Nonviral Cytoplasmic Gene Expression Vector Containing a Thymidine Kinase Gene" p. 179, Cold Spring Harbor Meeting in Gene Therapy, Sep. 21-25, 1194; WO 95/07994). Such vector systems may be administered and prepared as described herein (e.g., in liposomes, condensed with polycations, or linked to a ligand).

Vectors of the present invention may contain or express a wide variety of additional nucleic acid molecules in addition to a thymidine kinase nucleic acid molecule as described above. For example, the viral vector may express a lymphokine, antisense sequence, toxin or "replacement" protein (e.g., adenosine deaminase). Representative examples of lymphokines include IL-1, IL-2, IL-3, IL-4, IL-5, IL-6, IL-7, IL-8, IL-9, IL-10, IL-11, IL-12, IL-13, IL-14, GM-CSF, G-CSF, M-CSF, alpha-interferon, beta-interferon, gamma interferon, and tumor necrosis factors. Representative examples of antisense sequences include antisense myc, antisense p53, antisense ras, as well as antisense sequences which block the expression or production of viruses such as HIV, HBV and HCV. Representative examples of toxins include: ricin, abrin, diphtheria toxin, cholera toxin, gelonin, pokeweed antiviral protein, tritin, *Shigella* toxin, and *Pseudomonas* exotoxin A.

Within preferred embodiments of the invention, one or more genes which encode proteins that facilitate or increase the biological activity of thymidine kinase may be included with, and expressed by the vectors described herein. For example, within one embodiment of the invention, nucleic acid molecules which encode DNA polymerase (e.g., a Herpes DNA polymerase) and/or guanylate kinase (Konrad, *J. Biol. Chem.* 267(36):25652-25655, 1992; Miller and Miller, *J. Biol. Chem.* 255(15):7204-7207, 1980) are expressed either from one or several separate promoters (e.g., from multiple internal ribosome binding sites) in addition to a thymidine kinase enzyme (either wild type, or thymidine kinase mutants as described above). Representative examples of such embodiments are set forth in more detail below in Examples 7 and 11. It should be understood that although certain nucleic acid molecules are disclosed which encode DNA polymerase or guanylate kinase, that the present invention is not so limited. Indeed, as discussed above with respect to thymidine kinase mutants, a wide variety of nucleic acid molecules are considered to be included within the scope of the present invention which encode DNA polymerase or guanylate kinase activity (e.g., truncated nucleic acid molecules or nucleic acid molecules which are degenerate with respect to the encoded amino acid sequence).

Thymidine kinase mutants may also be expressed in non-human transgenic animals such as mice, rats, rabbits, sheep, dogs and pigs (see Hammer et al. (*Nature* 315:680-683, 1985), Palmiter et al. (*Science* 222:809-814, 1983), Brinster et al. (*Proc. Natl. Acad. Sci. USA* 82:4438-4442, 1985), Palmiter and Brinster (*Cell* 41:343-345, 1985) and U.S. Pat. No. 4,736,866). Briefly, an expression unit, including a nucleic acid molecule to be expressed together with appropriately positioned expression control sequences, is introduced into pronuclei of fertilized eggs, for example, by microinjection. Integration of the injected DNA is detected by blot analysis of DNA from tissue samples. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al., 1983, ibid), which allows regulated expression of the transgene.

Host Cells

The above described nucleic acid molecules which encode thymidine kinase mutants of the present invention (or the vectors which contain and/or express these mutants) may readily be introduced into a wide variety of host cells. Representative examples of such host cells include plant cells, eukaryotic cells, and prokaryotic cells. Within preferred embodiments, the nucleic acid molecules are introduced into cells from a vertebrate or warm-blooded animal, such as a human, macaque, dog, cow, horse, pig, sheep, rat, hamster, mouse or fish cell, or any hybrid thereof.

The nucleic acid molecules (or vectors) may be introduced into host cells by a wide variety of mechanisms, including for example calcium phosphate-mediated transfection (Wigler et al., *Cell* 14:725, 1978), lipofection; gene gun (Corsaro and Pearson, *Somatic Cell Gen.* 7:603, 1981; Graham and Van der Eb, *Virology* 52:456, 1973), electroporation (Neumann et al., *EMBO J.* 1:841-845, 1982), retroviral, adenoviral, protoplast fusion-mediated transfection or DEAE-dextran mediated transfection (Ausubel et al., (eds.), *Current Protocols in Molecular Biology*, John Wiley and Sons, Inc., NY, N.Y., 1987).

Construction of Guanylate Kinase

Thymidine Kinase Fusion Proteins

There are several approaches for improving the net efficiency of suicide gene therapy. As described above, one approach is to create novel TK enzymes that efficiently convert systemically delivered prodrugs into cytotoxic compounds. Another strategy is to facilitate the subsequent metabolism of the prodrug to its toxic form by introducing the gene encoding the enzyme responsible for the second step in the nucleotide metabolic pathway of prodrug activation, guanylate kinase, in combination with thymidine kinase. Unlike the cellular thymidine kinase, the HSV TK can perform the initial phosphorylation of prodrugs, such as GCV and ACV, to their monophosphorylated states. Cellular kinases further phosphorylate the nucleotide to the triphosphate which then inhibits chain elongation by DNA polymerase after insertion into the nascent DNA chain and subsequently leads to cell death. Guanylate kinase (gmk), the second step in the prodrug activation pathway, appears to be rate limiting in vivo. Example 11 illustrates methods for the construction of mammalian expression vectors that produce both gmk and TK enzymes.

In yet another approach, fusion proteins can be constructed that express both gmk and TK enzyme activities, providing the expression of two enzyme functions from a single promoter and a single cistron. In this way, the use of a fusion protein for gene therapy would eliminate the requirement for two promoters, and would eliminate the associated reduction in prodrug activation due to the differences in promoter strength. Moreover, fusion proteins are advantageous for gene therapy vectors which cannot tolerate large pieces of foreign DNA, such as AAV vectors.

Example 12 describes the construction of two gmk-TK fusion proteins. Although the exemplified vectors contain a TK gene fused to the 3'-end of a gmk gene, suitable fusion proteins can be produced with vectors having a gmk gene fused to the 3'-end of a TK gene. Example 12 also illustrates that such fusion proteins need not contain the entire amino acid sequence of a kinase gene. That is, nucleic acid molecules encoding a truncated gmk and/or a truncated TK can be used to express fusion proteins of the present invention. However, such truncated kinases must possess the appropriate biological activity, as defined above. The biological activity of a truncated gmk or a truncated TK can be determined using the enzyme assays described herein.

General methods for producing fusion proteins are well-known to those of skill in the art. See, for example, Ausubel et al. (eds.), *Short Protocols in Molecular Biology,* 3d Edition, pages 16-16 to 16-37 (John Wiley & Sons, Inc. 1995). Example 11 describes methods for obtaining both human and murine gmk clones (also see Brady et al., *J. Biol. Chem.* 271:16734-16740, 1996). Those of skill in the art can obtain nucleic acid molecules encoding gmk from a variety of sources using standard techniques. For example, Konrad, *J. Biol. Chem.* 267:25652-25655 (1992), describes the isolation of gmk sequences from *Saccharomyces cerevisiae,* Gaidarov et al., *FEBS Lett.* 335:81-84 (1993), disclose bovine guanylate kinase sequences, Zschocke et al. *Eur. J. Biochem.* 213: 263-269 (1993), provide porcine guanylate kinase sequences, and an *E. coli* guanylate kinase sequence is provided by Gentry et al., *J. Biol. Chem.* 268:14316-14321 (1993). In addition, nucleic acid molecules encoding guanylate kinase enzymes are commercially available. For example, DNA molecules encoding *Mycoplasma genitalium* gmk can be obtained from the American Type Culture Collection (ATCC No. 623592). Suitable TK genes include both known TK genes and the TK mutants of the present invention. Sources for TK genes, suitable expression vectors, and suitable host cells are described above.

Preparation of Antibodies

Antibodies to the thymidine kinase mutants, guanylate kinase protein, or fusion proteins described herein may readily be prepared given the disclosure provided herein. Within the context of the present invention, antibodies are understood to include monoclonal antibodies, polyclonal antibodies, antibody fragments (e.g., Fab, and F(ab')$_2$) as well as portions thereof that may be produced by various recombinant methods. Antibodies are understood to be reactive against a thymidine kinase mutant or fusion protein if it binds with a $K_a$ of greater than or equal to $10^7$ M. As will be appreciated by one of ordinary skill in the art, antibodies may be developed which not only bind to a ligand such as a thymidine kinase mutant or fusion protein, but which also block or inhibit the biological activity of the mutant or fusion protein.

Briefly, polyclonal antibodies may be readily generated by one of ordinary skill in the art from a variety of warm-blooded animals such as horses, cows, various fowl, rabbits, mice, or rats. Briefly, a thymidine kinase mutant (or guanylate kinase enzyme, or fusion protein, if such antibodies are desired) is utilized to immunize the animal through intraperitoneal, intramuscular, intraocular, or subcutaneous injections, an adjuvant such as Freund's complete or incomplete adjuvant. Following several booster immunizations, samples of serum are collected and tested for reactivity to the thymidine kinase mutant (or guanylate kinase or fusion protein). Particularly preferred polyclonal antisera will give a signal on one of these assays that is at least three times greater than background. Once the titer of the animal has reached a plateau in terms of its reactivity to the thymidine kinase mutant, guanylate kinase enzyme, or fusion protein, larger quantities of antisera may be readily obtained either by weekly bleedings, or by exsanguinating the animal.

Monoclonal antibodies may also be readily generated using conventional techniques (see U.S. Pat. Nos. RE 32,011, 4,902,614, 4,543,439, and 4,411,993 which are incorporated herein by reference; see also *Monoclonal Antibodies, Hybridomas: A New Dimension in Biological Analyses,* Plenum Press, Kennett, McKeam, and Bechtol (eds.), 1980, and *Antibodies: A Laboratory Manual,* Harlow and Lane (eds.), Cold Spring Harbor Laboratory Press, 1988, which are also incorporated herein by reference).

Briefly, within one embodiment a subject animal such as a rat or mouse is injected with a thymidine kinase mutant, guanylate kinase enzyme, or fusion protein as described above. The thymidine kinase mutant, guanylate kinase enzyme, or fusion protein may be admixed with an adjuvant such as Freund's complete or incomplete adjuvant in order to increase the resultant immune response. Between one and three weeks after the initial immunization the animal may be reimmunized with another booster immunization, and tested for reactivity to the thymidine kinase mutant, guanylate kinase enzyme, or fusion protein using assays described above. Once the animal has plateaued in its reactivity to the mutant, it is sacrificed, and organs which contain large numbers of B cells such as the spleen and lymph nodes are harvested.

Cells which are obtained from the immunized animal may be immortalized by transfection with a virus such as the Epstein-Barr virus (EBV) (see Glasky and Reading, *Hybridoma* 8(4):377-389, 1989). Alternatively, within a preferred embodiment, the harvested spleen and/or lymph node cell suspensions are fused with a suitable myeloma cell in order to create a "hybridoma" which secretes monoclonal antibody. Suitable myeloma lines include, for example, NS-1 (ATCC No. TIB 18), and P3×63-Ag 8.653 (ATCC No. CRL 1580).

Following the fusion, the cells may be placed into culture plates containing a suitable medium, such as RPMI 1640, or DMEM (Dulbecco's Modified Eagles Medium) (JRH Biosciences, Lenexa, Kans.), as well as additional ingredients, such as Fetal Bovine Serum (FBS, i.e., from Hyclone, Logan, Utah, or JRH Biosciences). Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive against a thymidine kinase mutant, guanylate kinase enzyme, or fusion protein. A wide variety of assays may be utilized to determine the presence of antibodies which are reactive against the proteins of the present invention, including for example Countercurrent Immuno-Electrophoresis, Radioimmunoassays, Radioimmunoprecipitations, Enzyme-Linked Immuno-Sorbent Assays (ELISA), Dot Blot assays, Western Blots, immunoprecipitation, Inhibition or Competition Assays, and sandwich assays (see U.S. Pat. Nos. 4,376,110 and 4,486,530; see also *Antibodies: A Laboratory Manual*, Harlow and Lane (eds.), Cold Spring Harbor Laboratory Press, 1988). Following several clonal dilutions and reassays, a hybridoma producing antibodies reactive against the thymidine kinase mutant (or guanylate kinase enzyme or fusion protein) may be isolated.

Other techniques may also be utilized to construct monoclonal antibodies (see William D. Huse et al., "Generation of a Large Combinational Library of the Immunoglobulin Repertoire in Phage Lambda," *Science* 246:1275-1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728-5732, August 1989; see also Michelle Alting-Mees et al., "Monoclonal Antibody Expression Libraries: A Rapid Alternative to Hybridomas," *Strategies in Molecular Biology* 3:1-9, January 1990; these references describe a commercial system available from Stratacyte, La Jolla, Calif., which enables the production of antibodies through recombinant techniques). Briefly, mRNA is isolated from a B cell population, and utilized to create heavy and light chain immunoglobulin cDNA expression libraries in the kImmunoZap(H) and kImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid which allows high level expression of monoclonal antibody fragments from *E. coli*.

Similarly, portions of antibodies may also be constructed utilizing recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{Ha}$, $V_{Hb}$, $V_{Hc}$, $V_{Hd}$, $C_{Hl}$, $V_L$ and $C_L$ regions. These primers may be utilized to amplify heavy or light chain variable regions, which may then be inserted into vectors such as ImmunoZAP™ H or ImmunoZAP™ L (Stratacyte), respectively. These vectors may then be introduced into *E. coli* for expression. Utilizing these techniques, large amounts of a single-chain protein containing a fusion of the $V_H$ and $V_L$ domains may be produced (see Bird et al., *Science* 242:423-426, 1988). In addition, such techniques may be utilized to change a "murine" antibody to a "human" antibody, without altering the binding specificity of the antibody.

Once suitable antibodies have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

Labeling of Antibodies

Anti-thymidine kinase, anti-guanylate kinase, or anti-fusion protein antibodies which are described above may be labeled with a variety of molecules, including for example, fluorescent molecules, toxins, and radionuclides. Representative examples of fluorescent molecules include fluorescein, phycoerythrin, rodamine, Texas red and luciferase. Representative examples of toxins include ricin, abrin diphtheria toxin, cholera toxin, gelonin, pokeweed antiviral protein, tritin, *Shigella* toxin, and *Pseudomonas* exotoxin A. Representative examples of radionuclides include Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212. In addition, the antibodies described above may also be labeled or conjugated to one partner of a ligand binding pair. Representative examples include avidin-biotin, and riboflavin-riboflavin binding protein.

Methods for conjugating or labeling the anti-thymidine kinase, anti-guanylate kinase, or anti-fusion protein antibodies discussed above with the representative labels set forth above may be readily accomplished by one of ordinary skill in the art (see Trichothecene Antibody Conjugate, U.S. Pat. No. 4,744,981; Antibody Conjugate, U.S. Pat. No. 5,106,951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, *Methods In Enzymology*, Vol. 34, *Affinity Techniques, Enzyme Purification: Part B*, Jakoby and Wilchek (eds.), Academic Press, New York, p. 30, 1974; see also Wilchek and Bayer, "The Avidin-Biotin Complex in Bioanalytical Applications," *Anal. Biochem.* 171:1-32, 1988).

Pharmaceutical Compositions

As noted above, the present invention also provides a variety of pharmaceutical compositions (or medicaments), comprising one of the above-described thymidine kinase mutants, guanylate kinases, or fusion proteins (e.g. either the nucleic acid molecule, vector, or protein), along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

In addition, the pharmaceutical compositions of the present invention may be prepared for administration by a variety of different routes, including for example intraarticularly, intracranially, intradermally, intramuscularly, intraocularly, intraperitoneally, intrathecally, intravenously, subcutaneously or even directly into a tumor (for example, by stereotaxic injection). In addition, pharmaceutical compositions of the present invention may be placed within containers, along with packaging material which provides instructions regarding the use of such pharmaceutical compositions.

Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

METHODS

The present invention also provides methods for inhibiting a pathogenic agent in a warm-blooded animal, comprising administering to the warm-blood animal a vector (e.g., expression vector, viral vector, or viral particle containing a vector), as described above, such that the pathogenic agent is inhibited. Representative examples of pathogenic agents include autoimmune cells, tumor cells, cells which do not express or inappropriately express a particular gene, and cells infected with bacteria, viruses, or other intracellular parasites. As will be evident to one of skill in the art, the amount and frequency of administration will depend, of course, on such factors as the nature and severity of the indication being treated, the desired response, the condition of the patient, and so forth. Typically, the compositions may be administered by a variety of techniques, including for example intraarticularly, intracranially, intradermally, intramuscularly, intraocularly, intraperitoneally, intrathecally, intravenously, subcutaneously or even directly into a tumor (for example, by stereotaxic injection).

Within certain embodiments of the invention, the vectors which contain or express the nucleic acid molecules which encode thymidine kinase (and/or guanylate kinase) or fusion protein described above, or even the nucleic acid molecules themselves may be administered by a variety of alternative techniques, including for example administration of asialoosomucoid (ASOR) conjugated with poly (L-lysine) DNA complexes (Cristano et al., *PNAS* 92122-92126, 1993), DNA linked to killed adenovirus (Michael et al., *J. Biol. Chem.* 268(10):6866-6869, 1993; and Curiel et al., *Hum. Gene Ther.* 3(2):147-154, 1992), cytofectin-mediated introduction (DM-RIE-DOPE, Vical, Calif.), direct DNA injection (Acsadi et al., *Nature* 352:815-818, 1991); DNA ligand (Wu et al., *J. of Biol. Chem.* 264:16985-16987, 1989); lipofection (Felgner et al., *Proc. Natl. Acad. Sci. USA* 84:7413-7417, 1989); liposomes (Pickering et al., *Circ.* 89(1):13-21, 1994; and Wang et al., *PNAS* 84:7851-7855, 1987); microprojectile bombardment (Williams et al., *PNAS* 88:2726-2730, 1991); retrotransposons, transferrin-DNA complexes (Zenke), and direct delivery of nucleic acids which encode the enzyme itself either alone (Vile and Hart, *Cancer Res.* 53: 3860-3864, 1993), or utilizing PEG-nucleic acid complexes.

Within one aspect of the invention, methods are provided for inhibiting a tumor or cancer in a warm-blooded animal, comprising administering to the warm-blooded animal one of the vectors described above (or nucleic acid molecules which encode thymidine kinase mutants, guanylate kinase enzymes, or fusion proteins of the present invention), such that the tumor or cancer is inhibited. Within one embodiment, selected cells may be removed from a warm-blooded animal, one or more of the vectors described above introduced into the removed cells, and the cells reintroduced into the same or another warm-blooded animal. Within other embodiments, vectors or nucleic acid molecules which encode thymidine kinase (or mutants as described herein) or guanylate kinase or fusion protein may be separately administered or introduced. Within a further embodiment, such methods further comprise the step of administering a nucleoside analogue. Representative examples of such nucleoside analogues include ganciclovir, acyclovir, trifluorothymidine, 1-[2-deoxy, 2-fluoro, beta-D-arabino furanosyl]-5-iodouracil, ara-A, araT 1-beta-D-arabinofuranoxyl thymine, 5-ethyl-2'-deoxyuridine, 5-iodo-5'-amino-2,5'-dideoxyuridine, idoxuridine, AZT, AIU (5-iodo-5' amino 2',5'-dideoxyuridine), dideoxycytidine and AraC. Briefly, utilizing such methods, a wide variety of tumors (both benign and malignant) may be treated. Representative examples of such tumors include solid tumors such as lung carcinomas, renal cell carcinomas, breast carcinomas, colorectal carcinomas and melanomas, as well as diffuse cancers such a leukemias and lymphomas.

Within other aspects of the present invention, methods are provided for treating a variety of diseases wherein a subset of cells may be characterized as "diseased" or altered, utilizing the above-described nucleic acid molecules or vectors. Representative examples of such diseases include hyperkeratosis (psoriasis), prostate hypertrophy, hyperthyroidism, a wide variety of endocrinopathies, autoimmune diseases (due to autoimmune reactive cells such as certain subsets of T cells), allergies (e.g., by modulating the activity of IgE expressing cells responsible for an allergic response), restenosis (e.g., by killing cells which are responsible for the ingrowth and/or clogging of a blood vessel), a wide array of viral diseases such as AIDS (HIV), hepatitis (HCV or HBV), and intracellular parasitic diseases. Within other embodiments of the invention, methods are provided for inhibiting the growth of or destroying cells which are not traditionally associated with a disease. For example, within certain embodiments it may be desirable to administer a vector (or nucleic acid molecule alone) which inhibits or destroys fat cells in order to initiate weight loss in an animal, or to destroy hair follicles (as a depilatory reagent).

Within yet other aspects, vectors which contain or express the nucleic acid molecules encoding thymidine kinase mutants and/or guanylate kinase, or fusion protein (or the nucleic acid molecules themselves) may be utilized to correct aberrant expression of a gene within a cell, or to replace a specific gene which is defective in proper expression. Representative examples of such diseases include Adenosine Deaminase Deficiency, Alzheimer's Disease (see, for example, Goat et al., *Nature* 349:704, 1991; Sherrington et al., *Nature* 375:754, 1995; Levy-Labad et al., *Science* 269: 973, 1995), Cystic Fibrosis, as well as, for example, diseases such as Hemophilia.

Within other aspects of the present invention, methods are provided for utilizing the thymidine kinase mutants or fusion proteins described above, as a negative-selection marker gene (see e.g., Czako and Marton, *Plant Physiol.* 104:1067-1071, 1994) in prokaryotic cells, eukaryotic cells, plants (Czako and Morton, Plant Physiol. 104:1067-1071, 1994), parasites (e.g., Trypanosomes) or viruses. Alternatively, such mutants may be utilized as a conditionally lethal marker for homologous recombination (Mansour et al., *Nature* 336:348-352, 1988). A representative example is set forth in more detail below as Example 6.

Within other aspects of the present invention, methods are provided for noninvasive monitoring of gene therapy using thymidine kinase mutants and fusion proteins having thymidine kinase and guanylate kinase activities. Methods have been developed for the noninvasive imaging of HSV-1 thymidine kinase gene expression using a clinical gamma camera and by single-photon emission tomography with radiolabeled thymidine kinase substrate (see, for example, Tjuvajev et al., *Cancer Res.* 55:6126-6132, 1995; Tjuvajev et al., *Cancer Res.* 56:4087-4095, 1996). The basic approach is to administer a labeled anti-viral drug that is selectively phosphorylated by HSV-1 thymidine kinase and to monitor progress of therapy using standard scanning methods for human diagnosis. Suitable radiolabeled anti-viral drugs that are substrates for HSV-1 thymidine kinase, such as IVFRU, are well-known to those of skill in the art. See, for example, Wiebe et al., *Q. J. Nucl. Med.* 41:79-89 (1997), which contains a discussion of imaging with radiolabeled nucleoside substrates for HSV-1 TK that is incorporated by reference. The mutant thymidine kinases and fusion proteins of the present invention that have enhanced thymidine kinase activity provide a means to increase the sensitivity of such noninvasive monitoring.

The following examples are offered by way of illustration, and not by way of limitation.

EXAMPLES

Example 1

Construction of TK Mutants Containing Mutations at Codons 165-175 Utilizing a 20% Random Library Example 1 describes the construction of TK mutants containing mutations at codons 165 to 175, utilizing a 20% random library. A schematic outline which depicts the strategy utilized in this example is set forth in FIG. 1.

A. Generation of TK Mutants
  1. Generation of Oligonucleotides

A 52-mer oligonucleotide with a wild-type tk sequence (SEQUENCE ID. No. 2) and a 56-mer that contained degenerate nucleotides spanning from codon 165 through 175 (SEQUENCE ID. No. 3) of the tk gene (FIG. 23 discloses nucleotides in the open reading frame of HSVTK-1 [SEQUENCE ID NO. 1]), (where N=80% wild-type nucleotides and a 20% mixture of the other three at each position) were synthesized by Operon Technologies (San Pablo, Calif.). Both oligomers were complementary to each other along 12 bases at their 3'-ends.

```
                                       (SEQUENCE ID No. 2)
5'-TG GGA GCT CAC ATG CCC CGC CCC CGG CCC TCA CCC
TCA TCT TCG ATC GCC AT-3'

(SEQUENCE ID No. 3)
5'-ATG AGG TAC CGN NNN NNN NNN NNN NNN NNN NNN NNN
NNN NNN NNA TGG CGA TCG AA-3'
```

For the construction of pKTPD described below, two additional oligonucleotides were synthesized by Operon Technologies using phosphoramide chemistry. These oligonucleotides were:

```
5'-CCC CTC GAG CGC GGT AC-3'    (SEQUENCE ID No. 4)

5'-CGC GCT CGA GGG GAG CT-3'    (SEQUENCE ID No. 5)
```

2. Generation of Random Sequence-Containing Libraries
  a. Construction of Vectors pMDC and pMCC Chimeric vectors pMDC (which produces an inactive TK gene product) and pMCC (which produces wild-type TK) were produced from plasmids pBETK1 and pBETK2 essentially as described below. Briefly, plasmids pHETK1 and pHETK2 (Waldman et al., *J. Biol. Chem.* 258:11571-11575, 1983) are expression vectors that contain a HSV-1 tk structural gene, and are derivatives of pBR322. Restriction maps of pHETK1 and pHETK2 can be found in Waldman et al, *J. Biol. Chem.* 258:11571-11575, 1983, which describes the construction of these plasmids. Plasmid pHETK2 contains λP$_L$ and λP$_R$ promoters, ampR, and the c1857 temperature-sensitive repressor, whereas pHETK1 contains all the above except the λP$_L$ promoter. Plasmids pHETK1 and pHETK2 were obtained from Dr. William Summers (School of Medicine, Yale University, New Haven).

In order to construct pMDC and pMCC, a dummy vector, designated pKTPD was first constructed as described by Dube et al. in *Biochem.* 30:11760-11767, 1991. Briefly, oligonucleotides SEQUENCE ID Nos. 4 and 5 (20 pmol of each) were first phosphorylated and then annealed to form a double-stranded oligonucleotide with KpnI- and SstI-compatible ends and with an internal XhoI site. In addition, pHETK2 was digested with SstI and KpnI restriction endonucleases, and the large fragment isolated by agarose gel electrophoresis and subsequent electroelution. Two picomoles of the large fragment was ligated with 6 pmol of the double-stranded oligonucleotide. The resultant double-stranded circular DNA product (designated "pKTPD") was used to transform competent *E. coli* KY895 cells. *E. coli* KY895 is a TK-deficient strain (K12 tdk⁻, F⁻, ilv 276) obtained from William Summers, Yale University, New Haven, Conn. Clones containing the recombinant plasmid pKTPD grow on LB plates containing 50 μg/mL carbenicillin. The presence of recombinant plasmid DNA was verified by the cleavage at the XhoI site. The inability of pKTPD to support the growth of *E. coli* KY895 in the thymidine kinase selection medium indicates that it does not produce a functional thymidine kinase.

pHETK1 and pKTPD were then utilized to construct a new chimeric dummy vector, designated pMDC. Briefly, upon digestion with SphI and PvuII pHETK1 is cut into two fragments. The larger fragment contains ampR, c1857, λP$_R$ sequences, and part of the tk gene spanning from the BamHI to the SphI site. The smaller fragment contains the remainder of the tk gene from SphI to PvuII. Similarly, pKTPD upon digestion with the same two enzymes is cut into one larger and one smaller fragment. The smaller SphI/PvuII fragment of pKTPD contains a dummy or inactive sequence within the KpnI and SacI sites of the tk gene. Ligation of the larger fragment from pHETK1 with the smaller fragment of pKTPD results in a chimeric vector, pMDC, that produces an inactive tk gene product.

Another chimeric vector, pMCC, containing the wild-type tk gene was similarly constructed by ligating the larger fragment from pHETK1 with the smaller fragment of pHETK2. As noted above, PMCC produces active wild-type TK.

b. Generation of a Library

A library containing 20% random nucleotide sequences was constructed as follows. Briefly, a 52-mer oligo containing wild-type sequences (SEQUENCE ID No. 2) was hybridized to a 56-mer oligo which contained degenerate sequences spanning codons 165 through 175 (Sequence ID No 3).

The hybrid was extended with the Klenow fragment of *E. coli* DNA polymerase I to produce a complete double-stranded DNA product. This strategy was implemented in order to avoid synthesizing a long random nucleotide containing SEQUENCE ID No. 3, since the locations of KpnI and SacI sites (insertion sites) in the vector require a long cassette. The Klenow fragment generated double-stranded DNA was then subjected to polymerase chain reaction amplification by using two synthetic primers: the first primer, a: 5'-TGG GAG CTC ACA. TGC CCC GCC-3' (SEQUENCE ID No. 6) corresponds to the 21-base sequence of 5' terminus of oligo SEQUENCE ID No. 2. The second primer, b: 5'-ATG AGG TAC CG-3' (SEQUENCE ID No. 7) corresponds to the 11-base sequence of 5' terminus of oligo SEQUENCE ID No. 3. The polymerase chain reaction amplification reactions contained 20 mM Tris-HCl (pH 8.3), 25 mM KCl, 1.5 mM MgCl$_2$, and 0.05% Tween 20, 0.1 mg/ml BSA, 50 µM each of the four deoxynucleoside triphosphates, 20 pmol of primer "a," 40 pmol of primer "b," approximately 1 pmol of the extended double-stranded oligonucleotide as template, and 2 units of Taq polymerase (Cetus) in 100-µl final reaction volumes. Each mixture was overlaid with mineral oil and subjected to 30 rounds of temperature cycling: 94° C. for 1 minute, 34° C. for 2 minutes, and 72° C. for 7 minutes.

Low molecular weight components and excess primers were removed from the polymerase chain reaction-amplified product by centrifugation with a Centricon 30 ultrafiltration unit, and the amplified DNA was digested with KpnI and SacI. The digested double-stranded oligonucleotide containing the random sequence was again purified by a Centricon 30 unit, and ligated to the KpnI/SacI digested large fragment of pMDC at 10:1 molar ratio in the presence of 1 mM ATP and 1 unit of T4 DNA ligase (BRL) in a volume of 10 µl. Incubation was for 18 hours at 14° C. and the reaction was terminated by phenol-CHCl$_3$ extraction followed by ethanol precipitation.

C. Selection of TK Mutants

The precipitate described above was dried and dissolved in 10 µl of water, and used to transform competent *E. coli* KY895 by electroporation. One µl of ligated product was mixed with 50 µl of competent cells and electroporated at 2 KV, 25 µF, and 400 Ohms with a Gene-pulser electroporator (Bio-Rad). After the pulse, 1 ml of SOC medium (2% Bactotryptone, 0.5% Bacto yeast extract, 10 mM NaCl, 2.5 mM KCl, 10 mM MgCl$_2$, 10 mM MgSO$_4$ and 20 mM glucose) was added, followed by incubation at 37° C. for 1.5 hours with continuous agitation. An aliquot of each transformation solution was spread onto LB-agar medium containing 50 µg/ml of carbenicillin to determine total number of transformants. Selection for active TK clones was performed on TK selection medium that contained 50 µg/ml of carbenicillin. 10 µg/ml of 5' fluorodeoxyuridine, 2 µg/ml of thymidine, 20 µg/ml of uridine. 2% BBL peptone, 0.5% NaCl, 0.2% glucose, and 0.8% Gel-Rite (Scott Laboratories, Inc., Carson, Calif.) (FIG. 1). Colonies on carbenicillin medium were incubated at 37° C. for 14-16 hours, whereas inoculated TK selection medium was incubated at 37° C. for 24 hours.

From a total of 53,000 transformants that grew on carbenicillin medium, 190 were able to complement *E. coli* KY 895 for TK function.

Example 2

Construction of TK Mutants Containing Mutations at Codons 165-175 Utilizing a 100% Random Library Example 2 describes the construction of TK mutants containing mutations at codons 165-175 utilizing a 100% random library. The strategy which was utilized for this example is similar to that described in Example 1 above.

A. Generation of TK Mutants

1. Generation of Oligonucleotides

A 52-mer 5'-d(TG GGA GCT CAC ATG CCC CGC CCC CGG CCC TCA CCC TCA TCT TCG ATC GCC AT)-3' (SEQUENCE ID No. 8) with a wild-type tk sequence and Kpn I site at the 5' end was synthesized by Operon Technologies (San Pablo, Calif.). In addition, a 56-mer containing random nucleotides corresponding to HSV-1 tk codons 165-175 and containing a Sac I site at the 3' end 5'-d(ATG AGG TAC CGN NNN NNN NNN NNN NNN NNN NNN NNN NNN NNN NNA TGG CGA TCG AA)-3' (SEQUENCE ID No. 3), where N=equimolar concentrations of G, A, T, or C, was also synthesized. The oligonucleotides were separated by electrophoresis through a 20% denaturing polyacrylamide gel, followed by purification on a reverse-phase mini column (Glen Research, Sterling, Va.).

2. Generation of a 100% Random Sequence—Containing Library

The 52-mer corresponding to the wild-type HSV-1 tk sequence was hybridized with the 56-mer containing random nucleotides. The hybrid was then extended with the Klenow fragment of DNA polymerase I, PCR amplified, and ligated into pMDC essentially as described above in Example 1.

3. Selection of TK$^+$ Mutants

Functional TK mutants were identified by colony formation on TK-selection medium based on their ability to phosphorylate dT essentially as described below. Briefly, the ligated product was introduced into tk$^-$ *E. coli* strain KY895. The total number of transformants was determined by plating on LB agar containing 50 µg of carbenicillin per mL and the number of transformants that produced catalytically active thymidine kinase was determined by plating on TK-selection medium [2% BBL peptone, 0.5% NaCl, 0.2% glucose, 0.8% Gel-Rite (Scott Laboratories, Carson, Calif.)], 50 µg 1 mL of carbenicillin, 10 µg/mL of fluorodeoxyuridine, 2 µg/mL of dT, and 20 µg/mL of uridine.

Two million (2×10$^6$) transformants were screened from the 100% random library, of which 1540 formed colonies on the TK-selection medium.

B. Selection of AZT-Sensitive Mutants

A subset of 690 mutants from the 100% random library (TKI) and 190 mutants from the 20% degenerate library (TKF) (described above in Example 1) were subjected to secondary negative selection on medium containing AZT in order to identify mutants that exhibited enhanced phosphorylation of AZT. This screen is based upon the premise that mutants with increased ability to phosphorylate AZT relative to dT would be unable to form colonies on the AZT-selection medium. In particular, the product, AZT monophosphate would be further phosphorylated by the host cell's nonspecific nucleotide kinases, or possibly by the mutant TK, incorporated into bacterial DNA by host DNA polymerases, terminate DNA synthesis, and thus prevent replication of the host chromosome.

Briefly, the TK mutants were first grown as individual colonies on TK-selection medium (1.0 µg/mL of dT), and then replica plated onto AZT-selection medium (0.05 µg/mL of AZT, 1.0 µg/mL of dT). All other components in the AZT-selection medium were the same as the TK-selection medium. Those TK mutants which failed to grow on the AZT-selection medium were selected and retested for growth on both TK- and AZT-selection media separately.

Of the 880 primary selectants that were screened, only two mutants, TKF 105 (from the 20% library) and TKI 208 (from the 100% library), formed colonies on the TK-selection medium at an efficiency similar to that of *E. coli* harboring the wild-type plasmid but not on the AZT-selection medium (FIG. 2).

The nucleotide and deduced amino acid sequences of TKF 105 and TKI 208 are presented in FIG. 3. Both mutants contain a single amino acid substitution at the same position: Leu-170 was changed to Ile in TKF 105 and to Val in TKI 208. No other substitutions were observed in the surrounding 220 nucleotides.

To ensure that the difference between TKF 105 and TKI 208 was not due to differential expression of TK in *E. coli* harboring mutant and wild-type plasmids, Western blots of extracts from cells containing either TKI 208 or wild-type plasmids were compared. No significant difference was observed in the amount or electrophoretic mobility of immunoreactive staining protein. Also, the rate of dT phosphorylation per mg of protein was determined, and found to be similar in extracts of E. coli harboring TKI 208, TKF 105, and wild-type plasmids.

In order to show that the lack of growth of these two mutants on AZT-selection medium was due to enhanced phosphorylation of AZT, the following experiments were conducted.

1. Rate of [$^3$]AZT Uptake

First, the rate of [$^3$H]AZT uptake relative to [$^3$H]dT into E. coli harboring wild-type and mutant plasmids was determined. These studies indicated that E. coli harboring the AZT-sensitive mutants, TKF 105 and TKI 208, exhibited a 4-fold increase in the ratio of AZT to dT uptake, as compared to E. coli with the wild-type plasmid.

2. Affinity Purification of TK

Purification of wild-type and mutant TKs was performed by affinity chromatography on CH-Sepharose 4B (Pharmacia) coupled to p-aminophenylthymidine 3'-phosphate. Briefly, crude bacterial extract was passed three times through a 7-mL bed-volume affinity column. The column was then washed sequentially using 30 mL each of buffer A [0.1 M Tris HCl, pH 7.5/5 mM dithiothreitol (DTT)/10% glycerol], buffer B (0.1M Tris-HCl, pH 7.5/0.5 M KCl/5 mM DTT/10% glycerol), and buffer A. TK was eluted using a 60-mL linear gradient of 0-600 μM dT in buffer C (0.3 M Tris HCl, pH 7.4/50 mM KCl/10% glycerol). Active fractions were pooled and dialyzed against three changes each of 2 liters of 50 mM Tris-HCl, pH 7.4/5 mM DTT/10% glycerol. Except in the final dialysis, all the above buffers contained 50 μg/mL of aprotinin and 2 μg/mL each of pepstatin and leupeptin.

3. Kinetics of AZT Phosphorylation

Secondly, the kinetics of AZT phosphorylation by the two mutants was determined. Briefly, reactions were carried out in a final volume of 100 μl containing 50 mM Tris-HCl (pH 7.5), 5 mM ATP. 4 mM MgCl$_2$, 2.5 mM DTT, 12 mM KCl, 0.18 mg/mL of bovine serum albumin, 5% glycerol, 0.08 μCi of [$^3$H]AZT (Sigma), various concentrations of unlabeled AZT (0-4.0 μM), and purified enzymes (4 and 1.2 units, respectively, for wild-type and TKI 208). (One unit of enzyme is defined as that amount that can phosphorylate 1.0 pmol of dT to TMP in 1 minute under the conditions described above.) Incubation was at 34C±1° C. for 10 minutes, and reactions were stopped by adding 1.0 mM unlabeled dT and cooling on ice. Half of the reaction mixtures were pipetted onto a DEAE-cellulose disc (25 mm), dipped in distilled water (1 minute), followed by four washes in absolute ethanol. The amount of radioactivity adsorbed to the disc was determined by scintillation spectroscopy. K$_m$ and V$_{max}$ values were determined by using the Cleland SUBIN program (Cleland, *Methods Enz.* 63:103-138, 1979). The values for k$_{cat}$ were calculated using the equation V$_{max}$=k$_{cat}$[E]$_o$, where [E]$_o$=total enzyme concentration. TK assays wherein phosphorylation of dT was measured were carried out in a final volume of 50 μl using 0.3 μCi ([3H-methyl]dT: 87 Ci/mmol: Amersham), various concentrations of unlabeled dT (0-4.0 μM), and 1.1 and 0.5 units of TK for the wild-type and TKI 208, respectively. All other components in the reaction mixtures and the incubation conditions were as described above for phosphorylation of AZT.

As shown below in Table I, the AZT-sensitive variant TKI 208 exhibits a lower K$_m$ (4.4 μM) compared to that of the wild-type (8.5 μM). By comparing the k$_{cat}$/K$_m$ between the two substrates (AZT vs. dT), it can be seen that TKI 208 selectively phosphorylates AZT 2.3-fold more efficiently than dT. Similar preliminary experiments with purified TKF 105 TK also showed lower K$_m$ (3.7 μM) for AZT, but similar values for k$_{cat}$/K$_m$ compared to the wild-type.

TABLE I

ABILITY OF WILD-TYPE AND TKI 208 TKS TO PHOSPHORYLATE AZT AND DT

| Phosphorylation | | K$_m$, μM | k$_{cat}$, s$^{-1}$ | k$_{cat}$/K$_m$ s$^{-1}$, M$^{-1}$ | k$_{cat}$/K$_m$(AZT) k$_{cat}$/K$_m$(dT) |
|---|---|---|---|---|---|
| AZT | Wildtype | 8.46 ± 1.3 | 3.6 × 10$^{-2}$ | 4.2 × .10$^3$ | 1.7 × .10$^{-3}$ |
| | TKI 208 | 4.40 ± 0.43* | 3.0 × 10$^{-2}$ | 6.5 × 10$^3$ | 4.0 × 10$^{-3}$ |
| dT | Wildtype | 0.475 ± 0.10 | 1.21 | 2.5 × 10$^6$ | |
| | TKI 208 | 0.35 ± 0.008 | 0.56 | 1.57 × 10$^6$ | |

C. Thermostability Analysis of Mutant TKs

Mutants were analyzed for thermostability essentially as described below. Briefly, 25 μg of each extract were preincubated in 0.3 mL of 28 mM Tris-HCl, pH 7.5 containing 0.28 mg/mL of bovine serum albumin, 28 μg/mL of aprotinin, 2 μg/mL (each) of pepstatin and leupeptin, at 42° C. for 0.5, 10, 20, 30, or 40 minutes. At each time point 30-μl (2.5 μg) aliquots were assayed for residual TK activity in a total reaction volume of 50 μl containing 50 mM Tris-HCl (pH 7.5), 5 mM ATP, 4 mM MgCl$_2$, 2.5 mM DTT, 12 mM KCl, 0.18 mg/mL of bovine serum albumin, 5% glycerol, and 1 μM [$^3$H-methyl]dT (60×10$^3$ dpm/pmol). Incubation was at 34° C. for 10 minutes. The reaction was stopped by cooling on ice, and 25 μl was pipetted onto a DEAE-cellulose disc. Wash and assay conditions for the discs were performed as described for the AZT assay above.

Assay results of unfractionated extracts of TKF 2, TKF 56, TKF 75, TKF 446 and wild-type TK are shown in FIGS. 4A-4D. One of the mutants, TKF 2, was more thermostable at 42° C. than any of the other mutants, or than the wild-type. Except for TKF 2, all of the mutants tested, including the wild-type, had ratios of residual activity after preincubation at 42° C. compared to 34° C. of 0.05-0.30: TKF 2 had a ratio of 0.7. TKF 2 contains three amino acid substitutions: Pro-165→H is, Ala-167→Ser, and Ala-174→Val (FIG. 3). TKF 75 contained an Ala-167→Ser substitution, TKF 56 a Ala-174→Val, and TM 440 a Pro-165→Ala substitution. The thermolability of mutants TKF 56 and TKF 75 with Ala-174→Val and Ala-167→Ser substitutions, respectively, was similar to that of the wild-type. Both lost >80% of their activity after incubation for 5 minutes at 42° C. TKF 440 with a Pro-165→Ala is more stable, but not as stable as TKF 2, the triple mutant.

Figure 4:
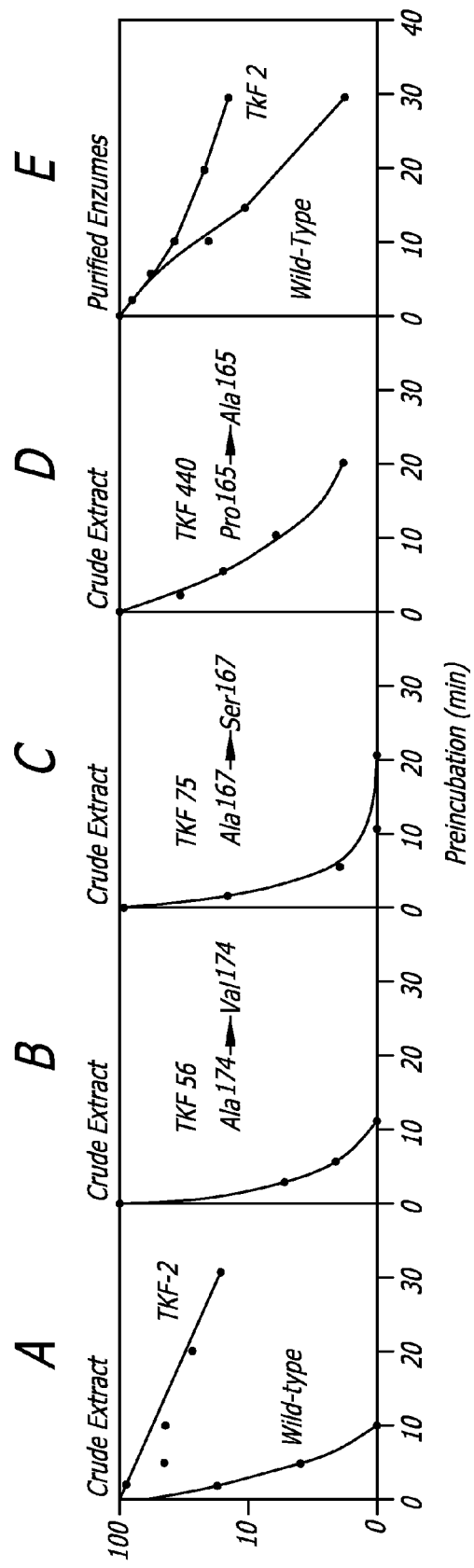
FIG. 4 is a series of graphs which depict the thermostability of wildtype TK and TK mutants.

Two types of experiments were carried out to verify the thermostability of TKF 2. First, TK protein from TKF 2 and the wild-type plasmid harboring E. coli were purified to near homogeneity by affinity chromatography, and assayed as described above. As before, loss of activity is less in TKF 2 than in the wild-type after preincubation at 42° C. (FIG. 4E).

Figure 5:
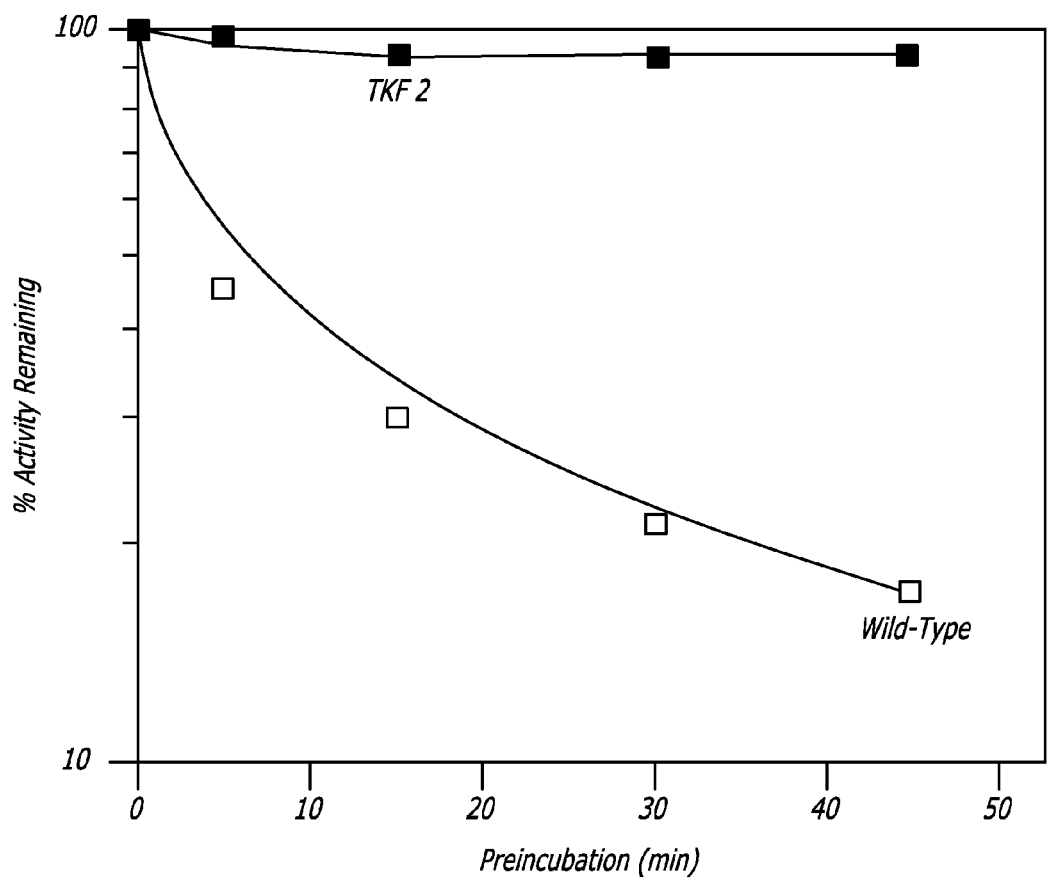
FIG. 5 is a graph which depicts heat-inactivation profiles for in vitro translated wild-type and TKF2 thymidine kinase.

Secondly, tk genes from TKF 2 and wild-type TK were transferred into a vector with a promoter for T3 RNA polymerase. More specifically, the full-length Bgl II-Pvu I fragments of tk genes from wild-type and TKF 2 plasmids were isolated and subcloned into the pBluescript SK$^+$ (Stratagene) vector between the Spe I and EcoRI sites with the use of synthetic linkers. In vitro transcription using the T3 promoter was carried out using the Promega transcription system. In vitro translation was carried out using a reticulocyte lysate system (Promega) following the supplier's protocol. The loss of TK activity of the in vitro synthesized proteins from the wild-type and TKF 2 tk genes as a function of preincubation at 42° C. is shown in FIG. 5. The protein encoded by TKF 2 lost <10% of its activity after preincubation for 45 minutes. In contrast, the protein encoded by the wild-type gene lost >80% of its initial activity. The degree of thermostability exhibited by the in vitro synthesized TKF 2 was similar to or greater than that of crude extracts harboring the original TKF 2 plasmid. For SDS/PAGE analysis, the translated products were labeled with [$^{35}$S]methionine.

Figure 6:
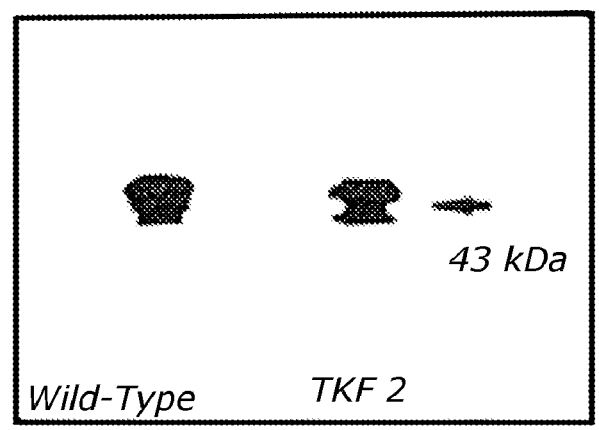
FIG. 6 is an autoradiograph of SDS/PAGE-fractionated in vitro translated products (wild-type and TKF2).

An autoradiograph of the labeled proteins after SDS/PAGE is shown in FIG. 6. The arrow indicates the expected size of translated TKs as judged by molecular mass standards (Bio-Rad). From this autoradiograph it is evident that the translation products migrate as double bands, one of which corresponds to a protein of 43 kDa, which is in accord with the reported size of HSV-1 TK expressed in E. coli. The second band could be due to the proteolytic degradation of a 32-residue fragment at the amino-terminal end, which does not detectably alter TK activity of the HSV-1 TK.

Example 3

Construction and Analysis of TK Mutants with Mutations at Codons 155, and 161 to 165 Utilizing a 20% Random Library This example describes the construction and analysis of TK mutants which are mutagenized at codons 155, and 161 through 165. Bacterial strains and materials which were utilized within this example are set forth below.

Bacterial Strains. E. coli strain KY895 (F$^-$, tdk$^-$, 1-ilv), originally described by Igarashi et al. (*Genetics* 57:643-654, 1967), was used in the genetic complementation assays for thymidine kinase activity. E. coli strain NM522 (F' lacI$^q$ Δ (lacZ)M15 proAB/supE thi Δ (lac proAB)Δ(hsdMS-mcrB)5 ($r_k^-$McrB$^-$))(NEB, Beverly, Mass.) was used as a recipient in all subcloning experiments. Helper phage VCM13 (Stratagene, La Jolla, Calif.) was used in the production of single-stranded phage for sequencing.

Materials. L-[S]Methionine/cysteine (specific activity, 1140 Ci/mmol) for protein synthesis determination and [methyl-$^3$H] thymidine (specific activity, 87 Ci/mmol) were purchased from Amersham. Other radioisotopes [[side chain-2-$^3$H] acyclovir (specific activity, 28.6 Ci/mmol) and [5-$^3$H]-deoxycytidine (specific activity, 29 Ci/mmol)] were purchased from Du Pont-New England Nuclear (Boston, Mass.), and [8$^{-3}$H] ganciclovir (specific activity, 22 Ci/mmol) and [methy$^{-3}$H]-3'-azido-3' deoxythymidine (specific activity, 14 Ci/mmol) were from Moravek (Brea, Calif.). Restriction endonucleases and T4 DNA ligase were purchased from New England Biolabs (NEB). Promega (Madison, Wis.) was the source of the in vitro transcription and translation reagents except for the cap analog, $^7$ m(5')Gppp (5')G, which was purchased from NEB. Oligonucleotides used for sequencing and polymerase chain reaction amplifications were obtained from Operon (Alameda, Calif.). Other chemicals were purchased from Sigma (St. Louis, Mo.) except where designated.

A. Generation of TK Mutants

1. Generation of Oligonucleotides

Two oligonucleotides were synthesized by American Synthesis, Inc. (Pleasanton, Calif.): MB 110 (70mer) 5'-TGG-GAGCTCA CATGCCCCGC CC[CCG]GCCCT CACCCT-CATC [TTCGACCGCC ATCCC]ATCGC CGCCCTCCTG-3' (SEQUENCE ID No. 9), and MB111 (38mer) 5'-ATGAGGTACC GCGCAGCTGG GTAGCACAGG AGGGCGGC-3' (SEQUENCE ID No. 10). Within these oligonucleotides, nucleotides in brackets where synthesized as 80% wild-type nucleotide, and 20% the other three nucleotides.

At the 5' end of MB 110 is a SacI restriction site and, at the 5' end of MB111, a KpnI site. These restriction sites were utilized at a later step after second-strand synthesis occurred. Furthermore, as an internal control, a PvuII site was introduced (silent change) in MB111 in order to allow confirmation of random sequence insertion prior to sequencing. Twelve nucleotides at the 3' ends of each oligonucleotide are complementary to allow for hybridization of the two strands to each other. Each oligonucleotide was subjected to electrophoresis on a 20% acrylamide-urea gel and visualized by UV shadowing on a PEI-cellulose TLC plate (Baker, Phillipsburg, N.J.), the portion of the gel containing the correct sized oligonucleotide was excised, and the oligonucleotide was eluted from the gel in 0.5M NH4Ac/10 mM MgOAc$_2$ overnight at 37° C. The eluted oligonucleotide was then ethanol-precipitated and resuspended in H2O. An OD$_{260}$ measurement was taken, and the extinction coefficient for each oligo was used to determine the concentration.

Equimolar amounts of MB110 and MB111 (25 pmol) were annealed in a small volume (20 µl) in 1× annealing buffer (10× annealing buffer=70 mM Tris (pH 7.5)/60 mM MgCl$_2$/200 mM NaCl) for 5 minutes at 95° C., then moved to 65° C. for 20 minutes, followed by slow cooling to room temperature. To the annealed oligonucleotides (20 µl) were added 2 µl of 10× annealing buffer, 2.8 µl of 10 mM dNTPs, 0.8 µl of 0.1M of dithiothreitol (DTT), 2.4 µl of DNA polymerase I Klenow fragment (5 units/µl), and H$_2$O to bring the volume to 40 µL. The mixture was placed at 37° C. for 30 minutes, at 65° C. for 10 minutes, and finally at room temperature for 10 minutes. Verification of fully extended radioactive oligonucleotides was accomplished by subjecting the samples to denaturing acrylamide gel electrophoresis and autoradiography. Amplification of the extended products was performed using the polymerase chain reaction with Taq polymerase (Stratagene). The 100 uL reactions contained 20 mM Tris (pH 8.3)/25 mM KCl/1.5 mM MgCl$_2$/0.05% Tween 20)/0.1 mg/mL BSA/50 µM of each of the four deoxynucleoside triphosphates (dNTPs)/22 pmol PCR primer 1/20 pmol PCR primer 2/2 units of Taq polymerase and 6 pmol of the extended random oligonucleotide; Primer 1=5' TGG-GAGCTCACATGCCCCGCC-3' (SEQUENCE ID No. 6) and primer 2=5'-ATGAGGTACCG-3' (SEQUENCE ID No. 7). One drop of mineral oil was added to each tube, which was then placed in a Perkins Elmer-Cetus thermal cycler (Norwalk, Conn.) and programmed for 30 cycles of 95° C. for 1 minute and 34° C. for 2 minutes. At the end of the 30 cycles, the reactions were left at 72° C. for 7 minutes, and then the cycler was maintained at 4° C. After confirmation of amplification by 2% agarose gel electrophoresis, the product-containing reactions were pooled, precipitated and digested with KpnI and SacI. Doubly restricted fragments were distinguished from single cut or uncut fragments on non-denaturing acrylamide gels, and the appropriate fragment was excised and isolated as described above.

2. Generation of Random Sequence—Containing Libraries

Cesium chloride gradient purified pMDC ("dummy" vector) which was constructed as described above in Example 1, digested with KpnI and SacI restriction endonucleases, and gel-isolated from a 1% agarose/1×TBE gel using GenClean II (Bio101, La Jolla, Calif.). This vector was ligated with the gel-isolated PCR-amplified random fragment overnight at 16° C. with 1 unit of T4 DNA ligase.

3. Selection of TK Mutants

The ligated mixture was then used to transform KY895 by electroporation (BioRad gene pulser, 2 kV, 25 µF, 400Ω). Briefly, cells were prepared for electroporation according to a protocol provided by BioRad (Richmond, Calif.). After each pulse, 1 mL of SOC (2% Bactotryptone/0.5% yeast extract/10 mM NaCl/2.5 mM KCl/10 mM MgCl$_2$/10 mM MgSO$_4$/20 mM glucose) was added to the curette and the electroporation mixture transferred to a 25 mL snap-cap Falcon tube. After the tubes were shaken for 1 hour at 37° C., the cells were plated onto LB plates [per liter: 10 g tryptone/5 g of yeast extract/10 g NaCl (pH 7)] containing carbenicillin (50 µg/mL), ("LB+ carb$^{50}$ plates") and incubated at 37° C. overnight. The number of colonies was counted, picked with a toothpick, and streaked on TK selection media [2% BBL Trypticase peptone (Becton Dickenson, Cockeysville, Md.)/0.5% NaCl/0.8% Gel-Rite (Scott Laboratories, Carson, Calif.)/0.2% glucose/50 µg/mL carbenicillin/10 µg/mL 5'-fluorodeoxyuridine/2 µg/mL thymidine/12.5 µg/mL uridine]. The basis of this selection is that 5'-fluorodeoxyuridine (FUdR) is phosphorylated by thymidine kinase to form FdUMP, an inhibitor of the de novo pathway enzyme, thymidylate synthase. The requirement for dTMP can then be fulfilled only by an active thymidine kinase. Uridine is supplied to inhibit thymidine phosphorylase. After 16-24 hours, the TK selection plates were scored for growth, and any positives picked and restreaked on TK selection plates and LB+ carb$^{50}$ plates to confirm the phenotype.

Approximately 260 random transformants were screened for their ability to complement KY895, a TK-deficient E. coli on TK selection media. Of these, 82 were scored as positives and sequenced. Therefore, approximately 32% of all transformants encoded functional enzymes.

B. Analysis of Mutants

TK mutants were isolated and sequenced as follows. Briefly, mutant DNA was isolated from overnight cultures grown in 2×YT (per liter: 16 g tryptone/10 g of yeast extract/5 g NaCl)+carb$^{50}$ using the Promega Magic miniprep kit according to the manufacturer's instructions, except that 3 mLs of culture was used per isolation because of the low copy number of the plasmid. Ten microliters of each dsDNA was alkaline-denatured, precipitated, and resuspended in Sequenase reaction buffer, H$_2$O, and sequencing primer (5'-CAT-GCCTTATGCCGTGA-3') (SEQUENCE ID No. 11). The primer was then annealed, and the DNA subjected to dideoxy sequencing (Sanger et al., 1977) using Sequenase according to the manufacturers instructions (USB, Cleveland, Ohio).

Eleven of the clones encoded wild-type amino acid sequence (13.4%), with seven of these containing the wild-type nucleotide sequence. Three clones with wild-type amino acid residues contained single nucleotide changes (all different), and one contained three nucleotide changes. As shown in Table IA below, a total of 49 TK positive clones containing single amino acid changes (59.8%) were identified. Nineteen double amino acid mutations (23.2%), two triple (2.4%) and one clone containing four amino acid changes (1.2%) were identified. Within Table IA, wild-type HSV-1 TK amino acids mutated are given in the boldface box with the residue number and the type of residue found in the majority of sequences [O=hydrophobic; I=hydrophilic; (+)=positively charged; (−)=negatively charged residues]. Below the wild-type residue are the number of times a particular amino acid substitution was found. In the bottom section, the percentages of each type of residue found are listed.

The amino acid sequences of clones with multiple alterations are shown in Table 1B. The wild-type amino acids and their positions in the HSV-1 TK polypeptide are indicated at the top of the table. Double, triple, and quadruple amino acid substitutions are shown in the respective categories. If a set of mutations was identified more than once, the number of occurrences is noted on the left in parentheses.

TABLE IA

| Wild-type Sequence | O<br>P<br>155 | O<br>F<br>161 | (−)I<br>D<br>162 | (+)I<br>R<br>163 | (+)I<br>H<br>164 | O<br>P<br>165 |
|---|---|---|---|---|---|---|
| Substitutions at Each Position | 3L<br>2A<br>2T<br>1Q<br>1R | 4I<br>4Y<br>3C<br>2L<br>1S | 5E<br>1G | 5C<br>1S | 3N<br>1T | 3L<br>2T<br>2S<br>1N<br>1A |
| Types of Substitutions | 11%(+)<br>33% I<br>56% O | 57% I<br>43% 0 | 83% (−)I<br>17% I | 100% I | 100% I | 10% (+)<br>50% I<br>40% O |

TABLE IB

| Number of changes | P 155 | F 161 | D 162 | R 163 | H 164 | P 165 |
|---|---|---|---|---|---|---|
| Doubles | A | V | | | | |
| | Q | I | | | | |
| | Q | | E | | | |
| | R | | E | | | |
| (4) | R | | G | | | |
| | T | | E | | | |
| (2) | | I | | H | | |
| | | I | | | | |
| | | N | | | | |
| | | | Y | C | | |
| | | | N | | K | |
| (2) | | | E | | N | |
| | | | | P | Q | |
| | | | | | Q | L |
| Triples | Q | | E | | | L |
| | A | | | | | T |
| Quadruple | | N | S | | N | A |

C. Secondary Screening and Subcloning

The ability of pMCC (KY895) and 35 log-phase mutant pMDC (KY895) cultures to produce colonies on acyclovir ("ACV") or AZT plates was determined in a secondary screen as described below. Briefly, log-phase cultures of TK positive clones were serially diluted in 0.9% NaCl and spread onto acyclovir or AZT plates (TK selection plates except 1 µg/mL thymidine+1 µg/mL acyclovir or 0.05 µg/mL AZT). Mutant cultures were also spread onto duplicate TK selection and LB+ carb50 plates. One set of TK selection plates and LB+ carb50 plates were incubated at 42° C. All other plates were incubated at 37° C. After 16-24 hours the plates were scored.

Results are shown in Table II below. Briefly, only mutants that gave results which differed from those observed with the wild-type pMCC (KY895) are shown. Mutants are designated with the wild-type residue and position number followed by the amino acid substitution deduced from the nucleotide sequence; e.g., F161I indicates that isoleucine replaces phenylalanine at residue 161 in this particular mutant. (++) indicates that the same number of colonies were observed as compared to control plates; (+) indicates that fewer (<20% those observed with pMCC) and generally smaller (~50% smaller diameter) colonies were observed as compared to control plates; and (−) indicates that no colonies were observed.

TABLE II

| Clones | ACV | AZT | LB | 37° C. | 42° C. |
|---|---|---|---|---|---|
| pMCC (wild-type) | ++ | ++ | ++ | ++ | ++ |
| P155A/F161V | ++ | + | ++ | ++ | ++ |
| F161I | + | + | ++ | ++ | ++ |
| F161C | + | − | ++ | ++ | ++ |
| F161L | ++ | ++ | ++ | ++ | − |
| R163P/H164Q | + | + | ++ | ++ | − |
| F161I/R163H | ++ | ++ | ++ | ++ | + |
| pMDC | − | − | ++ | − | − |

As shown in Table II, all cultures formed colonies on control TK 25 selection and LB+carb[50] plates. In comparison to the wild-type, several mutants appeared to preferentially utilize one or both nucleoside analogues over thymidine (P155A/F161V, F161I, F161C, and R163P/H164Q). In addition, several mutants were unable to form colonies on TK selection plates at 42° C. (F161L and R163P/H164Q), and one (F161I/R163H) showed a severely reduced ability to form colonies at 42° C.

D. Expression of Mutant Enzymes in a Cell-Free Translation System

1. Subcloning of Selected Mutants

In order to study the properties of the mutant TKs, the 1.07 kbp MluI-BssHII fragment of eight mutants was subcloned into the in vitro vector pT7:HSVTKII. More specifically, DNAs of selected clones were restricted with MluI and BssHII to release a 1.07 kbp fragment [nucleotide numbers ~335 through 1400 on the McKnight sequence (*Nucl. Acids Res.* 8: 5949-5964, 1980; the McKnight strain was derived from the mp strain of HSV-1, Wagner, *PNAS* 78:1441-1445, 1981)]. The fragments were gel-isolated from 1% agarose gels using GenCleanII, and ligated to pT7:HSVTKII vector DNA which had been restricted with MluI and BssHII, treated with calf intestinal alkaline phosphatase, and gel-isolated. pT7:HSVTKII was derived from pT7:HSVTK transcription vector described by Black and Hruby in *J. Biol. Chem.* 267: 9743-9748, 1992. Briefly, pT7:HSVTKII differs from pT7: HSVTK only by the loss of an NcoI-BamHI fragment 3' to the end of the HSV-1 tk gene which was originally used to aid in the initial cloning of the tk gene.

2. Sequence Analysis

In the final sequence analysis of the eight mutant fragments subcloned into the pT7:HSVTKII vector, two additional amino acid differences were identified between these tk genes. The sequence of pT7:HSVTKII is exactly the same as that published by McKnight (*Nuc. Acids Res* 8(24):5949-5963, 1980). pMCC, the parental plasmid of pMDC and hence the vector into which the random sequences were ligated, contains two amino acid aberrations from the McKnight sequence. These are at position 434 (C→T) and 575 (G→A), and result in a proline-49 to leucine and an arginine-89 to glutamine change. Therefore, all mutants contain these two mutations in addition to those described. In addition, a single nucleotide difference at position 480 (C→T) was also identified but does not result in an amino acid change.

Because all in vitro analyses were compared against pT7: HSVTKII as the wild-type, the MluI-BssHII fragment from pMCC was subcloned into the corresponding sites of pT7: HSVTKII (now designated pT7:MCC) and the subsequent cell-free translation products compared to those derived from pT7:HSVTKII. Time course and thermal stability analyses showed no significant difference between pT7:HSVTKII- and pT7:MCC-derived translation products. No significant difference in phosphorylation efficiency was observed between pT7:MCC and pT7:HSVTKII when thymidine (1.3-fold), deoxycytidine (1.3-fold), GCV (0.8-fold), ACV (0.95-fold), or AZT (1.1-fold) were used as substrate. Furthermore, Sanderson et al. (*J. Mol. Biol.* 202:917-919, 1988) reported that the $K_m$ for thymidine and ATP and the $V_{max}$ of TK purified from *E. coli* harboring pHETK2 (the parent plasmid of pMCC) and HSV-1-infected cells were indistinguishable. Therefore, the alterations observed in the properties of the mutant TKs can be attributed to the nucleotide substitutions within the target region and that any differences between the vectors (pT7:MCC and pT7:HSVTKII) exerted only minor changes in catalytic properties.

3. In vitro Transcription and Translation

The transcripts described above were then used in a rabbit reticulocyte lysate cell-free translation system to synthesize active enzymes. Cell-free translation was according to Promega using nuclease-treated rabbit reticulocyte lysates.

Figure 7:
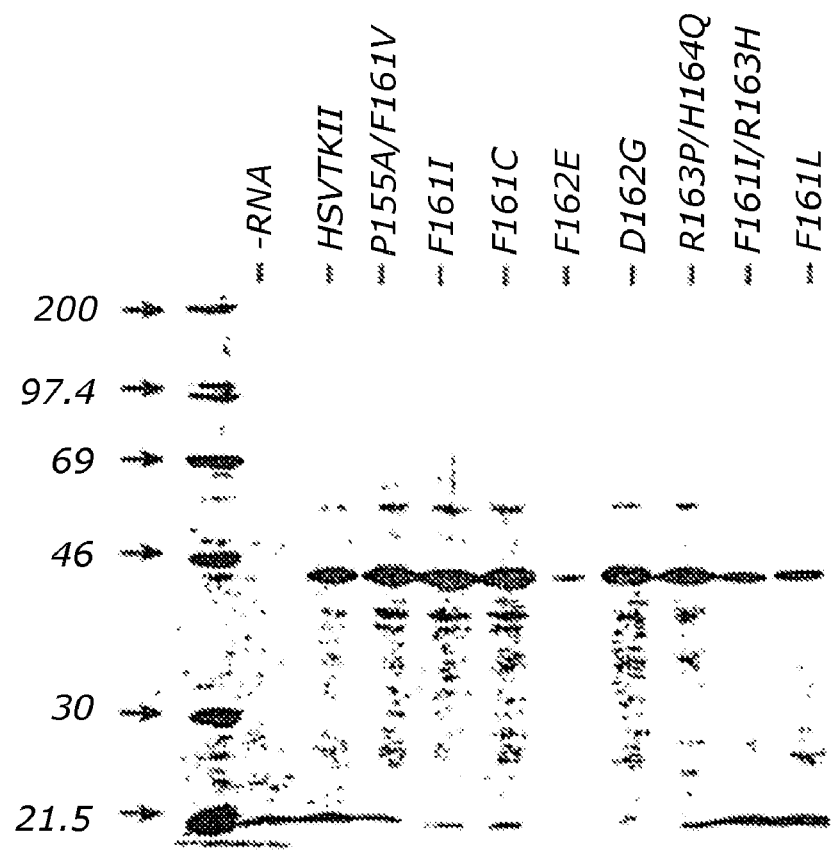
FIG. 7 is an autoradiograph of $^{35}$S-radiolabeled cell-free translation products subjected to SDS-PAGE and TCA-precipitable counts.

Expression of full-length proteins was analyzed by subjecting $^{35}$S-radiolabeled cell-free translation products to SDS-PAGE and autoradiography. Briefly, 1 µl of each radiolabeled cell-free translation in vitro-derived mutant mRNAs was subjected to SDS-containing polyacrylamide (12%) gel electrophoresis. An autoradiograph of this gel is shown in FIG. 7. The first lane contains $^{14}$C-labeled rainbow molecular weight markers (Amersham) with the apparent molecular weight ($\times 10^{-3}$) given on the left. The second lane corresponds to a cell-free translation performed in the absence of any added mRNA. The third lane corresponds to the wild-type pT7:HSVTKII mRNA translation product. All other lanes contained translation products of the mutant mRNAs produced as described above. As is evident from FIG. 7, the major radiolabeled translation product from each mutant transcript migrates during electrophoresis as a ~43 kDa protein with the same electrophoretic mobility as that observed with translation products from wild-type pT7:HSVTKII transcripts.

To quantitate the level of protein synthesis for each translation, determination of trichloroacetic acid precipitable counts from each of the same samples was performed in triplicate. The amount of acid-precipitable counts roughly parallels the band intensity of each mutant in FIG. 7.

E. Time Course Analysis of Mutant Enzymes

Figure 8A:
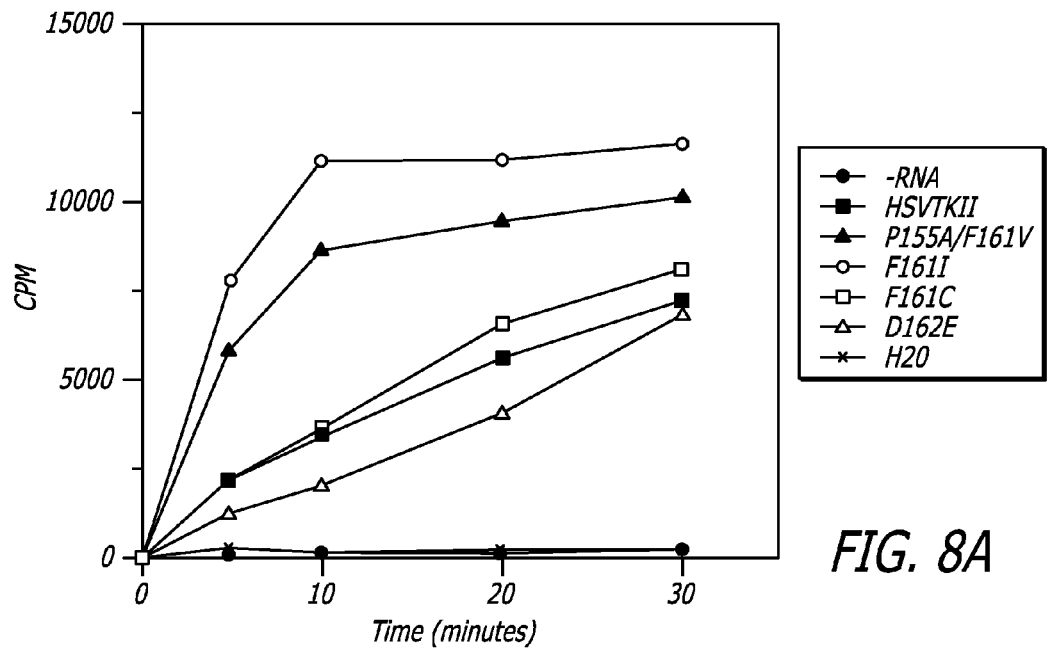
FIGS. 8A and 8B are two graphs which illustrate a time course analysis of high activity (A) and low activity (B) mutants produced in a rabbit reticulocyte lysate cell-free translation system.

On the basis of TK activities, mutant TKs were classified into two subsets: (1) high-activity mutants (P155A/F161V, F161I, F161C, and D162E); (2) low-activity mutants (F161I/R163H, F161L, D162G, and R163P/H164Q). For the high-activity mutant enzymes, unlabeled translation products were diluted 1/9 and incubated for 0, 5, 10, 20, or 30 minutes at 30° C. Results of this experiment are shown in FIG. 8A: The TK activity results (counts per minute) were adjusted to reflect equivalent protein synthesis levels using the corresponding TCA-precipitable counts ($^{35}$S cpm). Two of the mutants (F161I and P155A/F161V) demonstrated a statistically higher affinity for thymidine than the wild-type TK. Standard deviations of F161C and D162E activities (data not shown) indicate no difference in activities when compared to the wild-type TK enzyme activities.

Figure 8B:
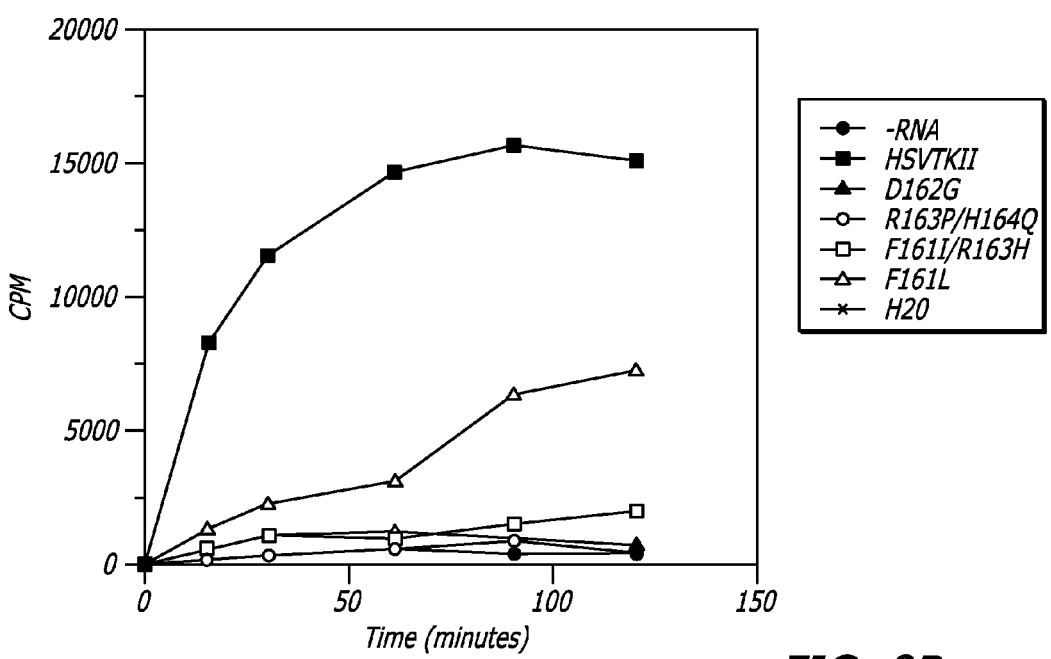

The low-activity mutants were diluted 1/5, and the rate of phosphorylation as a function of time was also determined. Results of this experiment are shown in FIG. 8B. The time course analysis indicates that most of the mutants had less than 10% wild-type activity. One, F161L, however, demonstrated a moderate ability to phosphorylate thymidine, albeit at a much reduced rate from HSVTKII.

F. Thermal Stability Assays

Figure 9A:
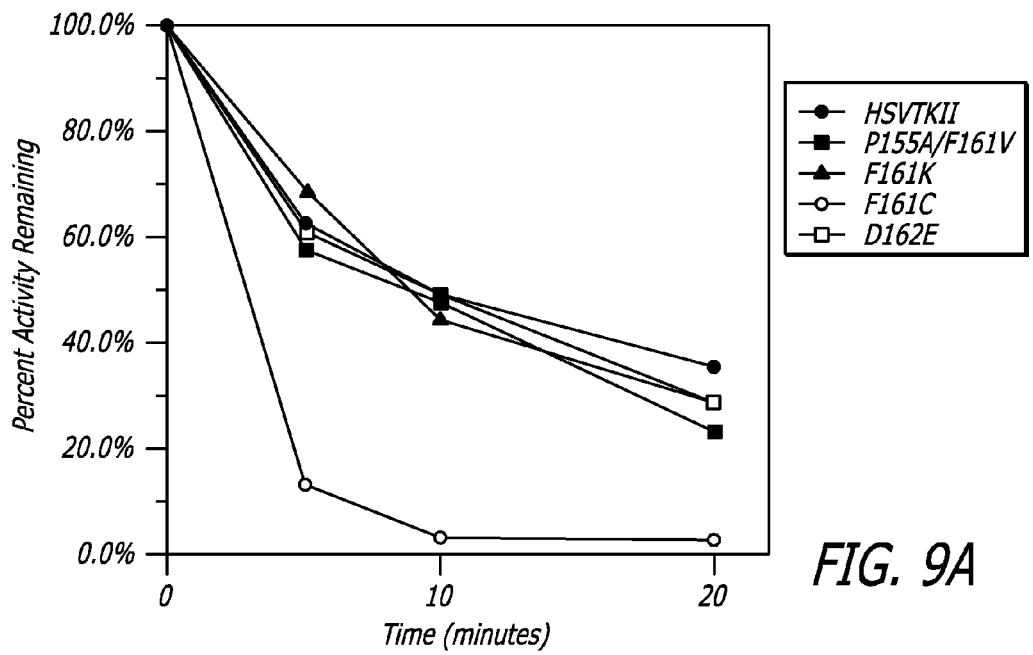
FIGS. 9A and 9B are two graphs which show the thermal stability of high activity (A) and low activity (B) TK mutants.

In the assays for colony formation on TK selection plates, several mutants were unable to complement KY895 at 42° C., suggesting that these mutant TKs were temperature-sensitive. To substantiate this observation, cell-free translation products were incubated at 42° C. for increasing times prior to being assayed for enzyme activity. Briefly, cell free translation ("CFT") products of each high-activity mutant, -RNA, and HSVTKII samples were diluted 1/9 and incubated for 0, 5, 10, and 20 minutes at 42° C. The preincubated samples were then assayed for 5 minutes (P155A/F161V and F161I) or 20 minutes (-RNA, HSVTKII, F161C, and D162E). The percent of activity remaining was determined with the untreated samples set at 100%. As shown in FIG. 9A, except for F161C, all high-activity mutants displayed thermal stabilities similar to HSVTKII after 42° C. preincubation periods as long as 60 minutes (data not shown). Because F161C lost greater than 90% of enzyme activity within the first 20 minutes at 42° C., shorter incubation periods at 42° C. were performed (0, 5, 10, and 20 minutes). F161C was exceptionally thermolabile demonstrating a ~85% activity loss after only 5 minutes at 42° C.

Figure 9B:
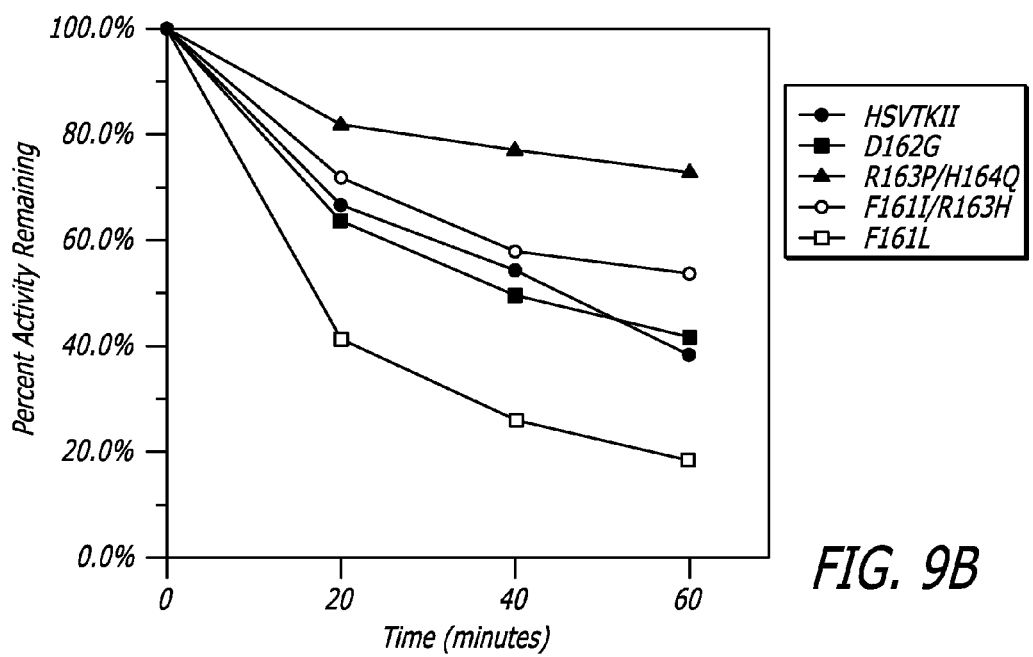

Low-activity mutant CFT products were diluted 1/5 and incubated for 0, 20, 40, or 60 minutes at 42° C. The preincubated samples were then assayed in triplicate for the thymidine phosphorylation for 60 minutes. The percent of activity remaining was determined using the untreated (time 0) sample as 100%. As shown in FIG. 9B, for the low-activity mutant subset one translation product (F161L) was more thermolabile that HSVTKII. Others in this set (R163P, F161I/R163H, H164Q, and D162G) were equivalent to HSVTKII.

G. Substrate Specificity Assays

Three of the mutants (P155A/F161V, F161I and F161C) were assayed in triplicate for the relative levels of phosphorylation using thymidine, deoxycytidine, ACV, GCV, or AZT as substrates. Briefly, forty-eight micromoles of each tritiated substrate was used in each assay reaction. Translation products were diluted for each nucleoside assay as follows (translation/H$_2$O): 1/100, thymidine; 2/3, deoxycytidine, GCV, and AZT; 4/1, ACV. Each set of assays was incubated for 2 hours at 30° C. and the amount of phosphorylated product determined.

Figure 10:
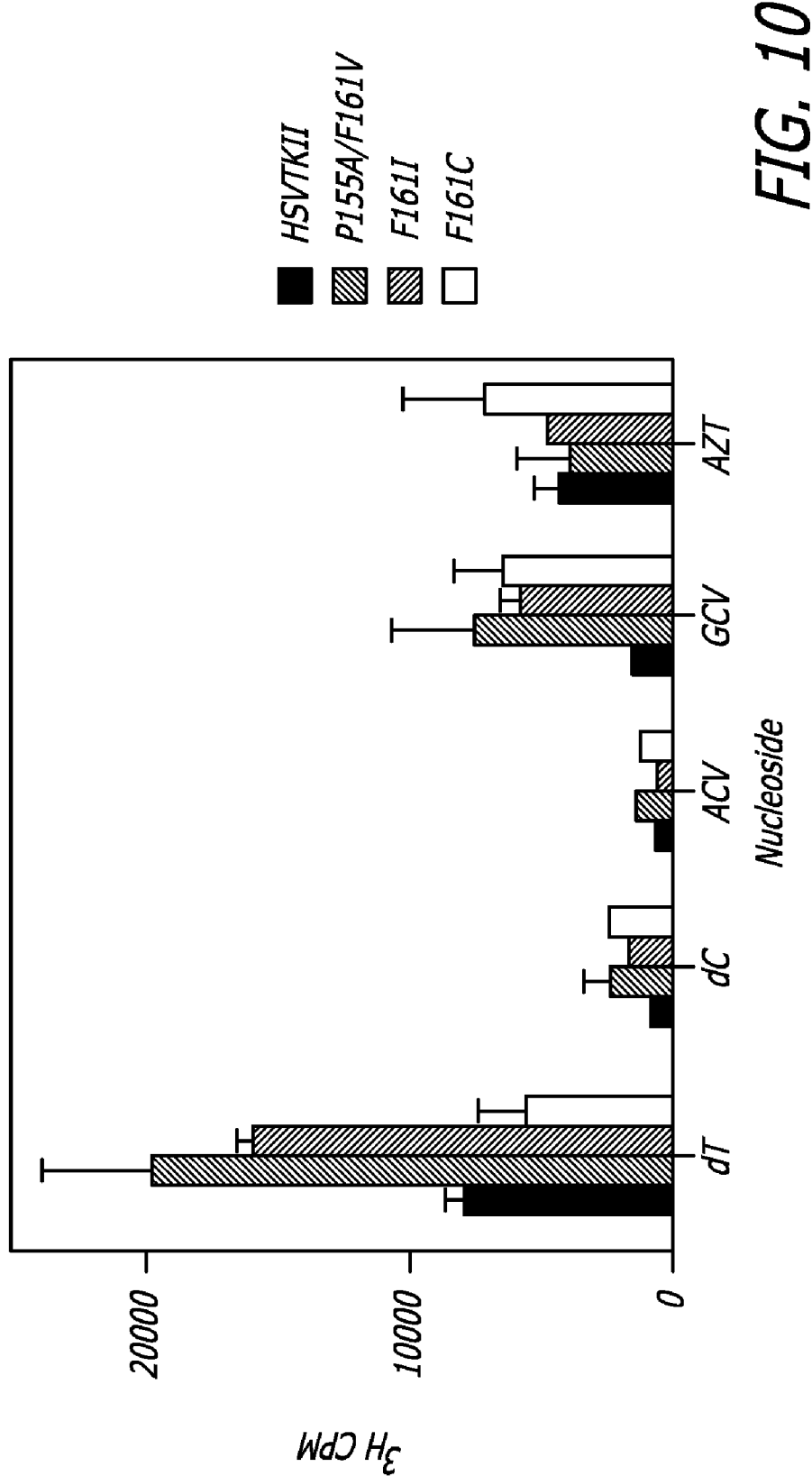
FIG. 10 is a bar graph which depicts a phosphorylation of nucleosides and nucleoside analogs by mutant and wild-type thymidine kinases.

The counts per minute of each set of assays were adjusted, and plotted as 30 shown in FIG. 10. Briefly, both P155A/F161V and F161I displayed an elevated capacity to phosphorylate thymidine relative to HSVTKII, 2.6- and 2.2-fold, respectively. Phosphorylation of deoxycytidine by the mutant enzymes ranged from 1.9- to 2.8-fold over the wild-type enzyme (F161I, 1.9-fold; F161C, 2.8-fold; P155A/F161V, 2.8-fold). Two mutants appeared to share an increased ability to phosphorylate ACV (2.4- and 2-fold over HSVTKII by F155A/F161V and F161C, respectively). All mutants demonstrated approximately wild-type levels of AZT phosphorylation. All mutants assayed appeared to share a large increase in GCV phosphorylation at 3.9-5.2-fold compared to wild-type phosphorylation levels.

Example 4

Analysis of TK Mutants with Altered Catalytic Efficiencies

In order to identify mutants with altered catalytic activity, 190 of the TK mutants isolated in Example 1 (TKF) were analyzed in the assays set forth below.

A. Colony Formation Ability As A Functional Thymidine Uptake

The protein content of the purified enzymes was estimated by a modification of the Bio-Rad protein assay. A standard curve was established using BSA and 25 µl of Bio-Rad reagent in a final volume of 125 ul. The amount of protein was determined by measuring the OD at 595 nm and comparing it to that of BSA.

In order to identify mutants with altered TK activity, a secondary screening protocol was designed based on the ability of the mutants to grow on medium containing different concentrations of thymidine (Table I). Briefly, it was first established that 1.0 and 10.0 µg/mL are the minimum and maximum concentrations of thymidine in the medium that supports the growth of E. coli harboring the wild-type tk plasmid. Since E. coli harboring the wild-type plasmid are unable to form visible colonies on TK-selection medium containing low thymidine (0.05 µg/mL), it was postulated that growth at this thymidine concentration might be indicative of mutants with an increased ability to phosphorylate thymidine. Accordingly, 0.05 µg/mL thymidine was used to select for variants with high TK activity and 20 µg/ml thymidine for variants with low activity.

Table I below shows the ability of selected mutants to functionally complement tk$^-$ E. coli KY 895 as a function of increasing thymidine concentration. When all the 190 TK variants and the wild-type were subjected to screening at the thymidine concentrations indicated in Table I, only one, TKF 36, formed colonies at the lowest thymidine concentration tested (0.05 µg/mL). On the other hand, only TKF 41 grew at the highest concentration of thymidine in the medium. All of the other 188 mutants and the wild-type formed visible colonies on medium containing 1 µg/mL thymidine.

TABLE I

COLONY FORMING ABILITY OF TK$^-$ E. COLI KY895
TRANSFORMED WITH WILD-TYPE AND MUTANT PLASMIDS,
AS A FUNCTION OF THYMIDINE CONCENTRATION

| | Thymidine concentration (µ/mL)$^a$ | | | | |
|---|---|---|---|---|---|
| Mutant | 0.05 | 1 | 2 | 10 | 20 |
| Wild-type | −$^a$ | +a | + | ±$^b$ | − |
| TKF 36 | + | + | + | ± | − |
| TKF 41 | − | − | + | + | +$^c$ |
| TKF 52 | − | + | + | + | − |
| TKF 99 | − | + | + | + | − |
| TKi 208$^d$ | − | + | + | + | − |

Colony formation was determined after incubation at 37° C. for 24 hours.
$^a$+ and − indicate the ability or inability of E. coli harboring different plasmids to form visible colonies on the indicated TK-selection media.
$^b$±indicates initial cell growth: cell death was apparent after incubation for 20 hours and may be due to the nucleotide pool imbalance generated by excessive phosphorylation of thymidine in the mutant and wild-type clones.
$^c$Since TKF 41 seemed to be a very low activity clone, overexpression of this mutant TK was necessary for the survival of E. coli on TIC-selection medium. pMCC and pMDC expression vectors have a temperature-sensitive repressor gene c1857 which becomes inactive at 42° C. and, hence, there is overexpression of TIC and subsequent cell death. In order to obtain controlled expression, screening was performed at 37° C. However, TKF 41 containing E. coil was incubated at 42° C. on 20 µg/mL thymidine containing TK-selection medium.
$^d$TKI 208 was obtained from the library described above in Example 2.

B. Sequence Analysis of High and Low Activity Clone

Wild-type tk and selected mutants were sequenced as described above in Example 2. Table II shows the nucleotide and deduced amino acid sequences of the wild-type tk and selected mutants for codons 165 to 175. Briefly, TKF 36, the mutant that forms colonies on low thymidine-containing medium, contains only a single amino acid substitution (Ala168→Ser), whereas TKF 41 contained four substitutions: Pro165→Ser, Ala167→Gly, Leu170→Gln and Ala174→Val. Interestingly, TKF 52 has a different amino acid substitution (Ala168→Thr) at the same position as TKF 36, but is unable to form colonies on low thymidine-containing medium. TKF 99 contains two amino acid substitutions (Cys 171→Leu and Ala 174→Thi). TKI 208 has a single nucleotide substitution which results in a Leu170→Val substitution.

TABLE II

NUCLEOTIDE AND DEDUCED AMINO ACID SEQUENCES OF THE WILD-TYPE AND MUTANT TK ENZYMES AT THE TARGET REGION

| | 165a | 166 | 167 | 168 | 169 | 170 | 171 | 172 | 173 | 174 | 175 | SEQ ID |
|---|---|---|---|---|---|---|---|---|---|---|---|---|
| Wild-type | ccc | atc | gcc | gcc | ctc | ctg | tgc | tac | ccg | Gcc | gcg | 12 |
| | pro | Ile | Ala | Ala | Leu | Leu | Cys | Tyr | Pro | Ala | Ala | 13 |
| TKF36 | ccc | Atc | gcc | Tcc | ctc | ctg | tgc | tac | ccg | Gcc | gcg | 14 |
| | Pro | Ile | Ala | SER | Leu | Leu | Cys | Tyr | Pro | Ala | Ala | 15 |
| TKF41 | Tcc | atc | gGc | gcc | ctA[b] | cAG | tgc | tac | ccg | gTc | gcg | 16 |
| | SER | Ile | GLY | Ala | Leu | GLN | Cys | Tyr | Pro | VAL | Ala | 17 |
| TKF52 | ccc | atc | gcc | Acc | ctg | ctg | tgc | tac | ccg | gcc | gcg | 18 |
| | Pro | Ile | Ala | THR | Leu | Leu | Cys | Tyr | Pro | Ala | Ala | 19 |
| TKF99 | ccc | atc | gcc | gcc | TtA | ctg | tTA | tac | ccg | Acc | gcg | 20 |
| | Pro | Ile | Ala | Ala | Leu | Leu | LEU | Tyr | Pro | THR | Ala | 21 |
| TKI208 | ccc | atc | gcc | gcc | ctc | Gtg | tgc | tac | ccg | gcc | gcg | 22 |
| | Pro | Ile | Ala | Ala | Leu | VAL | Cys | Tyr | Pro | Ala | Ala | 23 |

[a]Shows the codon number of the target region that was degenerated. The wild-type nucleotide and amino acid sequences are shown below the codon number.
[b]The silent mutations. No other nucleotide changes were observed in the region sequenced (spanning codons 140-182). Each template was sequenced twice.
Substituted nucleotide and amino acid residues are shown in bold capital letters.

C. Thymidine Uptake in *E. Coli* Harboring Wild-Type and Mutant TK Plasmids

In order to ascertain the actual level of thymidine uptake in *E. coli* harboring wild-type or mutant plasmids, the following assays were performed.

1. [Methyl-H]Thymidine Uptake Assay

Figure 11:
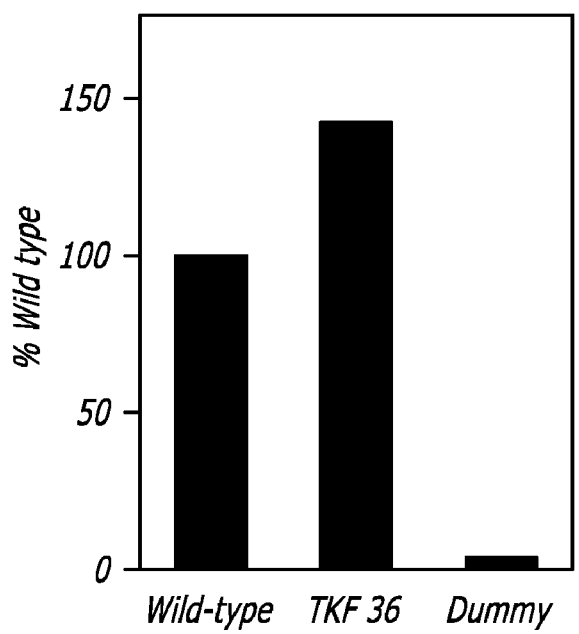
FIG. 11 is a bar graph which indicates TK activity of wild-type, TKF36, and dummy (pMDC) plasmids.

[Methyl-$^3$H]thymidine uptake in *E. coli* harboring wild-type or mutant plasmids was determined essentially as follows. Briefly, overnight cultures of *E. coli* containing pMDC (inactive TK), a plasmid containing wild-type TK, or TK36 were diluted 1:100 with LB-medium containing 100 μg/mL of carbenicillin, grown to 0.1 OD at $A_{550}$, shifted to 37° C. and incubated with vigorous shaking. Once an OD of 1.0 was attained, the culture was brought to room temperature (~25° C.) and thymidine was added to 1.0 mL aliquots at a final concentration of 0.21 μM (0.16 μCi [methyl $^3$H]thymidine). After incubation for 0, 5, 10, 20, 30 and 60 s at 22° C., 50 μl aliquots were transferred onto nitrocellulose filters (0.45 μm), washed under vacuum with 10 mL of chilled 50 mM Tris-HCl, pH 7.4, 0.9% NaCl, dried and counted in a scintillation counter using scintiverse BD (Fisher). Results are shown in FIG. 11. Briefly, there was essentially no thymidine uptake in *E. coli* harboring pMDC. The amount of thymidine uptake in *E. coli* harboring TKF 36 was 42% greater than in *E. coli* harboring the wild-type plasmid (18 pmol/$10^8$ cells compared to 12.7 pmol/$10^8$ after incubation for 10 s).

2. Incorporation of [Methyl-$^3$H]Thymidine into Acid-Insoluble Material

The amount of TK activity in crude *E. coli* extracts containing the wild-type and mutant plasmids was determined indirectly by measuring the incorporation of thymidine into acid-insoluble material.

Briefly, cultures were grown as described above under section 1. To 0.5 mL of culture, thymidine was added to a final concentration of 1.32 μM (0.2 μCi [methyl-$^3$H]thymidine). A 30 μl aliquot was taken out after designated times of incubation and added to 2.0 mL of cold 5% perchloric acid. The precipitate was washed and radioactivity incorporated into an acid-insoluble material was determined essentially as described by Dube et al., 1991.

Figure 12:
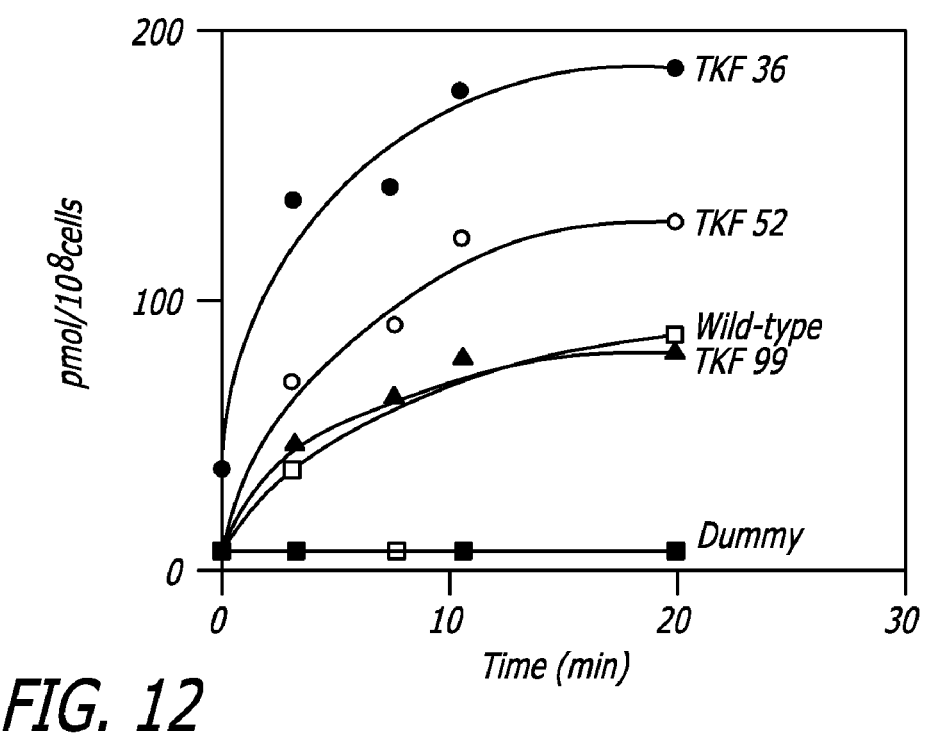
FIG. 12 is a graph which indicates the thymidine uptake activity of cells containing TKF36, TKF52, wild-type plasmid, TKF99, or dummy plasmids (pMDC) over time.
Figure 13:
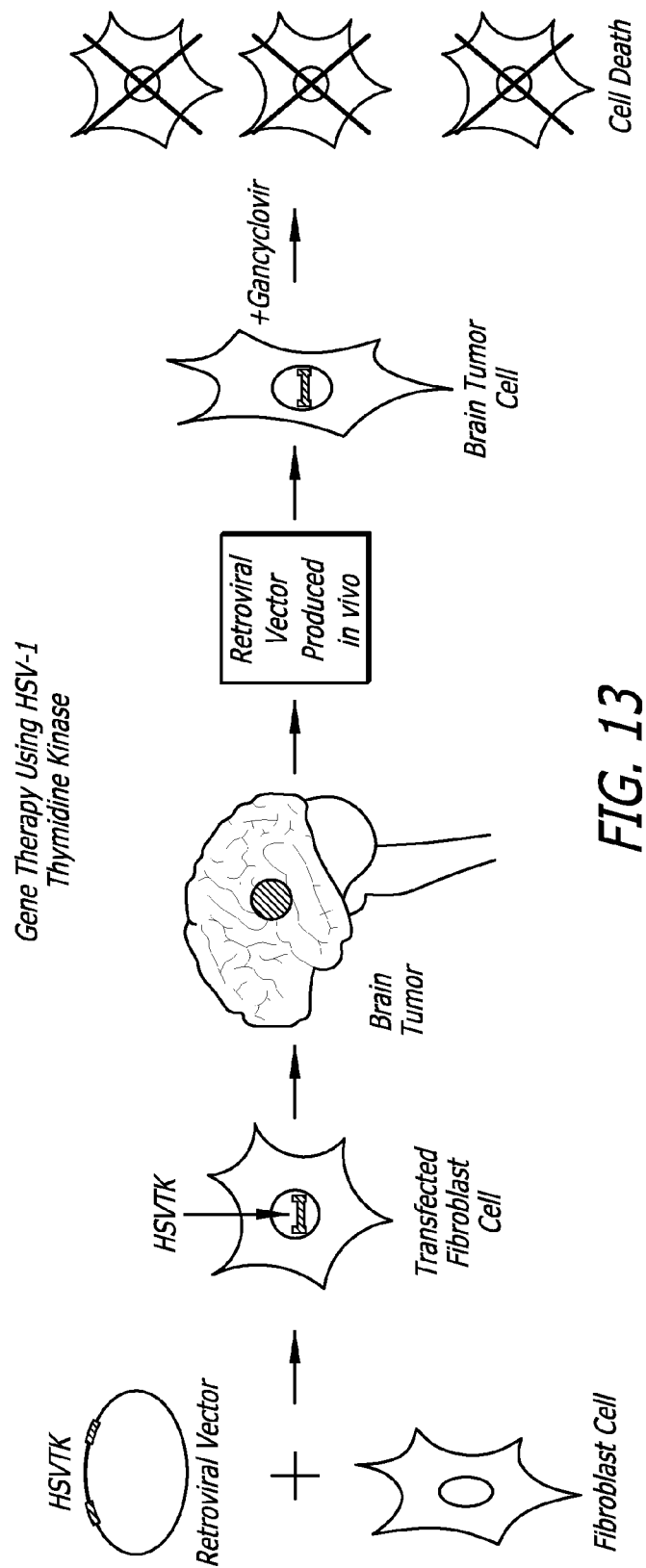
FIG. 13 is a schematic illustration of one representative example of gene therapy utilizing an HSVTK mutant.

FIG. 12, shows that the incorporation of [methyl-$^3$H]thymidine into an acid-insoluble product is more rapid with TKF 36 *E. coli* than with *E. coli* harboring the wild-type plasmid or the other tk mutants tested. One of the mutants, TKF 99, having two amino acid substitutions (Cys171→Leu and Ala174→Thr) exhibited the same rate of thymidine incorporation as did the wild-type. TKF 52 contains an Ala168→Thr substitution (compare Ala168→Ser in TKF 36) and is unable to form colonies in the lowest thymidine-containing TK-selection medium (Table I), yet incorporates thymidine into acid-insoluble material at a rate greater than that of wild-type but less than that of TKF 36.

D. Purification of Wild-types and Mutant TKS

Crude extracts of the different mutants were obtained from 11 cultures that were grown at 30° C. to 0.1 OD at $A_{550}$, shifted to 37° C. and grown to 1.0 OD. The cells were harvested by centrifugation at 4° C., washed with 25 mL of a solution containing 25% (w/v) sucrose, 50 mM Tris-HCl, pH 7.5, and 5 mM EDTA. After centrifugation the cell pellet (~5-6 g weight) was stored at −70° C. The cell pellet was thawed and suspended in 20 mL of buffer I (buffer I consisted of 10 vol. 50 mM Tris-HCl, pH 7.5, 10% sucrose mixed with 1 vol. 0.3M spermidine-HCl, 2.0M NaCl, 10% sucrose and 0.5 mM PMSF, pH 7.5). Once resuspension was uniform, 4.0 mL of buffer I containing 6.25 mg of lysozyme was added. The suspension was poured into a chilled centrifuge tube and placed on ice for 30 minutes. If cells did not lyse within 30 minutes, the tube was placed in a 37° C. waterbath for 4-6 minutes to enhance lysis. Once cells started to lyse as judged by increasing stringiness, 2-3 mL of chilled buffer I containing 50 μg/mL aprotinin and 2 μg/mL of each leupeptin and pepstatin, was added to a final volume of 25 mL and the mixture was centrifuged at 28,000 r.p.m. for 1 hour at 4° C. and the supernatant was stored at 70° C.

The wild-type and mutant TKs were purified by affinity chromatography on a matrix of p-aminophenylthymidine 3'-phosphate coupled to CH-Sepharose 4B (Pharmacia) as described by Kowal and Marcus (*Prep. Biochem.* 6:369-385, 1976) with modification by Lee and Cheng (*J. Biol. Chem.* 251:2600-2604, 1976). All buffers used in the purification of TK contained 5 mM DTT, 50μ/mL aprotinin, 2 μg/mL each of leupeptin and pepstatin and 1 mM PMSF unless otherwise indicated. A 7 mL bed-volume column was equilibrated with buffer A (0.1 M Tris-HCl, pH 7.5, 10% glycerol) and then loaded with ~25 mL of the unfractionated supernatant at a rate of 8-10 mL/h. The column was recirculated with the flow-through twice and then washed sequentially with ten bed-volumes each of buffer B (0.1 M Tris-HCl, pH 7.5, 0.5 M KCl, 10% glycerol) followed by buffer A. TK was eluted with a linear gradient of thymidine (0-600 μM) using 30 mL each of buffer A and buffer C (0.3 M Tris-HCl, pH 7, 4, 50 mM KCl, 10% glycerol). TK assay was performed on all the fractions and peak TK fractions were pooled and dialyzed against three changes of 2l of dialysis buffer (50 mM Tris-HCl, pH 7.4, 5 mM DTT, 10% glycerol). In the final dialysis, protease inhibitors were omitted from the buffer and the dialyzed fractions were aliquoted and stored at −70° C. The column was washed thoroughly twice by using the same washing and elution protocols as described above prior to application of each extract preparation.

The protein content of the purified enzymes was estimated by a modification of the Bio-Rad protein assay. A standard curve was established using BSA and 25 μl of Bio-Rad reagent in a final volume of 125 ul. The amount of protein was determined by measuring the OD at 595 nm and comparing it to that of BSA.

[Methyl-3H]Thymidine Uptake

Results are shown in FIG. 11. Briefly, there was essentially no thymidine uptake in *E. coli* harboring pMDC. The amount of thymidine uptake in *E. coli* harboring TKF 36 was 42% greater than in *E. coli* harboring the wild-type plasmid (18 pmol/$10^8$ cells compared to 12.7 pmol/$10^8$ after incubation for 10 s).

The amount of TK activity in crude *E. coli* extracts containing the wild-type and mutant plasmids was determined indirectly by measuring the incorporation of thymidine into acid-insoluble material.

E. Kinetic Parameters of Purified Mutant Thymidine Kinases

The three cellular parameters so far studied suggest that TKF 36 is a more active enzyme than any of the other mutant enzymes tested or the wild-type. In order to determine the kinetic parameters of catalysis, wild-type, TKF 36 and three other mutant thymidine kinases were purified to near homogeneity using affinity chromatography as described above. The purified wild-type, TKF 36 and TKI 208 were examined by electrophoresis in an SDS-PAGE system and were found to exhibit a single prominent band that migrated at 43 kDa, which was judged to be 95% homogeneous by silver staining.

Kinetic parameters were determined essentially as described below. Briefly, TK assay mixtures (50 μl) contained 50 mM Tris-HCl, pH 7.5, 5 mM ATP, 4 mM MgCl$_2$, 2.5 mM DTT. 12 mM KCl, 018 mg/mL BSA, 5% glycerol, 1 μM thymidine (0.3 μCi [methyl-$^3$H]thymidine) and the indicated amounts of purified enzymes. The kinetics of thymidine phosphorylation were determined by varying the unlabeled thymidine concentration (0-4.0 μM) and known amount of purified enzymes (the sp. acts of the purified TKs were 1.1, 3.0, 0.5, 0.34 and 0.01 units for wild-type. TKF 36, TKI 208, TKF99 and TKF41, respectively). One unit of enzyme is defined as the amount that phosphorylates 1.0 pmol of thymidine to thymidylic acid in 1 minute under the conditions described above. Incubation was at 34±1° C. for 10 minutes. The reaction was stopped by the addition of 1 mM cold thymidine. Half of the reaction mix was pipetted onto a DEAE-cellulose disc (25 mm) and the disc was dipped in distilled water (1 minute) followed by four washes each in 10 mL of absolute ethanol. The adsorbed products on the disc were counted in a scintillation counter. The kinetic parameters $K_m$ and $V_{max}$ were determined by using the Cleland SUBIN program (Cleland, *Methods Enzymol.* 63:103-138, 1979) and the values for $k_{cat}$ were calculated from the equation $V_{max}=k_{cat}[E]o$, where [E]o is the total enzyme concentration.

Results of these assays are summarized in Table III. Ala168→Ser substitution in TKF 36 resulted in a 4.8-fold enhancement in $k_{cat}$. None of the other purified mutant enzymes (TKF 41, TKF 99 and TKI 208) that were analyzed exhibited an increase in $k_{cat}$ compared to that of the wild-type TK. A 2.2-fold decrease in $k_{cat}$ results form the Leu170→Val substitution in TKI 208, whereas two of the other tk mutants, TKF 99 and TKF 41, with decreased efficiencies in the in vivo assays, exhibited a 28- and 34 700-fold decrease in $k_{cat}$. Table III also presents the Michaelis constant ($K_m$) for the mutants and wild-type with thymidine as a substrate. The apparent $K_m$ for the wild-type enzyme was 0.47 μM, which agrees well with previously reported values (Jamieson and Subak-Sharpe, *J. Gen. Virol.* 24:481-492, 1974; Elion, *Am. J. Med.* 73:7-13, 1982; Waldman et al., *J Biol. Chem.* 258:11571-11575, 1983). Even though TKF 36 showed a higher $k_{cat}$ value its affinity for thymidine, as reflected in the $K_m$, is 6.2-fold lower than the wild-type TK. TKI 208, TKF 41 and TKF 99 have a similar $K_m$ to that of the wild-type. Interestingly, the $k_{cat}/K_m$ value of TKF 36 [$2.0\times10^6$ s$^{-1}$M$^{-1}$] is not very different from the wild-type [$2.5\times10^6$ s$^-$M$^{-1}$], while TKI 208, TKF 99 and TKF 41 exhibit lower values of $1.57\times10^6$, $0.15\times10^6$ and $0.00012\times10^6$ S$^{-1}$M$^{-1}$, respectively.

TABLE III

COMPARISON OF KINETIC PARAMETERS OF THE THYMIDINE KINASES

| Enzyme | $K_m$ (μM) | $k_{cat}$ ($^{1/s}$) |
|---|---|---|
| Wild-type | 0.47 ± 0.1[a] | 1.2 |
| TKF 36 | 2.90 ± 0.01 | 5.7[b] |
| TKF 41 | 0.28 ± 0.16 | 3.5 × 10$^{-5b}$ |
| TKF 99 | 0.29 ± 0.002 | 0.04[b] |
| TM 208 | 0.35 ± 0.008 | 0.5[b] |

[a]Data presented as ±SE.
[b]The P value is <0.02 compared to the wild-type.

Example 5

Selective Killing of Cells Transfected with Retroviral Vectors Containing Mutant HSV-1 TK The example describes the construction of retroviral vectors which express a type 1 Herpes Simplex Virus thymidine kinase, a proline to alanine mutation at position 155, and a phenylalanine to valine mutation at position 161.

A. Vector Construction

The thymidine kinase gene from P155A/F161V is utilized to replace the wild-type HSV tk sequences in the Moloney Murine Leukemia Virus ("MoMLV") based vector G1TkSvNa.90 from Genetic Therapy, Inc. (Gaithersburg, Md.; see Ram et al. *Cancer Research* 53:83, 1993). In particular, the mutant tk gene is inserted downstream from the 5' long terminal repeat sequence, which the tk gene uses as a promoter. This vector also contains an neomycin phosphotransferase gene (neo) which is expressed from an SV40 early promoter.

B. Producer Cell Line

The retroviral vectors described above may then be packaged by the amphotropic retroviral packaging cell line GP+envAml2 (U.S. Pat. No. 5,278,056) after calcium phosphate transfection. A vector containing the gene for β-galactosidase is used as a control vector. The cloned vector producer cells are maintained in culture containing Dulbecco's modified Eagle's medium with 10% fetal calf serum, 2 mM glutamine, 50 units/ml penicillin, 50 µg/ml streptomycin and 2.5 µg/ml Fungizone. Prior to administration, the media is removed and the cells rinsed with saline. The monolayers are trypsinized for 5-10 minutes at 37° C., collected, washed twice and resuspended at $5\text{-}10 \times 10^8$ cells/ml.

C. In Vitro Sensitivity to GanciclQyit

To assess the sensitivity of cells transduced with the mutant or the wild-type tk gene containing vectors, rat 9L glioma cells and human U251 glioblastoma cells are transduced in vitro by exposing the cells to supernatant containing replication incompetent vector particles. The transduced cells are selected by including G148 (1 mg/ml) in the culture medium. Nontransduced, HSV tk wild-type transduced and HSV tk mutant transduced cells are then evaluated for their sensitivity to increasing levels of ganciclovir. The level of DNA synthesis is determined by tritiated thymidine incorporation after various ganciclovir exposure times and ganciclovir levels. Cell viability is determined by plating the cells in 10 cm tissue culture plates in the absence or presence of various ganciclovir concentrations, and counting the number of cells at 24 hour intervals.

D. In Vivo Transduction

The efficiency of in situ transduction of and relative level of vector gene expression in the tumor cells is determined using the β-galactosidase containing vector. Briefly, Fischer 344 rates are anesthetized and injected with $4 \times 10^4$ syngeneic 9L gliosarcoma cells using a 10 µl Hamilton syringe connected to a stereotaxic injection apparatus. After ten days, the same stereotaxic position is used to directly inject $1.5 \times 10^6$, $3 \times 10^6$ or $6 \times 10^6$ HSVtk (wild-type or mutant) β-galactosidase transduced or nontransduced producer line cells, and producer cell line supernatants into the 9L tumor. As a control, rats are injected with the same volume of sterile saline instead of cells. Ganciclovir is then administered and the rats are sacrificed to determine the anti-tumor effect. A histological examination is also performed.

E. Dose Optimization of Ganciclovir

Rats are injected intracerebrally with $4 \times 10^4$ HSVtk (wild-type or mutant) or (β-galactosidase transduced rat 9L producer cells. Seven days post inoculation, ganciclovir is administered i.p. at 5, 20 or 15 mg/kg twice daily for 7 days. Control rats receive i.p. saline injections. All rats are sacrificed after the ganciclovir treatment and the brains and tumors removed for weight determination and histological examination.

F. Tumor Regression with Wild-type and Mutant HSV tk Transduction and GCV

Based on the results of the ganciclovir dose optimization, rat tumors inoculated with transduced or nontransduced producer cells or produced cell supernatant are administered ganciclovir doses for a specific time period. Antitumor effects are determined by determination of tumor weight and histological examination.

Example 6

The Use of VZV TK Mutants as Targets for Selectable Homologous Recombination

This example describes the use of a mutant Varicella Zoster Virus thymidine kinase ("VZV tk") as a target for homologous recombination in the construction of stable transfected cells lines, strains or recombinant viruses. In particular, the construction of vaccinia viruses as cloning vectors containing mutant VZV TKs for the selection of recombinant viruses in $TK^+$ cell lines is described.

A. Construction of Recombinant Vaccinia Virus Plasmids Containing VZV TK Mutants VZV tk genes (wild-type and mutant) are cloned into a recombinant plasmid behind the vaccinia virus 7.5 K promoter for constitutive gene expression. In addition the neomycin phosphotransferase gene is cloned after the 3' end of the VZV tk gene to serve as a selectable marker. The 5' or 3' regions of the vaccinia virus encoded thymidine kinase gene flanks the 5' end of VZV tk gene and the 3' end of the neomycin phosphotransferase gene (neo). This allows for the insertion of the VZV tk gene into the viral genome and the concomitant inactivation of the vaccinia thymidine kinase gene. The remainder of the plasmid is based on pUC and contains an ampicillin resistance gene and a ColE1 origin of replication for maintenance of the plasmid in E. coli.

B. Construction of Recombinant Poxviruses

The VZV tk (wild-type or mutant)+neo recombinant plasmid or recombinant plasmid containing only the neo gene is cotransfected with the wild-type vaccinia virus into BSC40 cells. Recombinant viruses are selected by resistance to G418. After several rounds of plaque purification, the recombinant viruses are subjected to plaque hybridization and DNA analysis in order to confirm the insertion and location of the foreign genes.

C. Dose Optimization of Ganciclovir

Vaccinia virus infected and uninfected BSC40 cells are subjected to treatment with various doses of ganciclovir in order to determine the tolerance level. Cells infected with recombinant viruses expressing VZV TKs and neo or those expressing only neo will be grown in the presence of various levels of ganciclovir. VZV tk gene containing viruses are more sensitive to ganciclovir treatment than the cells alone or those infected with wild-type vaccinia virus. A level of ganciclovir is selected from the results of this experiment to select for the loss of sensitivity to ganciclovir for homologous recombination with other genes to be inserted into the VZV tk locus.

D. Selection of Recombinant VZV tk Poxviruses Using Ganciclovir

BSC40 is infected with the VZV tk recombinant virus in the presence of a recombinant plasmid carrying the gene to be introduced into the VV genome, abutted to the UV 7.5 K promoter cloned with VZV tk sequences flanking. Recombinant virus is selected with ganciclovir.

Any cell line stably transfected with the VZV tk gene can be the target for introduction of foreign genes by homologous recombination and for the selection of such an event by resistance to ganciclovir.

45

Example 7

Construction and Analysis of HSV-1 Thymidine
Kinase and HSV-1 DNA Polymerase Vectors A. Construction of Vectors Three constructs were made containing either the HSV-1 DNA polymerase gene, HSV-1 thymidine kinase gene or both.

a) pHSG576:HSVpol

The 5.5 kb HinDIII/EcoRI fragment from pGEM2-702 (David Dorsky, Univ. of Conn.) was cloned into pHSG576 (Sweasy and Loeb, *J. Biol. Chem.* 267: 1407-1410, 1992) in two steps:

1) The 2.4 kb PstI/EcoRI fragment was cloned into pHSG576igested with PstI and EcoRI. This clone was designated pHSG576: 1/2 poi.
2) The 3.1 kb HinDHI/PstI fragment of HSV DNA polymerase was cloned into pHSG576:1/2 pol digested with HinDIII and PstI. This clone was designated pHSg576: HSV DNA pol.

b) pHSG576:HSV-1 TK

The XbaI/BamHI fragment from pET23d:HSVTK (contains the HSV-1 TK NcoI-NcoI fragment in pET23d, Novagen) was blunt-ended and cloned into the SmaI site of pHSG576. The clone was designated pHSG576:HSV-1TK.

c) pHSG576:HSV pol/TK

This clone contains both the HSV-1 DNA polymerase and TK genes for coexpression from the same vector. It was created in a two step cloning protocol.

1) The XbaI/BamHI-bluntended TK fragment was cloned into the bluntended EcoRI site of pHSG576: 1/2pol (contains the 2.4 kb PstI/EcoRI fragment).
2) The 3.1 kb HinDIII/PstI fragment (5' end of the polymerase gene) was cloned into pHSG576:1/2pol/TK digested with HinDIII and PstI. This clone was designated pHSG576:HSVpol/TK.

B. Transformation of *E. Coli* with a DNA Polymerase Defect

*E. coli* JS200 (polA12recA718) was transformed with pHSG576:HSV DNA pol or pHSG576 DNA and plated on nutrient agar (NA) containing tetracycline (12.5 µg/mL) and chloramphenicol (34 µg/mL). Plates were incubated at 30° C. (permissive temperature). Single colonies were grown overnight in NB+tet+Cm. DNA was isolated from these cultures and used to transform JS200 again. From the second transformation several colonies from each were picked and used to inoculate NB 30+tet+Cm in the presence or absence of IPTG. After overnight growth at 30° C., a single loopful of each culture was spread in a diverging spiral of increasing dilution from the center of the plate. NA plates+tet+Cm+/−IPTG were incubated at 30° C. (permissive) or 37° C. (nonpermissive).

The growth pattern of cells containing pHSG576:HSV DNA pol displayed growth of single colonies (low cell density) at 37° C., while cells containing only the vector were unable to grow at low cell density at the nonpermissive temperature.

These results demonstrate that the Herpes DNA polymerase can complement the *E. coli* PolI defect in vivo.

46

Example 8

Construction and Analysis of TK Mutants with Mutations at Codons 159 to 161 and 168 to 170 Utilizing a 100% Random Library This example describes the construction and analysis of TK mutants that are mutagenized at codons 159 through 161 and 168 through 170.

Bacterial Strains. SY211 (BL21(DE3) tdk⁻, pLysS) is cured of pLysS by repeated passages on non-selective plates (no chloramphenicol). (SY211 is a gift from William Summers, Yale University, New Haven, Conn. and is described in Summers, W. C. and Raskin, P., *J. Bact.* 175:6049-6051, 1993). The resulting strain BL21(DE3) tdk is used in the genetic complementation assays for thymidine kinase activity. Other strains used are described in Example 3.

Cells. BHK tk-(ts13) cells (ATCC No. CRL-1632) are purchased from the American Type Culture Collection and cultured in DMEM+10% calf serum at 37° C. under 6% $CO_2$.

Materials. As described in Example 3.

A. Generation of TK Mutants

1 Construction of Random Insert

Two oligonucleotides are synthesized by Operon (Alameda, Calif.): MB126 (58mer) 5'-TGGGAGCTCA CATGCCCCGC CCCCGGCCCT CACCNNNNNN NNNGACCGCC ATCCCATC-3' (SEQUENCE ID No. 24) and MB127 (51mer) 5'-ATAAGGTACC GCGCGGCCGG GTAGCANNNN NNNNNGGCGA TGGGATGGCG G-3' (SEQUENCE ID No. 25). The N designates an equimolar mix of all four nucleotides during synthesis.

The purification of oligonucleotides, annealing, extension and 10 amplification by PCR is essentially as described in Example 3.

2. Generation of Random-Sequence Containing Libraries Vector Construction pET23d, purchased from Novagen, is the backbone for the construction of pET23d:HSVTK-Dummy. pET23d:HSVTK-Dummy is used in place of pMDC (described in Example 1 and 3) for insertion of random sequences. Briefly, a 1.7 kb NcoI/HinDIII fragment is purified from a restriction digest of pT7:HSVTKII (Example 3) and cloned into pET23d restricted with the same enzymes to generate pET23d:HSVTK. The dummy vector is constructed by replacing the tk sequences between the KpnI and SacI sites with the KpnI/SacI fragment from pMDC (Example 3).

Library Construction

Qiagen column purified pET23d:HSVTK-Dummy DNA is restricted with KpnI and SacI and the vector gel isolated using GenCleanII (Bio 101, La Jolla, Calif.) to remove the small insert fragment. This vector is ligated with the gel isolated PCR-amplified random fragment overnight at 16° C. with T4 DNA ligase.

3. Selection of TK Mutants

The ligated mixture is then used to transform BL21(DE3) tdk cells by electroporation as described in Example 3. The transformants are plated directly onto TK selection plates (Example 3) with a small fraction plated on 2×YT (16 g tryptone/10 g yeast extract/5 g NaCl/15 g BactoAgar per liter)+carbenicillin at 50 µg/ml (carb[50]) to determine the total number of transformants. The plates are incubated at 37° C. overnight and scored for growth on TK selection plates and the transformation frequency determined. Colonies that grew on the TK selection plates are picked and restreaked on fresh TK selection plates and 2×YT+carb[50] plates. Approximately 426 positive clones are identified from a library of 1.1×

$10^6$ transformants or 0.039% of all transformant conferred TK activity to *E. coli* BL21(DE3) tdk (FIG. 14).

B. Analysis of Mutants

1. Sequence of Selected and Unselected Clones

Figure 15:
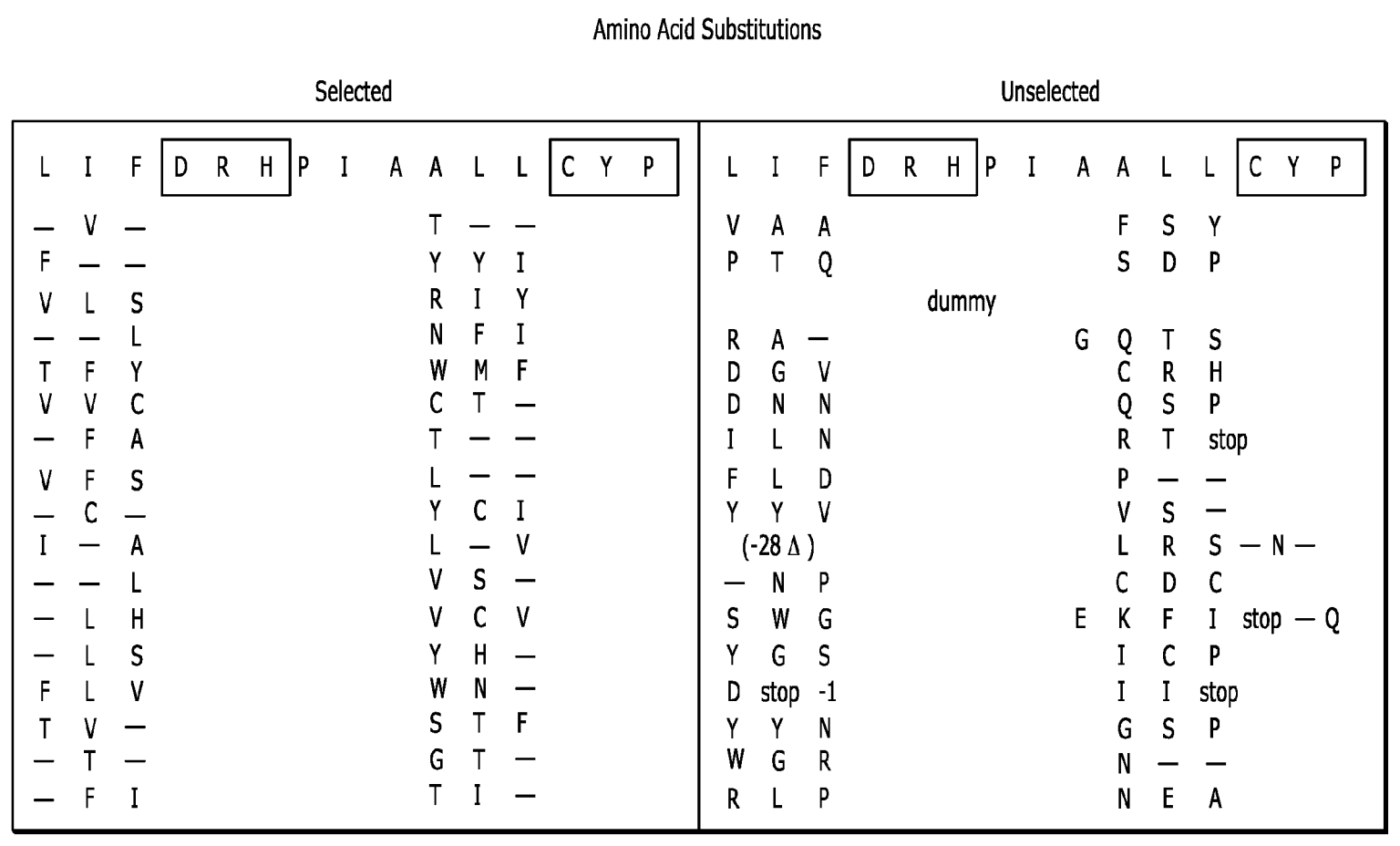

Seventeen clones that demonstrated TK activity (selected) or are taken from 2×YT+carb$^{50}$ plates (unselected) are successfully sequenced. DNA is isolated using Qiagen miniprep kits and subjected to double strand sequencing as described in Example 3. FIG. 15 shows the sequences from each group and demonstrates that the initial random oligonucleotides are randomized. In both selected and unselected tk genes, the introduction of secondary mutations at sites distal to the randomized region are observed. However, the mutations are primarily confined to two codons, 155 and 156. These mutations are most likely introduced by contamination during the synthesis of the original random oligonucleotides. All changes at codon 155 are silent. Changes at codon 156 resulted in alanine to valine, serine or proline alterations. Alignment studies indicate that position 156 is not conserved either for alanine nor for the type of amino acid at that position. Therefore, it is unlikely that these secondary mutations result in any real effect on the enzyme activity of the mutants. All selected mutants contained at least two amino acid changes.

2. Secondary Screening for GCV and ACV Sensitivity

Each of the 426 mutants is picked and used to inoculate 200 μl of TK selection medium (Example 3) in a 96 well microtiter plate format. All 426 clones are then serially diluted $10^4$ in 0.9% NaCl with a 48-prong replicator (Sigma, St. Louis, Mo.). 30 μl of the last dilution is spread onto TK selection plates containing 1 μg/ml thymidine plus varying concentrations of ganciclovir or acyclovir. Initially 2 μg/ml GCV is used and the clones unable to grow are scored as positives since any mutant with increased conversion of a pro-drug to an active toxin results in lethality. On 2 μg/ml GCV 197 clones are identified. Sequential plating on 1 μg/ml and 0.5 μg/ml GCV lead to the identification of 47 mutants. Plating on ACV plates (1 μg/ml) gave 116 ACV sensitive clones. To ensure that the clones are truly sensitive to the nucleoside analog and not simply scored because of the inability to grow on the lower thymidine concentrations used, the 47 GCV and 116 ACV clones are plated on TK selection plates containing thymidine at 1 μg/ml (no nucleoside analog). Almost half of the clones are unable to grow on low thymidine for a total of 26 GCV sensitive mutants and 54 ACV sensitive mutants. Results are shown in FIG. 16.

C. In Vitro Analysis

1. In Vitro Transcription and Translation.

Plasmid DNA is purified by Qiagen column chromatography. Transcription and translation of the 80 selected mutants is done as in Example 3 except that the isolated plasmids are not linearized prior to transcription. In vitro translation products are assayed in duplicate for thymidine, ganciclovir and acyclovir phosphorylation and compared to pET23d:HSVTK mRNA translation product assays (see Example 3).

2. Measurement of Enzyme Activity

Radiolabelled nucleosides are present in each assay at 1 μM, 7.5 μM and 7.5 μM for thymidine, ganciclovir and acyclovir, respectively. The level of activity is adjusted to reflect the level of protein synthesis as determined from the TCA precipitable counts from a duplicated translation with $^{35}$S methionine. For the majority of the 80 mutant enzymes, the level of thymidine, ganciclovir and acyclovir is less that 1% that of the wild-type TK. Ten mutant enzymes displayed greater that 10% phosphorylation with at least one of the nucleosides assayed. The nucleotide sequences are shown in FIG. 17. Several of the clones contained mutations outside the randomized region. Two clones, 30 and 84, have mutations that result in amino acid changes, A152V and A156S, respectively. Four clones contain in-frame deletions; three (226, 340 and 411) with −3 deletions and one (197) with a −6 deletion. All these mutations are centered around a GC-rich region which encodes for the peptide A P P P A. This proline rich peptide is likely to comprise a turn at the tip of a loop section. The loss of one or two amino acids may simply result in shortening of the loop. All of these mutants contain three to six amino acid alterations within the randomized region as shown in FIG. 18 with the respective levels of activity determined in vitro.

D. Effect of GCV and ACV on Mammalian Cells Expressing Mutant Thymidine Kinases

1. Subcloning into a Mammalian Expression Vector

Three mutant thymidine kinases are selected to evaluate for cell toxicity in vivo in the presence of ganciclovir or acyclovir. Mutant clones number 30, 75 and 132 and the wild-type thymidine kinase genes are restricted with NcoI and blunt-ended with Klenow. The gel isolated fragments (NcoI-blunt) are ligated to pCMV restricted with NotI and transformed into *E. coli* strain NM522. The wild-type TK gene in the wrong orientation relative to the CMV promoter is also used as a control. Qiagen column purified clones are sequenced to confirm orientation, sequence and the 5' junction region. The clones are designated pCMV, pCMV: TK-wrong, pCMV: TK, pCMV:30, pCMV:75 and pCMV:132.

2. Transfections

As an initial step to evaluate these mutants, the pCMV clones are introduced in the presence of a neomycin resistant marker plasmid (pSV2neo) into TS13 BHK tk⁻ cells (baby hamster kidney cells) by calcium phosphate precipitation using a modified version of Chen and Okayama (*Molec. Cell. Biol.* 7:2745-2752, 1987).

Briefly, the cell transfections are performed as follows. Approximately $5\times10^5$ ts13 BHK tk⁻ cells (ATCC CRL-1632) are plated on 100 mm dishes in DMEM+10% calf serum. For each transfection 1 μg of pSV2neo and 10 μg of a pCMV construct (pCMV, pCMV:TK-wrong (HSVTK in the wrong orientation relative to the promoter), pCMV:HSVTK, pCMV: 30, pCMV:75 or pCMV:132 DNA) in 0.25M $CaCl_2$ are mixed with 0.5 ml 2×BBS (see Chen and Okayama) and preincubated at 37° C. at 2.5% $CO_2$ for 24 hours. The $CaCl_2$/DNA mix is added dropwise to the plates and mixed in well. After a 24 hour incubation at 37° C. in a 2.5% $CO_2$ wet incubator, the cells are rinsed twice with Dulbecco PBS minus Ca/Mg and fed with fresh DMEM+10% calf serum. Plates are incubated at 37° C. with 6% $CO_2$. After 72 hours post-transfection the cells are split 1:3 and plated in DMEM+10% calf serum containing G418 at 600 μg/ml.

3. Selection and $ED_{50}$ Determinations

The cells are selected on G418 (600 μg/ml) at 37° C. for 17 days. During this time the plates are pooled (for each DNA transfection) and split three times at a ratio of 1:3. Approximately 30-40 clones are selected in this manner for each transfected DNA containing a tk gene in the correct orientation. The pCMV and pCMV:TK-wrong transfections yielded between 130 and 140 clones each. G418 resistant clones are harvested, pooled and plated at a density of 2000 cells/well in 100 µl DMEM+10% calf serum and 200 µl/ml G418+6% $CO_2$ in 96 well microtiter plates. A concentration range of either ganciclovir (0.125, 0.25, 0.5, 1, 2.5, 5, 7.5, 10 and 20 µM) or acyclovir (0.5, 1, 2.5, 5, 10, 25, 50, 75 and 100 µM) is added to each plate with 8 repeats of each concentration for each transfectant population (the no nucleoside analog controls each had 16 repeats). After three days in the presence of the nucleoside analog, Alamar Blue is added and 6 hours later the plates are scanned using a fluorometer as according to the manufacturer's protocol (Alamar Biosciences, Inc., Sacramento, Calif.). The plates are incubated a further 24 hours at 37° C. and scanned again.

Determination of the fluorescence level of cells incubated in the presence of Alamar Blue directly relates to cell viability. Subtraction of the background fluorescence allows one to plot the cell survival versus the nucleoside analog concentration to determine to effective dose for killing 50% of the cells ($ED_{50}$). The survival curves are plotted with data from the second scan and are shown in FIGS. 19 (GCV) and 20 (ACV).

Figure 19:
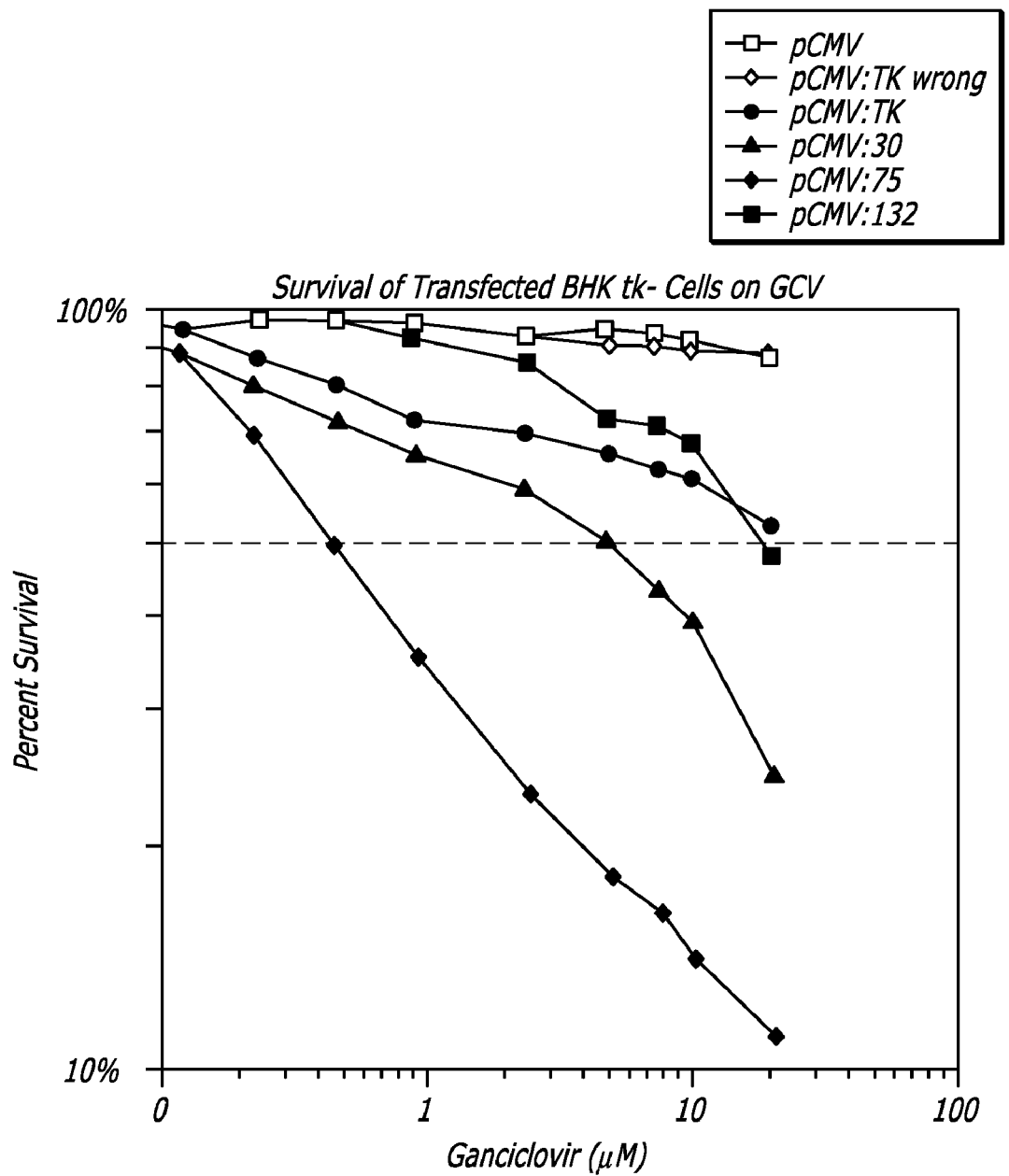
FIG. 19 is a graph which shows the survival of cells grown on GCV and transfected with various TK mutants.
Figure 20:
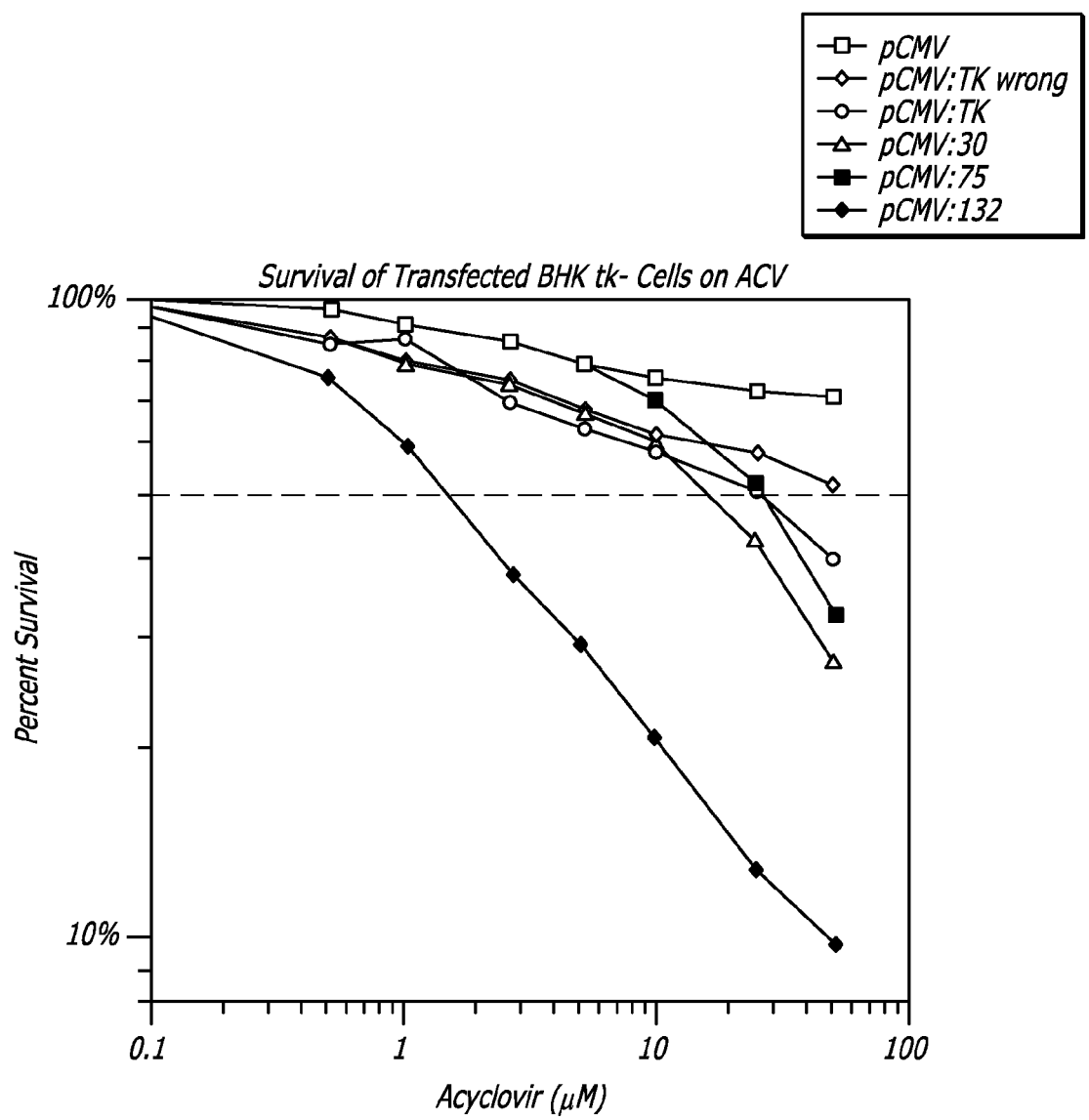
FIG. 20 is a graph which shows the survival of cells grown on ACV and transfected with various TK mutants.

After 4 days on nucleoside analog the effective doses for 50% cell killing with GCV and ACV are determined from FIGS. 19 and 20 (see Table IV).

TABLE IV

| | $ED_{50}$ GCV | fold over WT | $ED_{50}$ ACV | fold over WT |
|---|---|---|---|---|
| WT | 20 µM | 1 | 25 µM | 1 |
| 30 | 4.4 µM | 4.5 | 18 µM | 1.4 |
| 75 | 0.47 µM | 43 | 1.25 µM | 20 |
| 132 | 18 µM | 1.1 | 25 µM | 1 |

4. Enzyme Assays and Immunoblots

Cell extracts from 2.4×10⁶ pooled transfectants are assayed for thymidine, ganciclovir and acyclovir activity. The levels of phosphorylation corresponded very well with the activities determined in vitro (rabbit reticulocyte lysate translation products) and the amount of protein expression as determined by western blot analyses. No immunoreactive band is seen in the lanes corresponding to pCMV or pCMV: TK-wrong (TK gene in the wrong orientation). Both the wild-type TK (pCMV:HSVTK) and pCMV:132 transfected cell lysates exhibited roughly equivalent band intensities. The immunoreactive band for pCMV:30 cell lysates is substantially more intense (5-10 fold) and that of pCMV:75 is approximately half the pCMV:HSVTK band intensity for the equivalent cell number.

5. Testing Mutants in Glioblastoma Cell Lines

Blunt-ended NcoI fragments isolated from pET23d:HSVTK, pET23d:30 and pET23d:75 are cloned into the HpaI site of pLXSN (Miller and Rosman *BioTechniques* 7:980, 1989). Plasmid purification is done by Qiagen chromatography and the isolated DNA sequenced to confirm orientation and 5' junction regions. Stable transfectants of rat C6 glioblastomas (ATCC CCL-107) and a human glioblastoma cell line (SF767) are made as described above with the exception that pSV2-neo is not co-transfected since the neomycin phosphotransferase gene is encoded by pLXSN. Selection and analysis is essentially as described above.

E. Kinetic Analysis of Mutant Thymidine Kinases

1. Overexpression of Mutant and Wild-Type Enzymes

A single colony of pET23d:HSVTK, pET23d:30, pET23d: 75 and pET23d: 132 in BL21(DE3)tk cells is used to inoculate 5 ml of M9ZB medium (1% tryptone, 0.5% NaCl, 1×M9 salts, 1 mM MgSO₄, 100 µM CaCl₂ and 0.2% glucose) containing cabenicillin at 20 µg/ml. The culture is incubated at 37° C. overnight. The following day the 5 ml culture is used to inoculate 1 L M9ZB+cabenicillin at 20 g/ml and the culture allowed to grow at 37° C. to OD600 0.1. At that point IPTG is added to 0.4 mM and the culture incubated a further 3 hours. The cells are chilled on ice, pelleted by centrifugation and the pellets washed once in cell wash buffer (50 mM Tris, pH 7.5, 5 mM EDTA, 10% sucrose) prior to freezing the pellets at −70° C. The next day the cells are resuspended in 12 ml Buffer 1 (50 mM Tris, pH 7.5, 10% sucrose, 2 mM DTT, 5 mM EDTA, 1 mM PMSF) and the volume split into two 13 ml Oakridge ultracentrifuge tubes. 1 ml Buffer 1 containing 3 mg lysozyme is added to each tube and the tubes left on ice for 1 hr. An additional 1 ml Buffer 1+protease inhibitor mix is added and the tube spun at 35 krpm in a Sorvall T-1250 rotor at 4° C. The cleared supernatant is then aliquoted and frozen at −70° C.

2. Affinity Purification

A thymidylyl-sepharose column is used for a one step purification procedure (see Example 2). The 1 ml bed volume column is prepared by passing 10 ml Buffer 1 followed by 10 ml Absorption Buffer (50 mM Tris, pH 7.5, 10% sucrose, 2 mM DTT, 25 mM MgAc₂, 10 mM ATP) over the column. Two ml of the cleared lysate is mixed with 2 ml of Absorption Buffer and passed through a 0.2 cm filter. This mix is passed over the column 3 times. The column is washed with 5 ml Absorption buffer three times and the 5 ml fractions collected. To elute the enzyme, 3-1 ml fractions of Thymidine Buffer (300 mM Tris, pH 7.5, 10% sucrose, 2 mM DTT, 50 mM KCl, 600 µM thymidine) is passed over the column and each 1 ml fraction collected. The column is reactivated by loading on 10 ml High Salt Buffer (50 mM Tris, pH 7.5, 10% sucrose, 2 mM DTT, 0.5M KCl) and 10 ml 50 mM Tris, pH 7.5. The column is stored in 50 mM Tris pH 7.5+0.004% sodium azide. The extent of purification is monitored by Coomassie stained SDS:PAGE analysis and the concentration of purified protein determined using the BioRad Reagent (Bradford Reagent). The fraction containing TK protein is dialyzed against several liters of 50 mM Tris, pH 7.5 10% sucrose, 2 mM DTT at 4° C. to remove thymidine.

3. Enzyme Kinetics

The kinetics of thymidine, ganciclovir and acyclovir phosphorylation by the wild-type, mutant 30 and 75 thymidine kinase enzymes with variant concentrations of radioactive nucleoside substrate are determined essentially as described in Example 3. $K_m$ and $V_{max}$ values are determined from double reciprocal plots and kcat values are calculated using the equation $V_{max}=k_{cat}[E_o]$ where $[E_o]$ is the total enzyme concentration. The BioRad reagent was used to determine the total enzyme concentration of purified thymidine kinase enzymes. Results are shown below in Table I.

TABLE V

Kinetic characterization of HSV-1 TK Mutants with thymidine, ACV and GCV as substrate

| | Substrate | | | | | | | | |
|---|---|---|---|---|---|---|---|---|---|
| | thymidine | | | ganciclovir | | | acyclovir | | |
| Enzyme | W.T. | 75 | 30 | W.T. | 75 | 30 | W.T. | 75 | 30 |
| $K_m$ (µM) | .380 | .950 | 13.3 | 47.6 | 10.0 | 333 | 417 | 23 | 455 |
| $k_{cat}$ (sec$^{-1}$) | .230 | .210 | .003 | .050 | .050 | .009 | .008 | .010 | .001 |
| $k_{cat}$ (sec$^{-1}$)/$K_m$ (µM) | .60 | .22 | 2E-4 | 1E-3 | 4.8E-3 | 2.7E-5 | 1.8E-5 | 4.5E-4 | 2.1E-6 |

*Calculations of $k_{cat}$ are per active site

Example 9

Production of Second Generation HSV-1 Thymidine Kinase Mutants Having Amino Acid Substitutions in Residues 159-161 and 168-169

This example describes the construction and analysis of a second generation of TK mutants, which are mutagenized at codons 159-161 and 168-169.

A. Isolation of Second Generation TK Mutants

As described above, mutants isolated from the LIF-ALL library show increased prodrug specificity compared to the wild-type TK (see also, Black et al., Proc. Nat'l Acad. USA 93:3525-3529, 1996). Using information from the ten most active mutants isolated from the LIF-ALL library, a new set of randomized oligonucleotides were synthesized and used to generate a second generation random library. Since the library was skewed to mutagenize codons encoding residues 159-161 and 169-170 to only represent a few amino acid substitutions, the library is considered to be semi-random.

FIG. 21 shows the semi-randomized oligonucleotides used to generate the library and the possible amino acid substitutions expected. These complimentary and partially overlapping oligonucleotides (DMO2211 and 2212) were purified after separation on a denaturing gel. After annealing of the respective 3' ends, the oligonucleotides were extended with DNA polymerase to form a 100 bp double-stranded DNA fragment. Following restriction with SacI and KpnI, the random fragments were ligated to pET23d:HSVTK-Dummy, which is described above and by Black et al., Proc. Nat'l Acad. USA 93:3525-3529, 1996). Vectors containing the mix of random sequences were used to transform a thymidine kinase-deficient E. coli, and the transformed E. coli were plated on growth medium which requires the presence of a functional plasmid-borne TK. A total of 120 clones were picked and restreaked onto selective medium to confirm the phenotype. Individual colonies were used to inoculate selective medium aliquoted in 96-well plates (one clone/well). Cultures were examined for their sensitivity to different levels of GCV or ACV. Lysates of all 120 mutants were assayed for the ability to phosphorylate thymidine, ACV and GCV, using methods described above.

Seven mutants that demonstrated required activities were selected for further study. Table VI shows the deduced amino acid sequence of these seven mutants (SR11, SR26, SR39, SR4, SR15, SR32, SR53).

TABLE VI

Amino Acid Substitutions at Residues 159-161 and 168-169 in Second Generation Semi-Random Mutants

| wild-type TK | LIFDRHPIAALL | |
|---|---|---|
| SR11 | -FL | FN |
| SR26 | -FA | F- |
| SR39 | IFL | FM |
| SR4 | ILL | YL |
| SR15 | -FA | YY |
| SR32 | -FV | VM |
| SR53 | IFV | FY |

B. Analysis of Second Generation TK Mutants

1. In Vitro Analysis of Second Generation Semi-Random Mutants in Cell Lines

The seven mutants were subcloned into the mammalian expression vector, pREP8D7:dualGFP. This vector contains a constitutive metallothionin promoter, which drives the expression of green fluorescent protein (GFP), and an RSV LTR promoter, which stimulated expression of the TK mutants. The vector also contains a histidinol resistance gene for selection of transformants. Purified vector DNA of these constructs was used to transfect BHK tk-cells by electroporation. The transfectants were selected by resistance to histidinol and sorted using FACS analysis for GFP expression. Pools of transfectants were then assayed for sensitivity to GCV or ACV over a range of prodrug doses. In both ACV and GCV assays, six of the seven mutants revealed lower $IC_{50}$ values than the wild-type TK transfectant pool. The remaining mutant transfectant pool (SR53) expressed low levels of TK protein which may account for its lower prodrug sensitivity. The results presented in Table VII show that mutants SR11, SR26, and SR39 are superior to wild-type TK or to mutant 75, using ACV as a substrate. Table VIII illustrates the $IC_{50}$ values from Rat C6 kill curves with the SR11, SR26, and SR39 mutants.

2. In Vivo Analysis of Second Generation Semi-Random Mutants in an In Vivo Mouse Xenograft Tumor Model Rat C6 glioblastoma cells were transfected with the stable expression vector pREP8D7:dualGFP as described above containing various TK mutants. Cells were transfected with either WT, SR39 or mutant 30 (LIF-ALL series) and sorted for comparable levels of GFP expression. Experiments were carried out to establish prodrug dosing levels for tumor ablation and efficacy of therapy. Nude mice (JAX Labs, Bar Harbor, Me.) were injected subcutaneously with $0.5 \times 10^6$ transfected rat C6 cells. After 5 days, prodrugs (ACV and GCV) were administered twice a day for a further 5 days. Prodrug was given at either of two concentrations (shown as mg/kg). During this period and for an additional 6 days, tumor size was monitored by caliper measurement every other day. At the end of the period, mice were sacrificed and the tumors excised and weighed.

Figure 32:
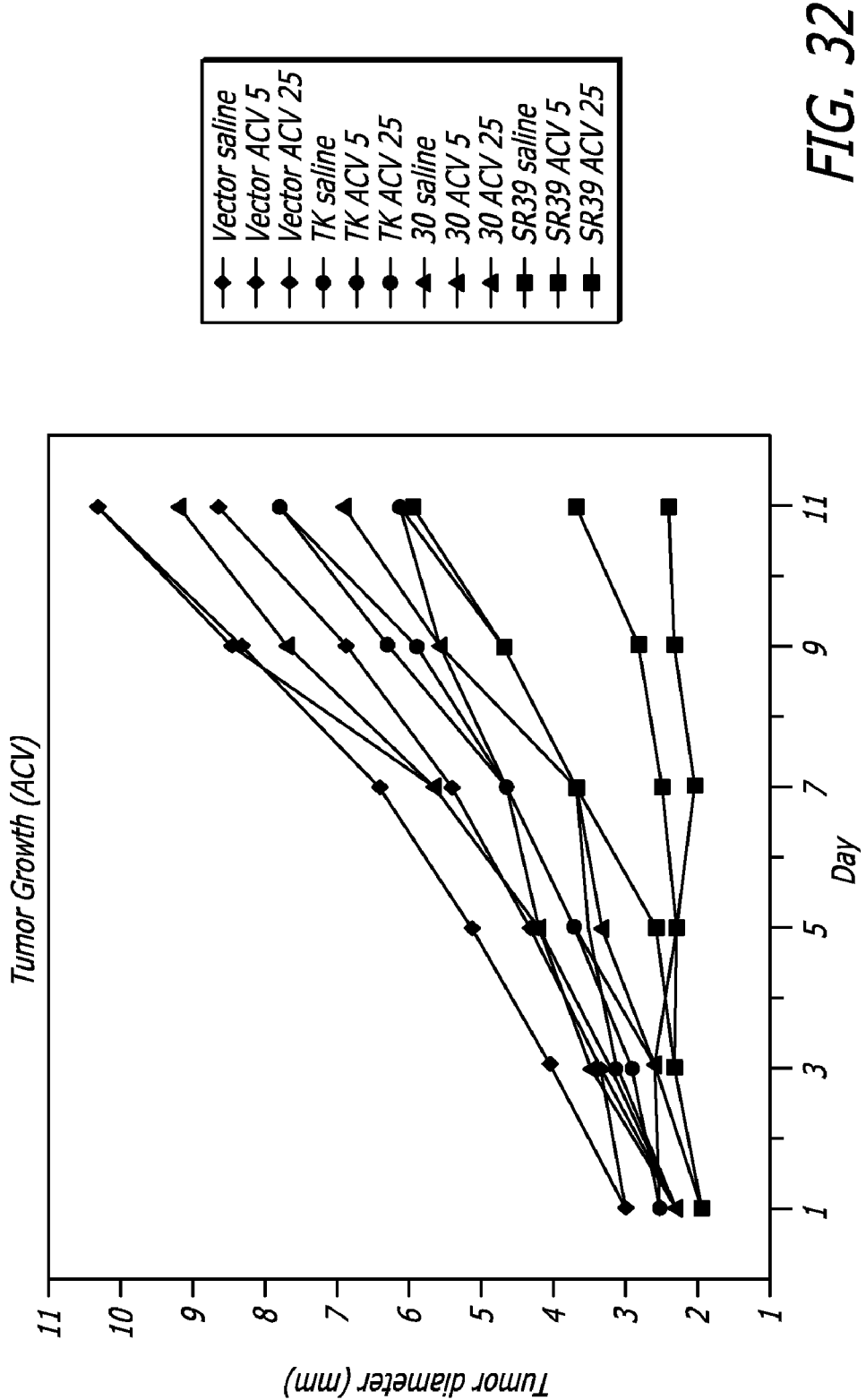
FIG. 32 is a graph which shows tumor growth after transfection by various vectors, and subsequent exposure to ACV.
Figure 33:
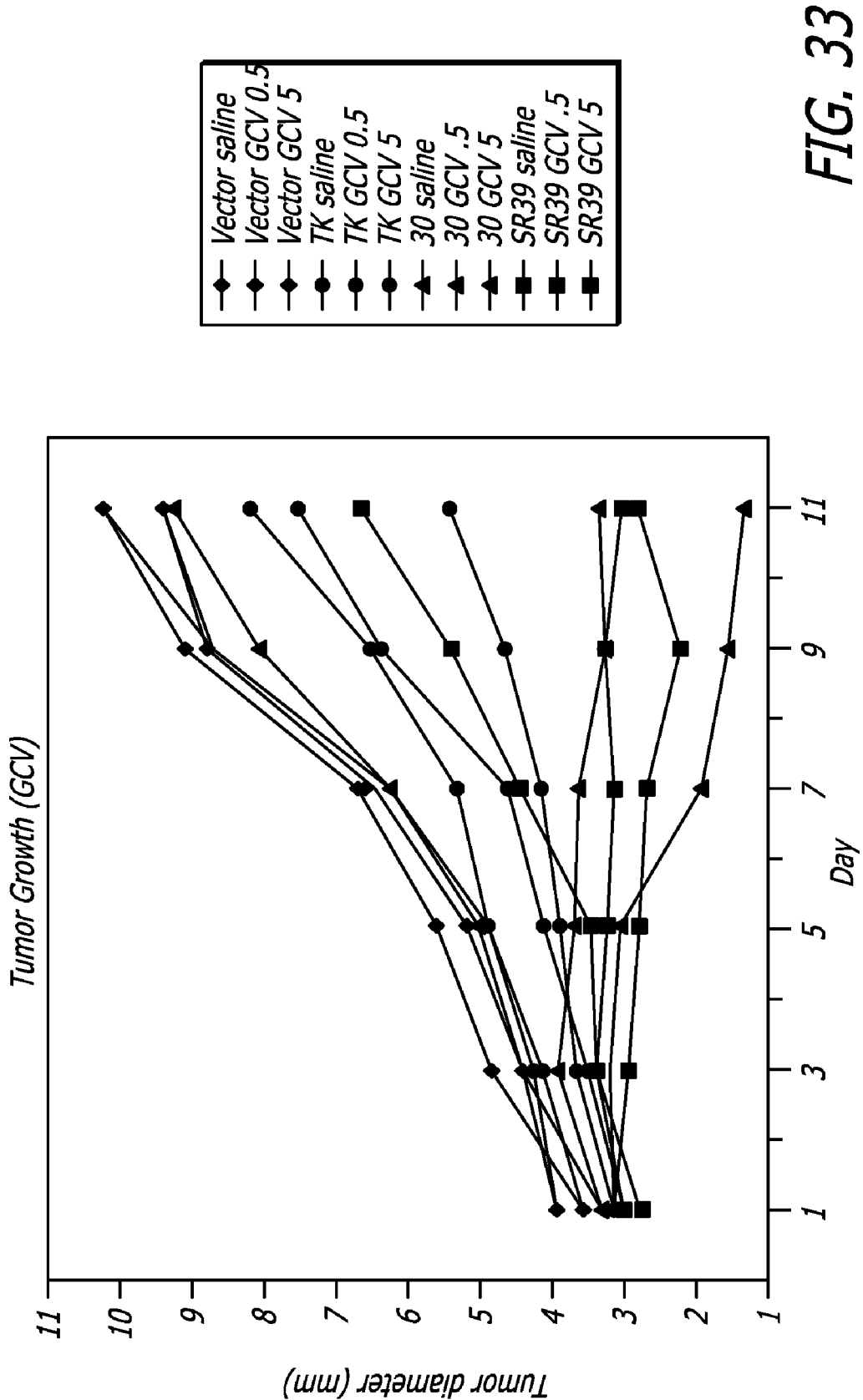
FIG. 33 is a graph which shows tumor growth after transfection by various vectors, and subsequent exposure to GCV.
Figure 34:
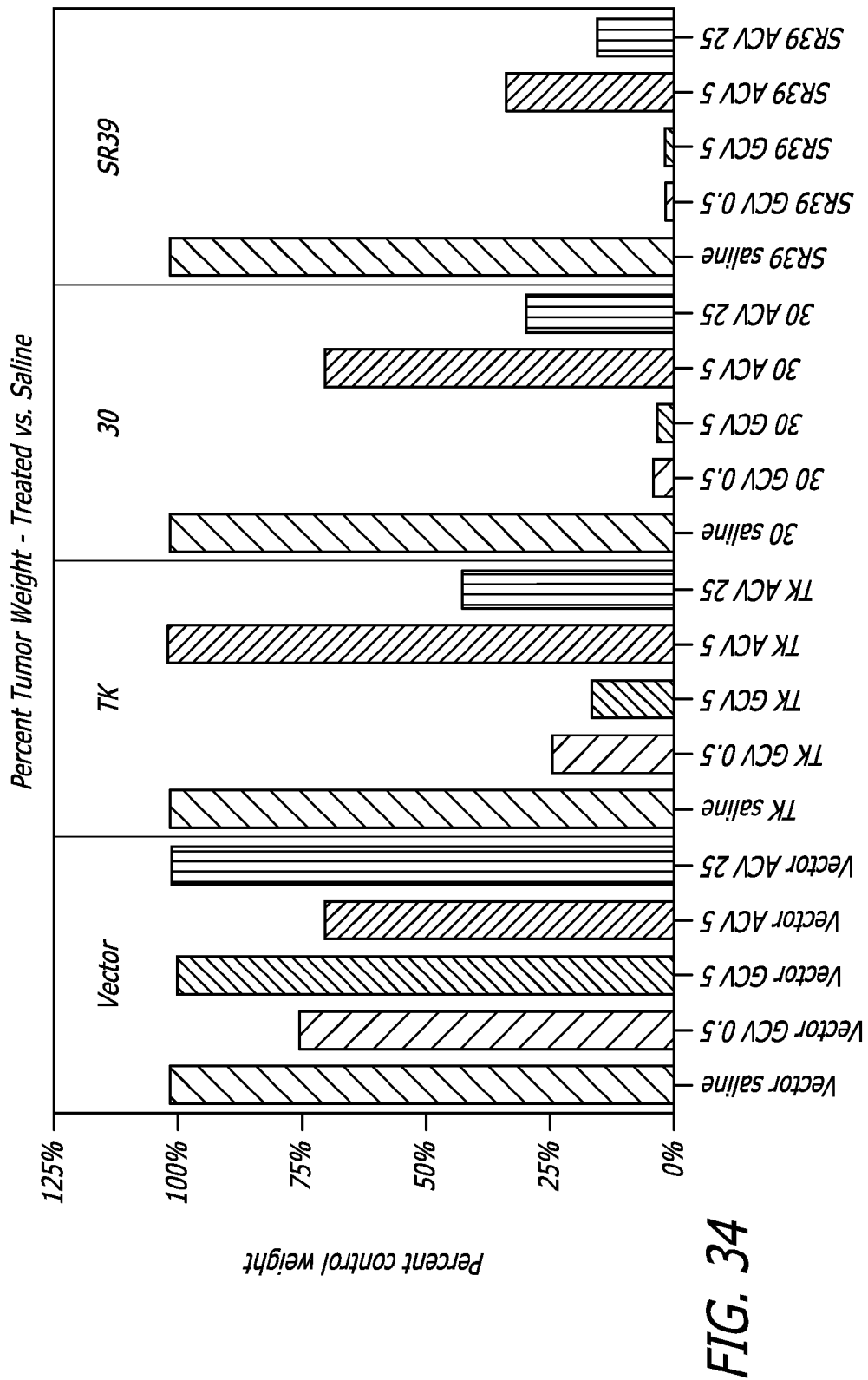
FIG. 34 is a bar graph which shows the percentage change of tumor weight for various treatments.

Data is presented in FIGS. 32, 33 (tumor diameter) and 34 (final tumor weight) and demonstrates that SR39 (as well as mutant 30) is a highly effective mutant and can cause significant tumor reduction using either ACV or GCV. The degree of in vivo tumor inhibition using both mutant 30 and SR39 are clearly superior to that of the wild-type enzyme. Further, data with SR39 and ACV suggest for the first time that ACV can function as an effective prodrug for suicide gene therapy.

TABLE VII

IC50 Values for ACV Kill Curves

| Enzyme | ACV (μM) |
|---|---|
| TK | 0.2 |
| 75 | 0.06 |
| SR11 | 0.025 |
| SR26 | 0.035 |
| SR39 | 0.03 |

TABLE VIII $IC_{50}$ Values from Rat C6 Kill Curves

| | $IC_{50}$(μM) | | | |
|---|---|---|---|---|
| | GCV | relative to TK | ACV | relative to TK |
| TK | 5 | 1 | >20 | 1 |
| 30 | 0.01 | 500 | 0.26 | >77 |
| 75 | >1 | <5 | >20 | — |
| 411 | 0.1 | 50 | 14 | >1.4 |
| SR11 | 0.15 | 33 | 6 | >3 |
| SR26 | 0.04 | 125 | 0.76 | >26 |
| SR39 | 0.107 | 294 | 0.11 | >182 |

Enzyme kinetic analyses of purified SR11, SR26, and SR39 proteins were performed as described above. The results of these studies are summarized in Table IX.

TABLE IX

Kinetics of Semi-Random Library Mutants

| | Km(μM) | | |
|---|---|---|---|
| | Thymidine | GCV | ACV |
| TK | 0.4 | 47 | 319 |
| SR11 | 1.0 | 6.4 | 5.6 |
| SR26 | 1.4 | 17.6 | 3.4 |
| SR39 | 6.7 | 3.3 | 9.8 |

Example 10

Mutagenesis of a Region within the Q Substrate Binding Domain of HSV-1 Thymidine Kinase This example describes the construction and analysis of TK mutants that have been mutagenized in a region of the recently identified Q substrate binding domain.

A. Isolation of TK Mutants Having Modifications in the Q Substrate Binding Domain To construct a dummy vector for insertion of the random sequences, a NarI (or KasI) site was introduced into pET23d:HSVTKII by site-directed mutagenesis, using primer DM01358 (5'-GTCTCGGAGGCGCCCAGCACC-3') within the wild-type thymidine kinase open reading frame at nucleotide position 276 from the ATG. The pET23d:HSVTKII vector is described by Black et al., Proc. Nat'l Acad. Sci. USA 93:3525-3529, 1996. Restriction of pET23d:HSVTK-Nar, which is the pET23d:HSVTKII vector with an engineered NarI site, by SacI and NarI allowed removal of TK sequences and replacement by a 1 kb NarI/SacI fragment from the vector, pLXSN. This vector was designated pET23d:HSVTK-Nar Dummy.

For the first random library, two oligonucleotides were synthesized containing the three non-wild-type nucleotides at a frequency of 9% (i.e., the wild-type nucleotides were represented at 91% frequency) for the codons corresponding to residues 112-132. FIG. 22 shows the sequences of oligonucleotides DMO-1860 and -1861, which are complementary and overlap. These oligonucleotides represent wild-type sequences. Random mutations were introduced by including non-wild-type nucleotides at a frequency of 9% for synthesis of regions presented in boldface type of DMO-1860 and -1861 oligonucleotides (i.e., after the discontinuity indicated in each sequence). FIG. 22 also outlines how the oligonucleotides were used in a PCR amplification to generate the correct-sized fragment. Briefly, an initial set of polymerase chain reactions (20 rounds) was performed to combine the four internal oligonucleotides (DMO-1860, DMO-1861, DMO-1893, and DMO-1894) into full-length product. A second PCR set (10 rounds) used the two smaller oligonucleotides, designated DMO-1895 and DMO-1896, to amplify the product and to add overhanging sequences for restriction cleavage. The product of this reaction was cleaved with KasI and SacI and ligated into the pET23d:HSVTK-Nar Dummy (KasI/SacI) vector. Following electroporation into BL21 (DE3) tdk- E. coli, the cells were plated onto TK selection plates and scored for growth. All colonies were retested on fresh TK selection plates. Several hundred clones were sequenced and found to contain zero to six amino acid substitutions spanning the 20 amino acid region.

Two subsequent libraries were constructed using only one of the mutagenic oligonucleotides to increase the frequency of single amino acid changes. Several hundred TK positive clones were sequenced. Lysates from these mutants have been assayed for the ability to phosphorylate thymidine, acyclovir and ganciclovir, demonstrating that mutation within the Q substrate binding domain alters substrate specificity.

Example 11

Isolation of Human and Mouse Guanylate Kinases and Construction of HSV-1 Thymidine Kinase and Guanylate Kinase Dual Expression Vectors This example describes the isolation of the human and mouse guanylate kinase genes and the vector construction for dual expression of herpes thymidine kinase and guanylate kinase.

A. Isolation of the Human Guanylate Kinase Gene

1. Isolation of the Human Guanylate Kinase Gene

Two oligonucleotides are designed to amplify the entire human guanylate kinase open reading frame. The following two oligonucleotides are synthesized by GenSet (La Jolla, Calif.): 5'-ACTACTGGAT[CCATGG]CGGGCCCCAGGC-CTGTG-3', a 33-mer (SEQUENCE ID. NO. 26) and 5'-TAC-TACGGATCCTCAGGCGGCGGTCCTTTGAGC-3', a 33-mer (SEQUENCE ID. NO. 27). The BamHI sites at each end are underlined and the NcoI site at the initiating methionine codon is shown in brackets. The bold nucleotide denotes a nucleotide alteration from the original sequence (GenBank accession number A11042). The human guanylate kinase gene is amplified from a cDNA library of human proliferating B lymphocytes stimulated with alpha-CD3. The resulting single band (~600 bp) is restricted with BamHI and cloned into pUC118 (BamHI) to yield pUC118:Hugmk. The insert is sequenced in entirety (both strands) using the following set of oligonucleotides: 5'-CTGCTGAAGAGGCTGCTC-3' (18mer) (DMO 512) (SEQUENCE ID. NO. 28), 5'-ACACA-GATGCGGTTTCATG-3' (19mer) (DMO 513) (SEQUENCE ID. NO. 29), 5'-CTGGACGTGGACCTGCAG-3' (18mer) (DMO 514) (SEQUENCE ID. NO. 30), 5'-GTTAAT-GATGACCACATC-3' (18mer) (DMO 515) (SEQUENCE ID. NO. 31), 5'-TGTAAAACGACGGCCAGT-3' (18mer) (M13 forward primer purchased from ABI) (SEQUENCE ID. NO. 32) and 5'-CAGGAAACAGCTATGACC-3' (18mer) (M13 reverse primer from ABI) (SEQUENCE ID. NO. 33). Sequence analysis revealed identity with the GenBank sequence except for the anticipated alteration at the NcoI site which results in a serine to alanine change (S2A) (FIG. 24).

2. Northern Blot

8 µg of total RNA from SP2/0 murine B lymphoma cells is prepared in 1×MOPS buffer/75% formamide and heat denatured for 10 min at 55° C. and loaded on a 1.2% agarose gel in 1×MOPS buffer. After transfer to nitrocellulose the blot is probed with the human gmk gene.

The 600 bp BamHI fragment is gel isolated from pUC118: Hugmk and is labeled using the random primer labeling kit from Amersham according to the manufacturer's instructions. The free radiolabel is removed by size exclusion chromatography. Following hybridization and washes the blot is exposed to X-ray film at −70° C. for two days. Autoradiography of the northern blot reveals a single ~750 nt RNA species. In a similar experiment using human poly A+ RNA from proliferating B lymphocytes, a single ~750 nt band is also observed.

B. Isolation of Mouse Guanylate Kinase Gene

1. Screening a Mouse cDNA Library

A lambda gt10 cDNA library of mouse 702/3 cells (B lymphomas) is probed using the human gene (same probe as used for northern blot analysis). The total number of plaques screened is 2×10$^5$ pfu. Nine independent lambda clones hybridized to the human probe and are plaque purified.

2. Subcloning and Sequence Analysis of Positive Clones

The EcoRI fragments from eight phage DNA preparations are gel isolated and subcloned into pUC118 restricted with EcoRI and dephosphorylated. The DNA insert sizes ranged from ~300 bp to 1.2 kb. Preliminary sequence analysis with primer (M13 forward primer) reveals that all clones began approximately 60 bp 5' to the putative ATG start codon as determined by sequence alignment with the human and bovine guanylate kinase sequences and varied at their respective 3' ends. One representative clone (both strands) is completely sequenced using the following oligonucleotides: 5'-TGTGTCCCATACTACTACAAG-3' (21mer) (DMO 592) (SEQUENCE ID. NO. 34), 5'-TGAGAACTCAGCAGCAT-GCTC-3' (21mer) (DMO 594) (SEQUENCE ID. NO. 35), 5'-GTGCTAGATGTCGACCTA-3' (18mer) (DMO 595) (SEQUENCE ID. NO. 36), 5'-ACCTGGATAAAGCCTATG-3' (18mer) (DMO 674) (SEQUENCE ID. NO. 37), 5'-AAG-CAGGCGCTCTCTCTGA-3' (19mer) (DMO 675) (SEQUENCE ID. NO. 38), 5'-CTATTTCTCATATGATGT-3' (18mer) (DMO 731) (SEQUENCE ID. NO. 39) and 5'-GT-TACAGTGTCTCTAGAG-3' (18mer) (DMO 732) (SEQUENCE ID. NO. 40), 5'-TCCCCCACCTCCAGGC-3' (16mer) (DMO 748) (SEQUENCE ID. NO. 52), 5'-CT-CAGTGTTGCCCAGTCG-3' (18mer) (DMO 749) SEQUENCE ID. NO. 53) and 5'-GCCGAAGATGCTGCT-GTG-3' (18mer) (DMO 750) SEQUENCE ID. NO. 54). The final murine guanylate kinase gene sequence is shown in FIG. 25 with the deduced amino acids.

3. Introduction of a New Restriction Site

A novel NcoI restriction site is introduced at the start codon of the mouse guanylate kinase open reading frame as described in Black, M. E. and Hruby, D. E. (*J. Biol. Chem.* 265:17584-17592, 1990). The mutagenic oligonucleotide used is: 5'-CTAGGTCCTG[CCATGG]CGTCCGCG-3' (24mer) (DMO 676) (SEQUENCE ID. NO. 41) with the NcoI site shown in brackets and the bold nucleotide denoting a C to G change. The resulting clone, pUC118:Mugmk-NcoI, is sequenced to confirm orientation and the 5' junction region.

C. Construction of Vectors for in Vitro Transcription and Translation Analysis

Both the human and murine guanylate kinase genes are subcloned into pET23d (see Example 8). The 600 bp NcoI/BamHI fragment from pUC118:Hugmk is gel isolated and directionally subcloned into pET23d (see Example 8) restricted with NcoI and BamHI. The murine guanylate kinase gene is gel isolated as a ~800 bp NcoI/EcoRI fragment using the introduced NcoI site at the ATG and the EcoRI site from the pUC118 3' polylinker region, and cloned into pET23d (see Example 8) restricted with NcoI and EcoRI. The resulting plasmids, pET23d:Hgmk and pET23d:Mgmk, are then used as templates for in vitro transcription and, the mRNAs produced, are used in a rabbit reticulocyte lysate cell free translation system as described in Examples 3 and 8. Enzyme assays to confirm full-length protein production and activity are as described in Agarwal et al. (*Methods in Enzymol.* 51:483-490, 1978) with bovine guanylate kinase purchased from Sigma as a positive control.

D. Purification and Characterization of the Human and Mouse Civanylate Kinases

1. Expression Vector Construction

The pET23d vector (Novagen, Madison, Wis.) is used as the vector backbone for the construction of pET:HT. This vector contains a 6 histidine residue peptide followed by a thrombin cleavage site to allow for the expression of a removable histidine tag fused to the N terminus of the target gene product. Synthesis of the 6 his-thrombin fusion encoding region is done by PCR amplification of the promoter region of pET23d and extension using the following primers in three sequential PCR amplification steps. 5'-ACTACTACTA GATCTCGATC CCGCGAA-3' (27mer) (DMO 604) (SEQUENCE ID. NO. 42) 5'-ATGATGATGA TGATGGCTGC TAGCCATAGT ATATCTCCTT C-3' (41mer) (DMO 605) (SEQUENCE ID. NO. 43) 5'-CGGCACCAGG CCGCTGCTGT GATGATGATG ATGATGGCT-3' (39mer) (DMO 606) (SEQUENCE ID. NO. 44), 5-AGTAGTAT[CC ATGG] AGCTGC CGCGCGGCAC CAGGCCGCTG CT-3' (42mer) (DMO 607) (SEQUENCE ID. NO. 45). Sequence DMO 604 is annealed to the BglII region of pET23d in all PCR amplification steps. Sequence DMO 605 is annealed to the region corresponding to the NcoI site in a 3' to 5' orientation and results in the loss of the NcoI site due to a nucleotide mutation shown in bold in the sequence above. Subsequent amplifications with sequence DMO 606 or DMO 607 in the 3' to 5' orientation are paired with sequence DMO 604 to extend the sequence for the addition of 6 histidine codons and a thrombin cleavage site. A new NcoI site is also introduced with sequence DMO 607 as shown in brackets above. The final BglII/NcoI fragment is cloned into pET23d at the corresponding sites to create pET:HT. pET:HT is sequenced to confirm correct synthesis and insertion. The amino acid sequence of the new vector fusion peptide is: M A S S H H H H H H H S S G LVPRGS S M (NcoI site) (SEQUENCE ID. NO. 46) with the thrombin cleavage recognition site underlined. Cleavage with thrombin is between the arginine and glycine residues.

2. Overexpression in *E. coli* and Affinity Purification

Methods for overexpression and analysis are as in Example 8. Affinity purification using His-Bind Resin (Novagen, Madison Wis.) is performed according to the manufacturer's instruction. Thrombin is used to cleave off the terminal 17 amino acids to leave three amino acids N-terminal to the guanylate kinase initiating methionine. The leader peptide is then removed by passing the cleavage mix over the His-Bind column a second time.

3. Enzyme Kinetics

The $K_m$, $V_{max}$ and $K_{cat}$ values for guanylate, GCV-monophosphate and acyclovir-monophosphate are determined using purified human and mouse guanylate kinases. In addition to using the assay protocol described in Agarwal et al. (*Methods in Enzymol.* 51:483-490, 1978), the nucleotide products generated from assays performed with, radionucleotide substrates are analyzed by thin layer chromatography and scintillation counting.

E. Expression of Human and Murine Guanylate Kinases in Mammalian Cells

1. Vector Construction

Both human and murine guanylate kinase genes are cloned into a modified pREP8 vector. Briefly, for construction of the modified pREP8 (pREP8-7 kb), pREP8 (Invitrogen) is digested with BstEII and XbaI, filled in with Klenow and religated. The resulting plasmid, pREP8-7 kb, no longer encodes EBNA-1 or the EBV origin of replication (oriP). Both guanylate kinases, pET23d:hgmk and pET23d:mgmk (described above) are restricted with NcoI, blunt-ended and then digested with BamHI to yield a ~600 bp NcoI (blunt)-BamHI fragment after gel purification. These are ligated to pREP8-7 kb that has been digested with HinDIII (blunt-ended) and BamHI. The new plasmids are designated pREP8-7:hgmk and pREP8-7:mgmk.

2. Isolation of Stable Transfectants Expressing HSVTK

BHKtk-(ts13) cells are transfected with pCMV, pCMV: TK, pCMV:30 and pCMV:75 DNA in the presence of pSV2-neo (10:1 ratio) as described in Example 8. Approximately 10-20 individual clones from each pCMV DNA transfection are isolated under 1 mg/ml G418 selection. As in example 8, about $2 \times 10^6$ cells per clone are examined for TK expression level by western blot using polyclonal anti-TK serum.

Expression of TK clone C3 is very high, whereas 75 D4 and 30 A2 are less than half the TK expression level of C3. 75 D2, D3 and D4 protein expression ranged from very low, low to moderate, respectively.

3. Sensitivity of Clones to GCV or ACV

Figure 26:
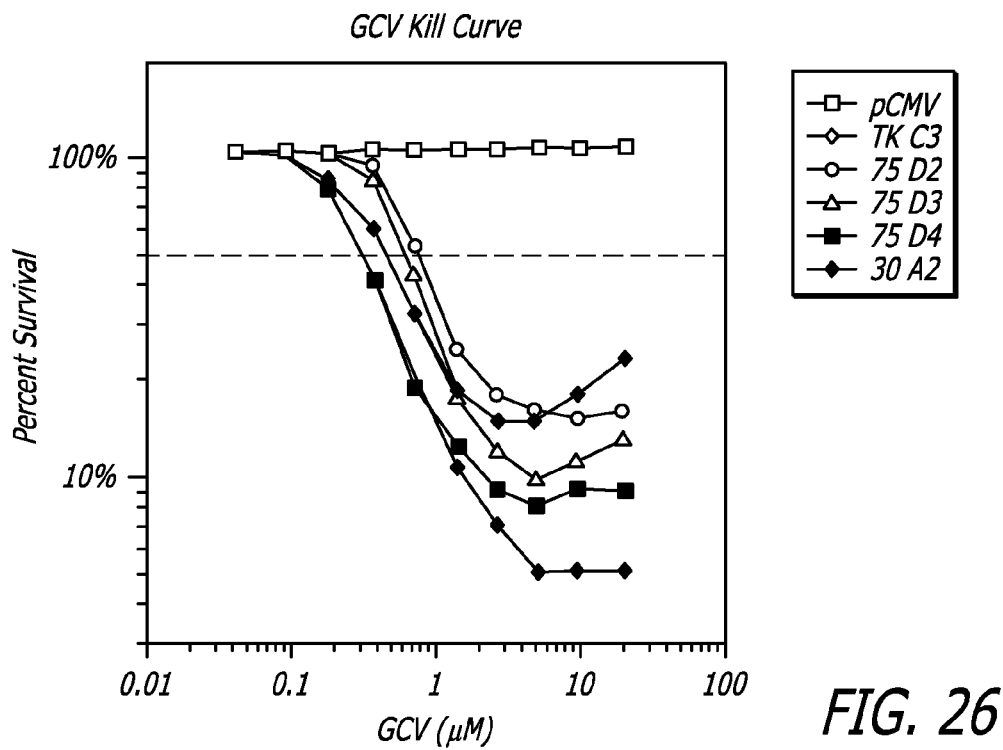
FIG. 26 is a graph which shows the sensitivity of TK clones to GCV.
Figure 27:
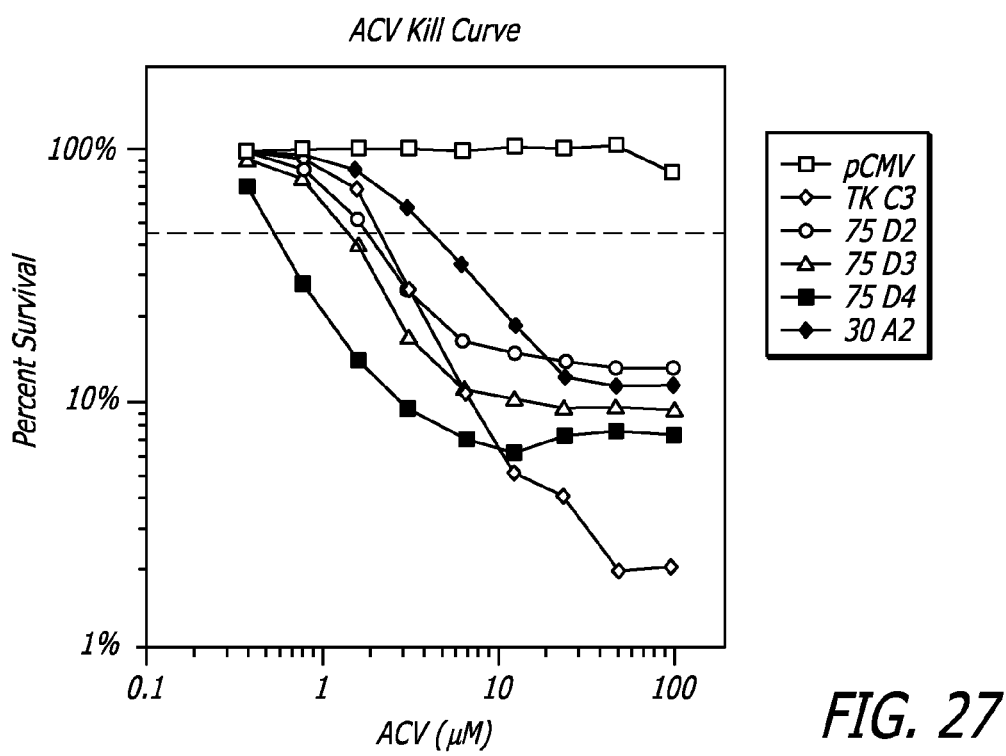
FIG. 27 is a graph which shows the sensitivity of TK clones to ACV.

Clones are assayed for sensitivity to GCV and ACV as described in Example 8. Sensitivity to GCV and ACV is dependent on the level of protein expression. This can clearly be seen with the 75 clones, D2, D3 and D4 where the highest expression clone D4 is the most sensitive, D3 is less so and D2 is even less sensitive than D3 to prodrugs. (FIGS. 26, 27)

4. Transfection of TK-Expressing Cells with pREP8-7 Guanylate Kinase Constructs pREP8-7, pREP8-7:hgmk and pREP8-7:mgmk are used to transfect BHK tk, TK-transfected clone C3 and 75-transfected clone D4. Histidinol is used to select pools of stable transfectants and to isolate individual clones.

Protein expression levels of guanylate kinase in the different pools is determined by immunoblot analysis. Briefly, 5 μl of $2 \times 10^6$ cell pellet lysates (200 μl) are subjected to electrophoresis and transferred to nitrocellulose. Polyclonal anti-guanylate kinase serum (at a 1:5,000 dilution) and TK anti-serum (at a 1:10,000 dilution) is utilized to detect the resultant protein bands.

5. Sensitivity of Guanylate Kinase Transfectant Pools to GCV and ACV in TK Expressing Clones As in Example 8, pools of transfectants are placed in 96 well microtiter dishes at 1000 cells/well. Eight replicates are incubated for three days in the presence of various GCV or ACV concentrations.

Figure 28:
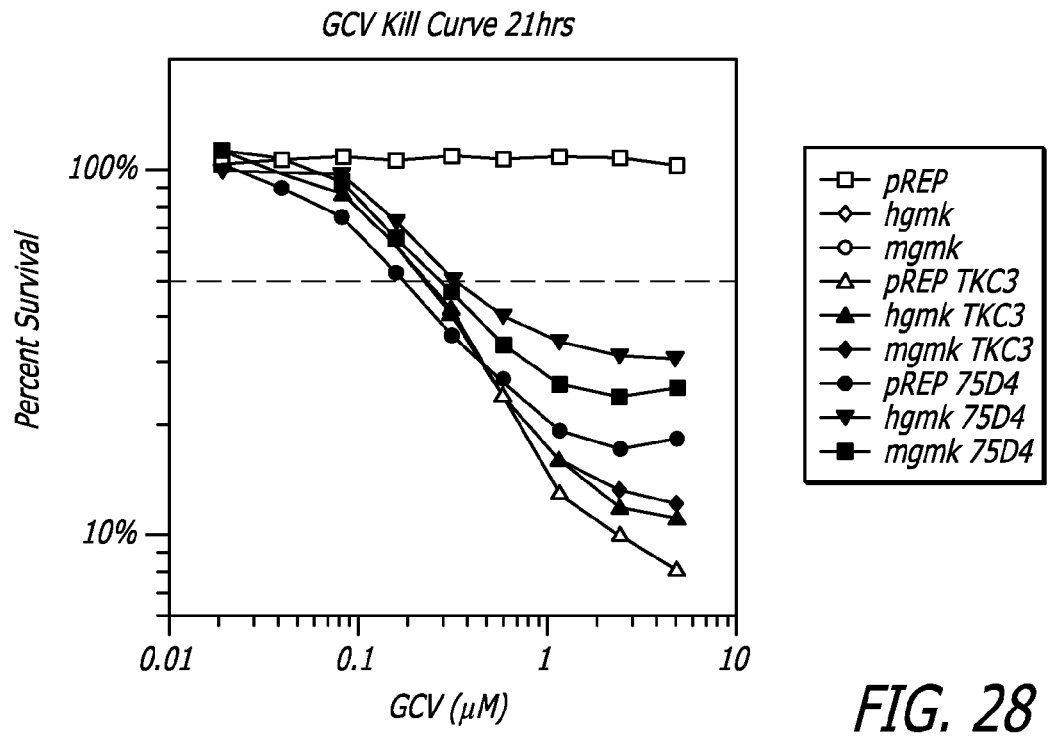
FIG. 28 is a graph which shows the sensitivity of guanylate kinase transfectant pools to GCV in TK expressing clones.
Figure 29:
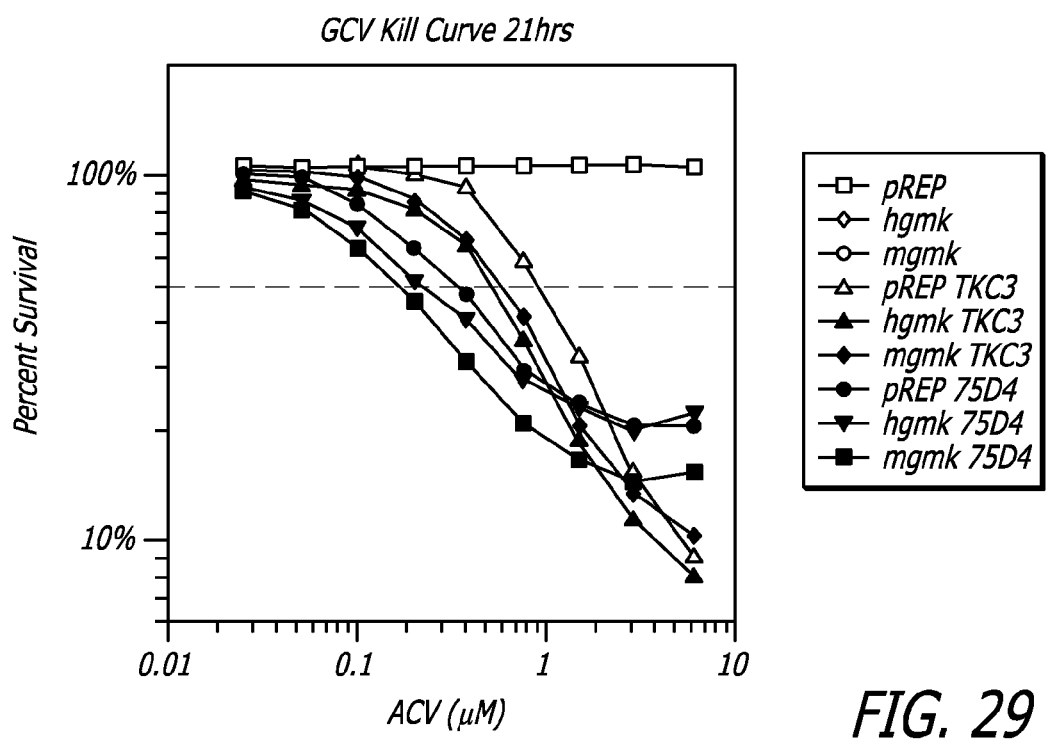
FIG. 29 is a graph which shows the sensitivity of guanylate kinase transfectant pools to ACV in TK expressing clones.

As can be seen in FIGS. 28 and 29, the level of prodrug sensitivity is related to the level of TK protein expression and the presence of guanylate kinase. Guanylate kinase expression in the presence of wild-type TK demonstrates approximately 2 fold increased sensitivity to ACV relative to TK expression alone. Despite half the expression level of wild-type TK, sensitivity to ACV by gmk+75 D4 expressing cells is 6-7 times greater than that of TK expressing cells.

F. Construction and Analysis of Dual Expression Vectors in Vivo

The HSV1 tk gene is cloned into the HpaI site of pLXSN (Miller and Rosman, *BioTechniques* 7:980-990, 1989) as a NcoI (blunt-ended) fragment and the orientation determined by restriction mapping. This places the HSV-1 tk gene behind the MoMLV LTR promoter. The neomycin phosphotransferase gene is replaced by the guanylate kinase gene (human or mouse) as a BamHI (blunt-ended) fragment such that guanylate kinase gene expression is driven off the SV40 promoter. In addition, vectors are constructed where the tk and gmk gene order is reversed such that the tk gene is expressed from the SV promoter and gmk is expressed from the LTR promoter. Vector constructs with individual genes (tk or gmk) are also constructed. Furthermore, expression vectors containing HSV-1 tk mutants in place of the wild-type HSV-1 tk genes are also constructed.

As in Example 8, plasmid DNA from the constructs described above are used to transfect ts13 BHK tk-cells, SF767 human glioblastoma cells, and rat C6 glioblastoma cells in the presence of a marker plasmid (pSV2-neo) to enable the selection of transfectants on G418.

Selection of stable transfectants and assays for increased sensitivity to ACV and GCV are as described in Example 8.

Example 12

Construction and Analysis of Guanylate Kinase Thymidine Kinase Fusion Proteins This example illustrates the production and analysis of several fusion proteins that have both guanylate kinase and thymidine kinase activities.

A. Construction of Fusion Proteins

Use of a fusion protein for gene therapy would not only negate the requirement for two promoters and the associated reduction in prodrug activation due to the differences in promoter strength, it would also allow expression of two enzyme functions from a single promoter and a single cistron. Accordingly, fusion proteins are advantageous for gene therapy vectors which cannot tolerate large pieces of foreign DNA, such as AAV vectors.

Figure 30:
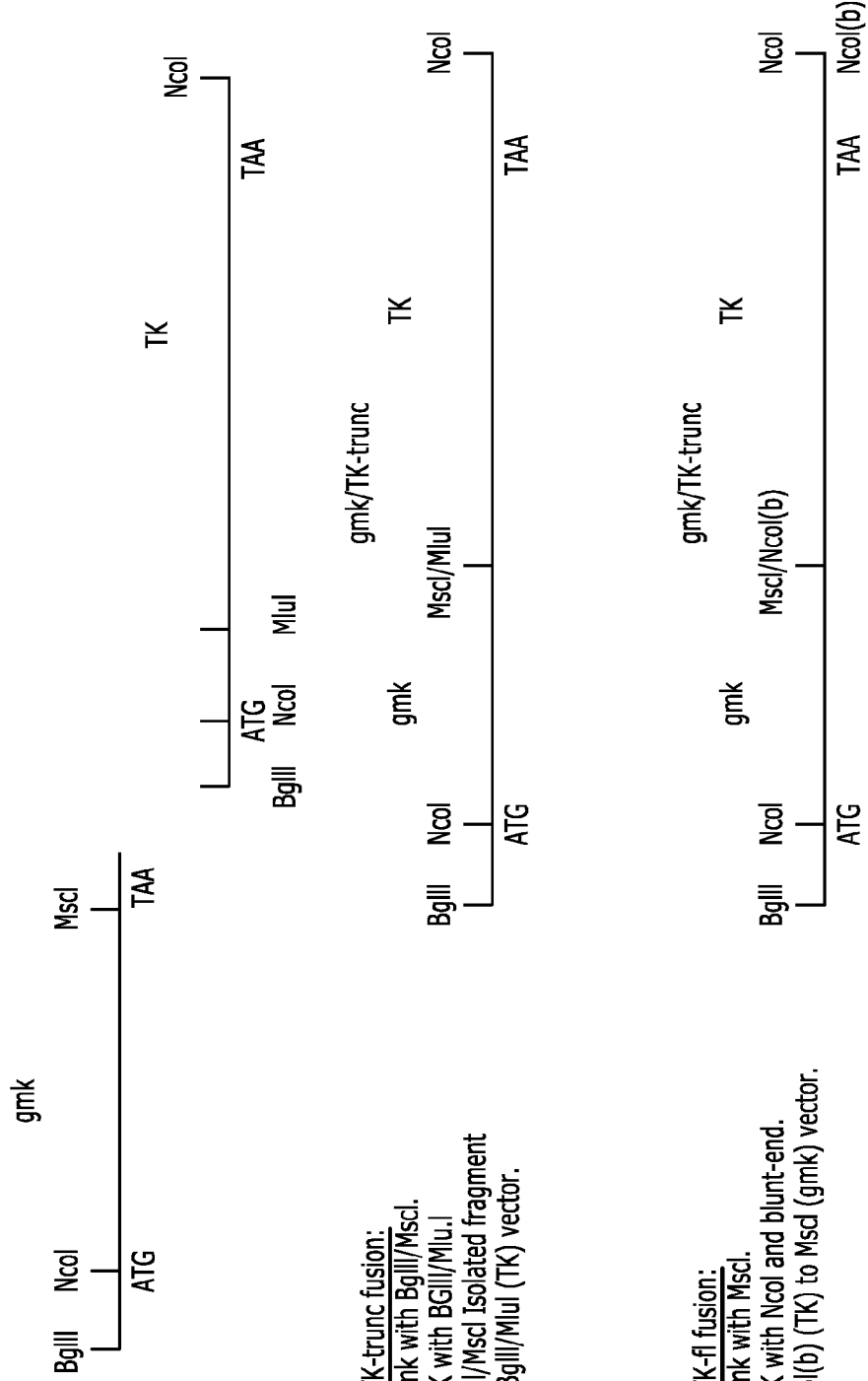
FIG. 30 is an illustration of gmk/TK fusion protein constructs.

Two fusion proteins have been constructed that contain both wild-type HSV-1 TK and murine guanylate kinase (gmk) sequences. These proteins differ in the number of residues at the fusion site. Both fusion constructs can be over-expressed in E. coli from pET23d backbone vectors. In both vectors, guanylate kinase was located adjacent to the promoter with TK fused to the MscI site at the 3' end of gmk which removes the two C-terminal amino acids. One fusion was constructed such that the first nine amino acids of TK are absent (pET23d:gmlc/TK-trunc). The other fusion contains the entire TK amino acid sequence (pET23d:grnk/TK-fl). Maps of these constructs are illustrated in FIG. 30.

Six additional fusion proteins have been constructed in which the wild-type TK sequence of pET23d:gmk/TK-fl is replaced by TK mutant 30, mutant 75, mutant 411, SR11, SR26 or SR39 sequences. These fusion proteins were over-expressed in BL21 (DE3) tk-cells.

B. Analysis of Fusion Proteins

Figure 31:
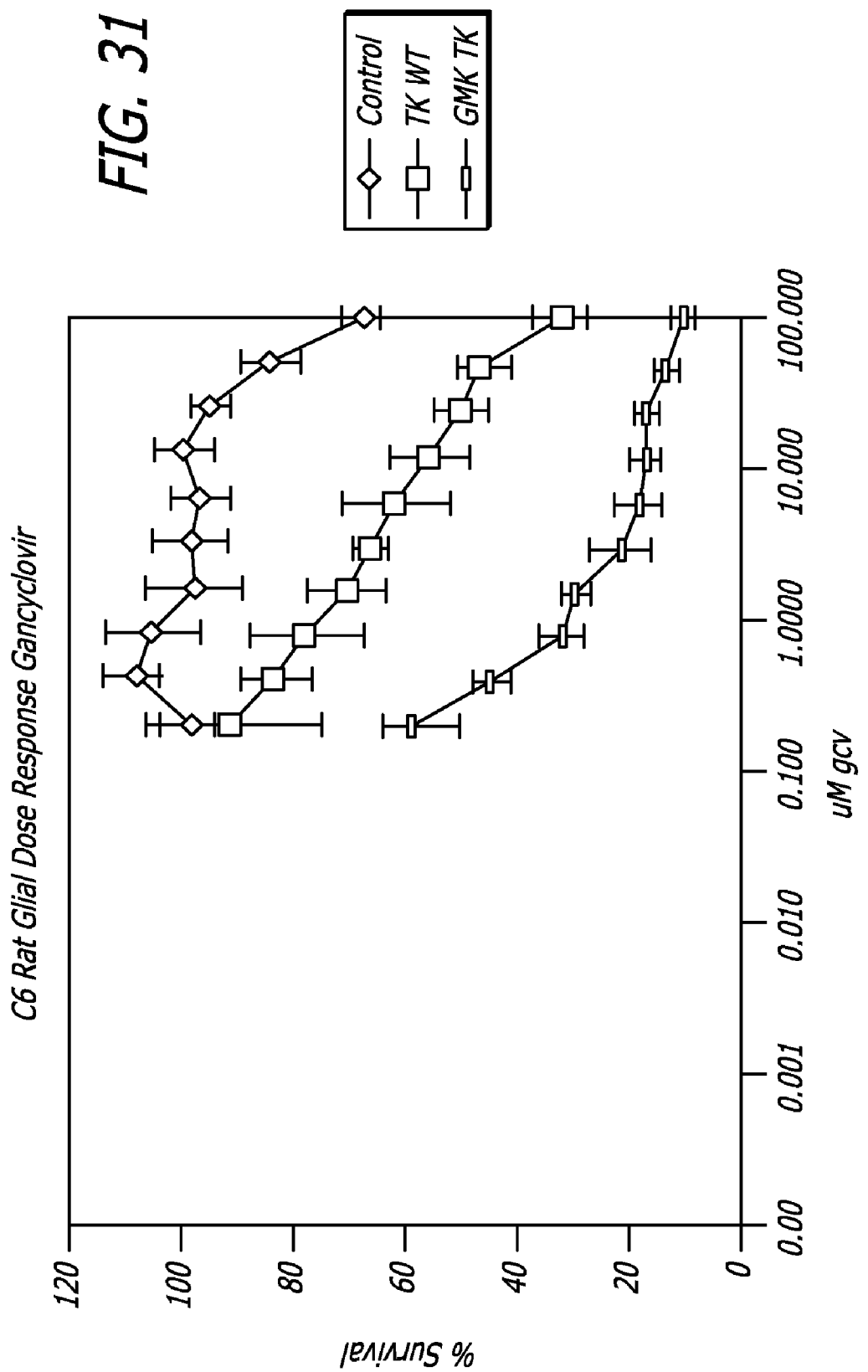
FIG. 31 is a graph which shows a ganciclovir dose response curve, comparing wild-type TK with a gmk/TK fusion protein.

All of the above constructs were cloned into pREP8D7:dualGFP, as described above. These vectors were used to transfect BHK tk-cells and transfectants were selected on the basis of resistance to histidinol. Further screening for GFP expression was performed by FACS analysis. In addition, the gmk/TK-fl construct was used to transfect rat C6 glioma cells and positive clones/pools were selected as described above. A ganciclovir dose response curve comparing gmk/TK-trunc to wild-type TK in rat C6 cells is shown in FIG. 31. This curve demonstrates a 100-fold difference in $IC_{50}$ between the two enzymes with the fusion protein being the superior one.

Both wild-type TK-gmk fusion proteins were over-expressed in E. coli and purified to homogeneity using affinity chromatography. Michaelis-Menten kinetics for both thymidine kinase and guanylate kinase activities were examined with both fusion proteins, and the results are shown in Table X. The thymidine kinase activity is similar to wild-type levels. However, gmk function is impaired 3.8 to 5.8 fold in the fusion protein constructs compared to wild-type gmk. Nevertheless, the fusion proteins exhibited both guanylate kinase and TK activities.

TABLE X

Kinetic Analysis of Fusion Proteins

| | Km (µM) | | | |
|---|---|---|---|---|
| | gmk | gmk/TK-trunk | gmk/TK-fl | TK |
| GMP | 25 | 95 | 146 | — |
| dGMP | — | 218 | 359 | — |
| thymidine | — | 0.67 | 0.5 | 0.3 |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. An isolated fusion protein comprising a guanylate kinase moiety comprising SEQ ID NO. 49 and a thymidine kinase moiety, wherein said fusion protein possesses a biological activity of said guanylate kinase and a biological activity of said thymidine kinase, wherein said thymidine kinase moiety is either a Herpesviridae thymidine kinase of SEQ ID. NO. 134 or a mutant Herpesviridae thymidine kinase of SEQ ID. NO. 134 with an amino acid substitution at one or more of positions 160, 161 or 168 that possesses increased biological activity, when compared to the Herpesviridae thymidine kinase of SEQ ID. NO. 134.

2. The isolated fusion protein according to claim 1, wherein at least one of said guanylate kinase moiety and said thymidine kinase moiety is truncated.

3. The isolated fusion protein according to claim 1, wherein said mutant thymidine kinase comprises amino acid substitutions at positions 160, 161 and 168.

4. The isolated fusion protein according to claim 3, wherein said mutant thymidine kinase further comprises an amino acid substitution at position 169.

5. The isolated fusion protein according to claim 4, wherein said mutant thymidine kinase further comprises an amino acid substitution at position 159.

6. The isolated fusion protein according to claim 3, wherein said amino acid substitution at position 160 is isoleucine to phenylalanine, said amino acid substitution at position 161 is phenylalanine to leucine or alanine and/or said amino acid substitution at position 168 is alanine to phenylalanine.

7. The isolated fusion protein according to claim 4 wherein said amino acid substitution at position 169 is leucine to asparagine or methionine.

8. The isolated fusion protein according to claim 5 wherein said amino acid substitution at position 159 is leucine to isoleucine.

9. The isolated fusion protein according to claim 6 wherein said amino acid substitution at position 160 is isoleucine to phenylalanine, said amino acid substitution at position 161 is phenylalanine to alanine and said amino acid substitution at position 168 is alanine to phenylalanine.

10. The isolated fusion protein according to claim 4 wherein said amino acid substitution at position 160 is isoleucine to phenylalanine, said amino acid substitution at position 161 is phenylalanine to leucine, said amino acid substitution at position 168 is alanine to phenylalanine and said amino acid substitution at position 169 is leucine to asparagine.

11. The isolated fusion protein according to claim 5 wherein said amino acid substitution at position 160 is isoleucine to phenylalanine, said amino acid substitution at position 161 is phenylalanine to leucine, said amino acid substitution at position 168 is alanine to phenylalanine, said amino acid substitution at position 169 is leucine to methionine and said amino acid substitution at position 159 is leucine to isoleucine.

* * * * *